(12) United States Patent
Johansson et al.

(10) Patent No.: US 8,063,399 B2
(45) Date of Patent: Nov. 22, 2011

(54) ELECTROACTIVE MATERIALS

(75) Inventors: Gary A. Johansson, Hockessin, DE (US); Eric Maurice Smith, Hockessin, DE (US); Reid John Chesterfield, Santa Barbara, CA (US); Michael Henry Howard, Jr., Montchanin, DE (US); Kyung-Ho Park, Wilmington, DE (US); Nora Sabina Radu, Landenberg, PA (US); Gene M. Rossi, Wilmington, DE (US); Frederick P. Gentry, Bear, DE (US); Troy C. Gehret, Wilmington, DE (US); Daniel David Lecloux, West Chester, PA (US); Adam Fennimore, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/272,210

(22) Filed: Nov. 17, 2008

(65) Prior Publication Data
US 2011/0095269 A1    Apr. 28, 2011

Related U.S. Application Data

(60) Provisional application No. 60/988,951, filed on Nov. 19, 2007.

(51) Int. Cl.
*H01L 51/00* (2006.01)
(52) U.S. Cl. .................. 257/40; 257/103; 257/E51.026; 257/E51.028; 549/59; 428/690
(58) Field of Classification Search .................. 257/40, 257/103, E51.026, E51.028; 549/59; 428/690
See application file for complete search history.

(56) References Cited

U.S. PATENT DOCUMENTS

| 5,707,747 | A | 1/1998 | Tomiyama et al. |
| 5,962,631 | A | 10/1999 | Woo et al. |
| 6,303,238 | B1 | 10/2001 | Thompson et al. |

(Continued)

FOREIGN PATENT DOCUMENTS

EP 681019 B1 9/1999

(Continued)

OTHER PUBLICATIONS

Colon et al—Journal of Polymer Science, Part A, Polymer Chemistry Edition, 1990, vol. 28: 367.
CRC Handbook of Chemistry and Physics, 81st Edition, 2000 (Book Not Included).

(Continued)

*Primary Examiner* — Tu-Tu Ho

(57) ABSTRACT

A compound having Formula I, Formula II, or Formula III:

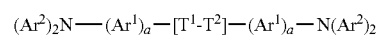

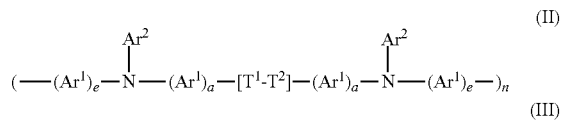

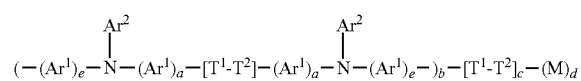

$Ar^1$ may independently be phenylene, substituted phenylene, naphthylene, or substituted naphthylene. $Ar^2$ is the same or different at each occurrence and is an aryl group. M is the same or different at each occurrence and is a conjugated moiety. $T^1$ and $T^2$ are independently the same or different at each occurrence and are conjugated moieties which are connected in a non-planar configuration; a and e are the same or different at each occurrence and are an integer from 1 to 6; b, c, and d are mole fractions such that b+c+d=1.0, with the proviso that c is not zero, and at least one of b and d is not zero, and when b is zero, M has at least two triarylamine units; and n is an integer greater than 1.

18 Claims, 1 Drawing Sheet

U.S. PATENT DOCUMENTS

| | | | |
|---|---|---|---|
| 6,670,645 | B2 | 12/2003 | Grushin et al. |
| 7,023,013 | B2 | 4/2006 | Ricks et al. |
| 7,189,989 | B2 * | 3/2007 | Ise ................................. 257/40 |
| 7,540,978 | B2 | 6/2009 | Pfeiffer et al. |
| 2004/0038459 | A1 | 2/2004 | Brown et al. |
| 2004/0102577 | A1 | 5/2004 | Hsu et al. |
| 2004/0127637 | A1 | 7/2004 | Hsu et al. |
| 2004/0263067 | A1 | 12/2004 | Saitoh et al. |
| 2005/0205860 | A1 | 9/2005 | Hsu et al. |
| 2006/0033421 | A1 | 2/2006 | Matsuura et al. |
| 2006/0216411 | A1 | 9/2006 | Steudel et al. |
| 2007/0285009 | A1 | 12/2007 | Kubota |
| 2008/0071049 | A1 | 3/2008 | Radu et al. |
| 2009/0051281 | A1 | 2/2009 | Inoue et al. |
| 2009/0206748 | A1 | 8/2009 | Moriwaki et al. |

FOREIGN PATENT DOCUMENTS

| | | |
|---|---|---|
| EP | 1624500 A1 | 2/2006 |
| JP | 2000186066 A | 7/2000 |
| JP | 2001226331 A | 8/2001 |
| JP | 2003238501 A | 8/2003 |
| JP | 2007182432 A | 7/2007 |
| WO | 0053565 A1 | 9/2000 |
| WO | 0070655 A3 | 11/2000 |
| WO | 0141512 A1 | 6/2001 |
| WO | 03008424 A1 | 1/2003 |
| WO | 03040257 A1 | 5/2003 |
| WO | 03063555 A1 | 7/2003 |
| WO | 03091688 A2 | 11/2003 |
| WO | 2004016710 A1 | 2/2004 |
| WO | 2006063852 A1 | 6/2006 |
| WO | 2007065678 A1 | 6/2007 |

OTHER PUBLICATIONS

Eaton et al—J. Chem. Soc. Faraday Trans. 2, 1973, 60 pp. 1601-1608.

Gustafsson et al.—Flexible Light-Emitting Diodes Made From Soluble Conducting Polymers, 1992 vol. 357 pp. 477-479.

He et al—A Hole-Transporting Material With Controllable Morphology Containing Binaphthyl and Triphenylamine Chromophores; Advanced Functional Materials, vol. 16, No. 10, 2006, pp. 1343-1348.

Kawamura—Aromatic Oligoamine Derivatives, Their Hole Injection-Transporting Materials, and Their Organic EL Devices With Low Driving Voltage, 2003, 673842.

Hachks Chemical Dictionary; Fourth Edition; McGraw-Hill.

Markus—Photoconductive Cell, Electronics and Nucleonics Dictionary, 1966, pp. 470, 471 and 476 McGraw-Hill.

Shimamura—New Amine Compound for Organic Electroluminescent Device Showign Longer Luminescent Lifetime and Excellent Durability, Chemial Abstracts, 2001, 603530.

Wang—Photoconductive Materials, Kirk-Othmer Encyclopedia of Chemical Technology, Fourth Edition, 1996, vol. 18 pp. 837-860.

Yamamoto et al, Electrically conducting and thermally stable p-conjugated poly(arylene)s prepared by organometallic process, Progress in Polymer Science, vol. 17, pp. 1153-1205, 1992.

PCT International Search Report, PCT/US2008/065191 W. Fitz Authorized Officer, 20080409.

PCT International Search Report, PCT/US2008/065016, M. Redecker Authorized Officer, 20081012.

PCT International Search Report, PCT/US2008/083844, S. Saldamli Authorized Officer, 20090128.

* cited by examiner

ELECTROACTIVE MATERIALS

RELATED APPLICATION DATA

This application claims priority under 35 U.S.C. §119(e) from U.S. Provisional Application No. 60/988,951 filed on Nov. 19, 2007, which is incorporated by reference herein in its entirety.

BACKGROUND INFORMATION

1. Field of the Disclosure

The present disclosure relates to novel electroactive compounds. The disclosure further relates to electronic devices having at least one active layer comprising such an electroactive compound.

2. Description of the Related Art

In organic photoactive electronic devices, such as organic light emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used. Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode.

There is a continuing need for charge transport materials for use in electronic devices.

SUMMARY

There is provided a compound having Formula I, Formula II, or Formula III:

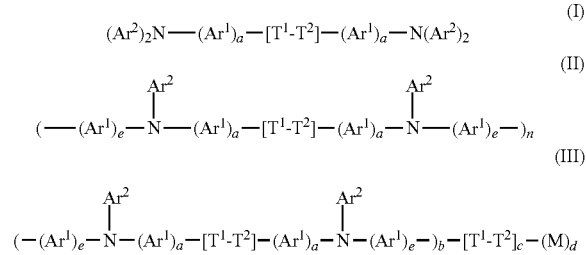

wherein:
Ar$^1$ is the same or different at each occurrence and is selected from the group consisting of phenylene, substituted phenylene, naphthylene, and substituted naphthylene;
Ar$^2$ is the same or different at each occurrence and is an aryl group;
M is the same or different at each occurrence and is a conjugated moiety;
T$^1$ and T$^2$ are independently the same or different at each occurrence and are conjugated moieties which are connected in a non-planar configuration;
a is the same or different at each occurrence and is an integer from 1 to 6;
b, c, and d are mole fractions such that b+c+d=1.0, with the proviso that c is not zero, and at least one of b and d is not zero, and when b is zero, M comprises at least two triarylamine units;
e is the same or different at each occurrence and is an integer from 1 to 6; and
n is an integer greater than 1.

There is also provided an electronic device having at least one layer comprising the above compound.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
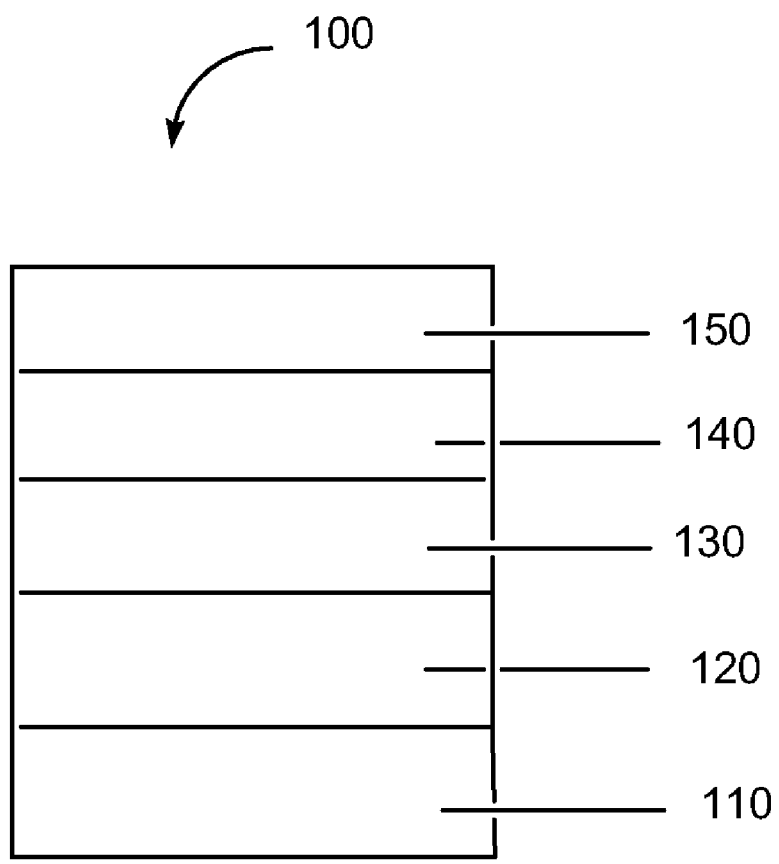
FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

There is provided a compound having Formula I, Formula II, or Formula III:

$$(Ar^2)_2N-(Ar^1)_a-[T^1-T^2]-(Ar^1)_a-N(Ar^2)_2 \quad (I)$$

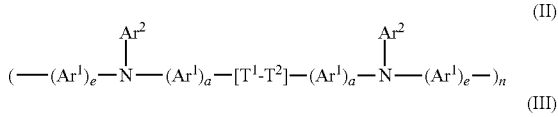

wherein:
Ar$^1$ is the same or different at each occurrence and is selected from the group consisting of phenylene, substituted phenylene, naphthylene, and substituted naphthylene;
Ar$^2$ is the same or different at each occurrence and is an aryl group;
M is the same or different at each occurrence and is a conjugated moiety;
T$^1$ and T$^2$ are independently the same or different at each occurrence and are conjugated moieties which are connected in a non-planar configuration;
a is the same or different at each occurrence and is an integer from 1 to 6;
b, c, and d are mole fractions such that b+c+d=1.0, with the proviso that c is not zero, and at least one of b and d is not zero, and when b is zero, M comprises at least two triarylamine units;

e is the same or different at each occurrence and is an integer from 1 to 6; and n is an integer greater than 1.

There is also provided an electronic device having at least one layer comprising the above compound.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Electroactive Compound, the Electronic Device, and finally Examples.

1. Definitions and Clarification of Terms

Before addressing details of embodiments described below, some terms are defined or clarified.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tertbutyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aryl" means an aromatic carbocyclic moiety, which may be a single ring (monocyclic) or multiple rings (bicyclic, or more) fused together or linked covalently. Any suitable ring position of the aryl moiety may be covalently linked to the defined chemical structure. Examples of aryl moieties include, but are not limited to, phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. In some embodiments, aryl groups have 6 to 60 carbon atoms; in some embodiments, 6 to 30 carbon atoms. The term is intended to include heteroaryl groups. Heteroaryl groups may have from 4-50 carbon atoms; in some embodiments, 4-30 carbon atoms.

The term "alkoxy" is intended to mean the group —OR, where R is alkyl.

The term "aryloxy" is intended to mean the group —OR, where R is aryl.

Unless otherwise indicated, all groups can be substituted or unsubstituted. An optionally substituted group, such as, but not limited to, alkyl or aryl, may be substituted with one or more substituents which may be the same or different. Suitable substituents include D, alkyl, aryl, nitro, cyano, —N($R^7$)($R^8$), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxane, thioalkoxy, —S(O)$_2$—N(R')(R"), —C(=O)—N(R')(R"), (R')(R")N-alkyl, (R')(R")N-alkoxyalkyl, (R')(R")N-alkylaryloxyalkyl, —S(O)$_s$-aryl (where s=0-2) or —S(O)$_s$-heteroaryl (where s=0-2). Each R' and R" is independently an optionally substituted alkyl, cycloalkyl, or aryl group. R' and R", together with the nitrogen atom to which they are bound, can form a ring system in certain embodiments. Substituents may also be crosslinking groups.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport material facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "crosslinkable group" or "crosslinking group" is intended to mean a group than can lead to crosslinking via thermal treatment or exposure to radiation. In some embodiments, the radiation is UV or visible.

The term "electroactive" as it refers to a layer or a material, is intended to indicate a layer or material which electronically facilitates the operation of the device. Examples of active materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The prefix "fluoro" is intended to indicate that one or more hydrogens in a group has been replaced with fluorine.

The prefix "hetero" indicates that one or more carbon atoms has been replaced with a different atom. In some embodiments, the heteroatom is O, N, S, or combinations thereof.

The term "non-planar configuration" as it refers to [$T^1$-$T^2$] in Formulae I-III herein, is intended to mean that the immediately adjacent groups in $T^1$ and $T^2$ are not oriented in the same plane.

The term "oxyalkyl" is intended to mean a heteroalkyl group having one or more carbons replaced with oxygens. The term includes groups which are linked via an oxygen.

The term "photoactive" is intended to mean to any material that exhibits electroluminescence or photosensitivity.

The term "silyl" refers to the group $R_3Si$—, where R is H, D, C1-20 alkyl, fluoroalkyl, or aryl. In some embodiments, one or more carbons in an R alkyl group are replaced with Si. In some embodiments, the silyl groups are (hexyl)$_2$Si(Me)CH$_2$CH$_2$Si(Me)$_2$- and [CF$_3$(CF$_2$)$_6$CH$_2$CH$_2$]$_2$SiMe-.

The term "siloxane" refers to the group (RO)$_3$Si—, where R is H, D, C1-20 alkyl, or fluoroalkyl.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics,* 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Electroactive Compound

The compound described herein has Formula I, Formula II, or Formula III:

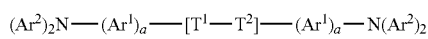

(I)

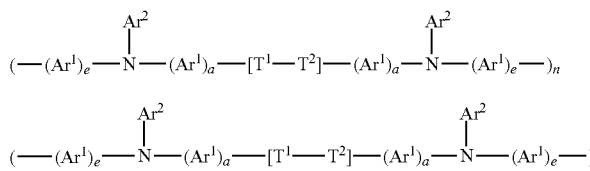

(II)

(III)

wherein:
Ar$^1$ is the same or different at each occurrence and is selected from the group consisting of phenylene, substituted phenylene, naphthylene, and substituted naphthylene;
Ar$^2$ is the same or different at each occurrence and is an aryl group;
M is the same or different at each occurrence and is a conjugated moiety;
T$^1$ and T$^2$ are independently the same or different at each occurrence and are conjugated moieties which are connected in a non-planar configuration;
a is the same or different at each occurrence and is an integer from 1 to 6;
b, c, and d are mole fractions such that b+c+d=1.0, with the proviso that c is not zero, and at least one of b and d is not zero, and when b is zero, M comprises at least two triarylamine units;
e is the same or different at each occurrence and is an integer from 1 to 6; and
n is an integer greater than 1.

In some embodiments, at least one Ar$^1$ is a substituted phenyl with a substituent selected from the group consisting of alkyl, alkoxy, silyl, and a substituent with a crosslinking group. In some embodiments, a is 1-3. In some embodiments a is 1-2. In some embodiments, a is 1. In some embodiments, e is 1-4. In some embodiments, e is 1-3. In some embodiments, e=1. In some embodiments, at least one Ar$^1$ has a substituent that has a crosslinking group.

In some embodiments, Ar$^2$ has Formula a

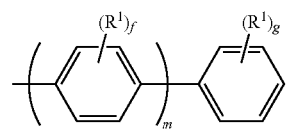

Formula a where:
R$^1$ is the same or different at each occurrence and is selected from the group consisting of alkyl, alkoxy, siloxane and silyl;
f is the same or different at each occurrence and is an integer from 0-4;
g is an integer from 0-5; and
m is an integer from 1 to 5.
In some embodiments, at least one of f and g is not zero. In some embodiments, m=1-3.

In some embodiments, Ar$^2$ is selected from the group consisting of a group having Formula a, naphthyl, phenylnaphthyl, and naphthylphenyl. In some embodiments, Ar$^2$ is selected from the group consisting phenyl, p-biphenyl, p-terphenyl, naphthyl, phenylnaphthyl, and naphthylphenyl. In some embodiments, Ar$^2$ is selected from the group consisting of phenyl, biphenyl, and terphenyl.

Any of the aromatic rings in Formulae I-III may be substituted at any position. The substituents may be present to improve one or more physical properties of the compound, such as solubility. In some embodiments, the substituents are selected from the group consisting of C$_{1-12}$ alkyl groups, C$_{1-12}$ alkoxy groups and silyl groups. In some embodiments, the alkyl groups are heteroalkyl groups. In some embodiments, the alkyl groups are fluoroalkyl groups. In some embodiments, at least one Ar$^2$ has an alkyl, alkoxy or silyl substituent. The substituents may be present to provide crosslinking capability. In some embodiments, crosslinking substituents are present on at least one Ar$^2$. In some embodiments, crosslinking substituents are present on at least one M moiety. In some embodiments, there is at least one substituent which includes a crosslinkable group. Examples of crosslinkable groups include, but are not limited to vinyl, acrylate, perfluorovinylether, 1-benzo-3,4-cyclobutane, siloxane, cyanate groups, cyclic ethers (epoxides), cycloalkenes, and acetylenic groups.

In one embodiment, the crosslinkable group is vinyl.

The $T^1$-$T^2$ group introduces non-planarity into the backbone of the compound. The moiety in $T^1$ that is directly linked to a moiety in $T^2$ is linked such that the $T^1$ moiety is oriented in a plane that is different from the moiety in $T^2$ to which it is linked. Although other parts of the $T^1$ unit, for example, substituents, may lie in one or more different planes, it is the plane of the linking moiety in $T^1$ and the linking moiety in $T^2$ in the compound backbone that provide the non-planarity. Because of the non-planar $T^1$-$T^2$ linkage, the compounds are chiral. In general, they are formed as racemic mixtures. The compounds can also be in enantiomerically pure form. The non-planarity can be viewed as the restriction to free rotation about the $T^1$-$T^2$ bond. Rotation about that bond leads to racemization. The half-life of racemization for $T^1$-$T^2$ is greater than that for an unsubstituted biphenyl. In some embodiments, the half-life or racemization is 12 hours or greater at 20° C.

$T^1$ and $T^2$ are conjugated moieties. In some embodiments, $T^1$ and $T^2$ are aromatic moieties. In some embodiments, $T^1$ and $T^2$ are selected from the group consisting of phenylene, naphthylene, and anthracenyl groups.

In some embodiments, $[T^1$-$T^2]$ is a substituted biphenylene group. The term "biphenylene" is intended to mean a biphenyl group having two points of attachment to the compound backbone. The term "biphenyl" is intended to mean a group having two phenyl units joined by a single bond. The biphenylene group can be attached at one of the 2,3-, 4-, or 5-positions and one of the 2', 3'-, 4'-, or 5'-positions. The substituted biphenylene group has at least one substituent in the 2-position. In some embodiments, the biphenylene group has substituents in at least the 2- and 2'-positions.

In some embodiments, $[T^1$-$T^2]$ is a binaphthylene group. The term "binaphthylene" is intended to mean a binapthyl group having 2 points of attachment to the compound backbone. The term "binaphthyl" is intended to mean a group having two naphthalene units joined by a single bond. In some embodiments, the binaphthylene group is a 1,1'-binaphthylene, which is attached to the compound backbone at one of the 3-, 4-, 5-, 6, or 7-positions and one of the 3'-, 4'-, 5'-, 6', or 7'-positions. This is illustrated below, where the dashed lines represent possible points of attachment.

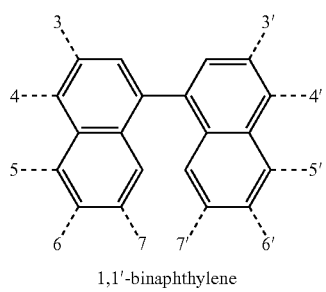

1,1'-binaphthylene

In some embodiments, the binaphthylene group is a 1,2'-binaphthylene having at least one substituent at the 8- or 9'-position, and which is attached to the compound backbone at one of the 3-, 4-, 5-, 6, or 7-positions and one of the 4'-, 5'-, 6'-, 7', or 8'-positions. This is illustrated below, where the dashed lines represent possible points of attachment and at least one R represents a substituent.

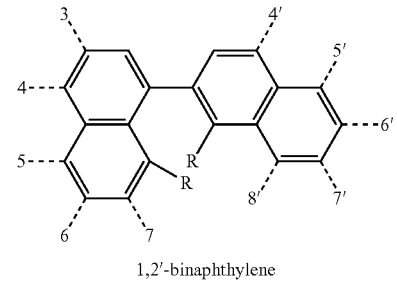

1,2'-binaphthylene

In some embodiments, the binaphthylene group is a 2,2'-binaphthylene having at least one substituent at the 8- or 9'-position, and which is attached to the compound backbone at one of the 4-, 5-, 6-, 7, or 8-positions and one of the 4'-, 5'-, 6'-, 7', or 8'-positions. This is illustrated below, where the dashed lines represent possible points of attachment and at least one R represents a substituent.

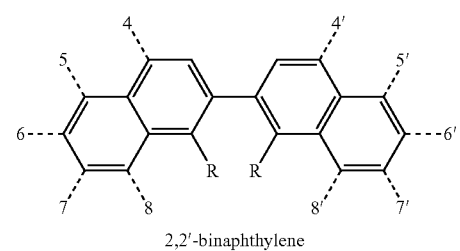

2,2'-binaphthylene

In some embodiments, $[T^1$-$T^2]$ is a phenylene-naphthylene group. In some embodiments, $[T^1$-$T^2]$ is a phenylene-1-naphthylene group, which is attached to the compound backbone at one of the 3-, 4-, or 5-positions in the phenylene and one of the 3-, 4-, or 5-positions of the naphthylene. In some embodiments, $[T^1$-$T^2]$ is a phenylene-2-naphthylene group, which is attached to the compound backbone at one of the 3-, 4-, or 5-positions in the phenylene and one of the 4-, 5-, 6-, 7-, or 8-positions of the naphthylene.

In some embodiments, the biphenylene, binaphthylene, and phenylene-naphthylene groups are substituted at one or more positions.

In some embodiments, $[T^1$-$T^2]$ is selected from one of the following:

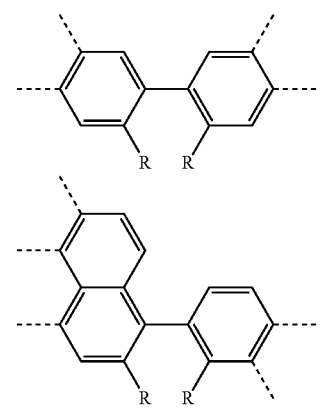

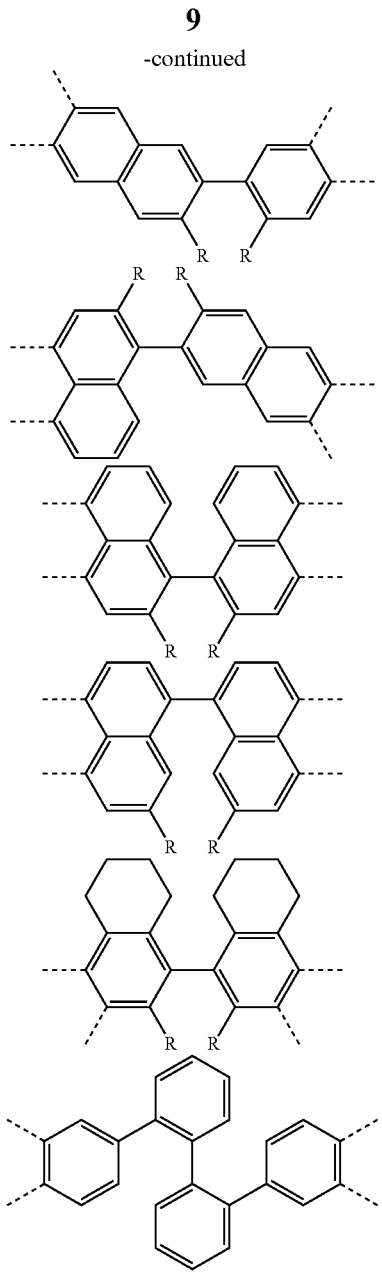

where R is the same or different and is selected from the group consisting of alkyl, aryl, alkoxy, aryloxy, fluoroalkyl, fluoroaryl, fluoroaryloxy fluoroalkyloxy, oxyalkyl, alkenyl groups, silyl, siloxane and crosslinking groups. The dashed line represents a possible point of attachment to the compound backbone. In some embodiments, R is a $C_{1-10}$ alkyl or alkoxy; in some embodiments, a $C_{3-8}$ branched alkyl or alkoxy. In some embodiments, the two R groups are joined together to form a non-aromatic ring.

In some embodiments, $[T^1-T^2]$ is a 1,1-binaphthylene group which is attached to the compound backbone at the 4 and 4' positions, referred to as 4,4'-(1,1-binaphthylene). In some embodiments, the 4,4'-(1,1-binaphthylene) is the only isomer present. In some embodiments, two or more isomers are present. In some embodiments, the 4,4'-(1,1-binaphthylene) is present with up to 50% by weight of a second isomer. In some embodiments, the second isomer is selected from the group consisting of 4,5'-(1,1-binaphthylene), 4,6'-(1,1-binaphthylene), and 4,7'-(1,1-binaphthylene).

Formula III represents a copolymer in which there is at least one T moiety and at least one other conjugated moiety. In some embodiments, c is at least 0.4. In some embodiments, c is in the range of 0.4 to 0.6. The copolymers can be random, alternating, or block copolymers. In some embodiments, M comprises triarylamine units. In some embodiments, M is an aromatic group. In some embodiments, M is an aromatic unit having a crosslinkable substituent. The amount of M having a crosslinkable substituent is generally between 4 and 20 mole percent.

Some non-limiting examples of compounds having Formula I include Compounds A and B below.

Compound A:

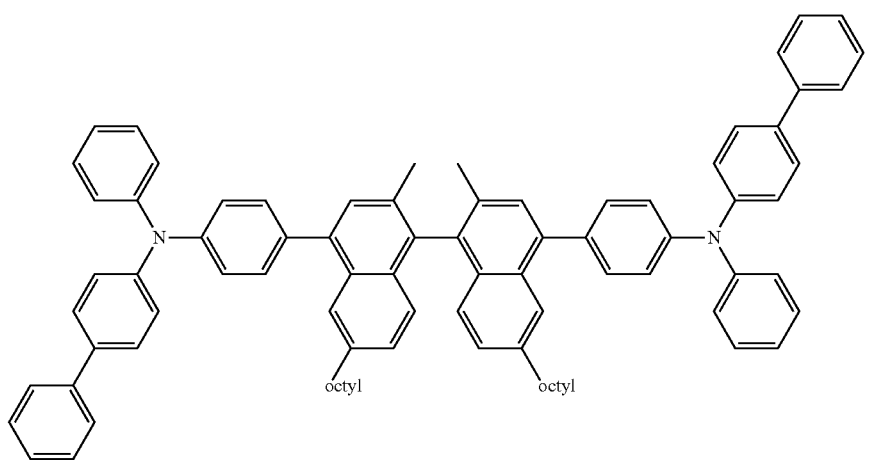

Compound B:
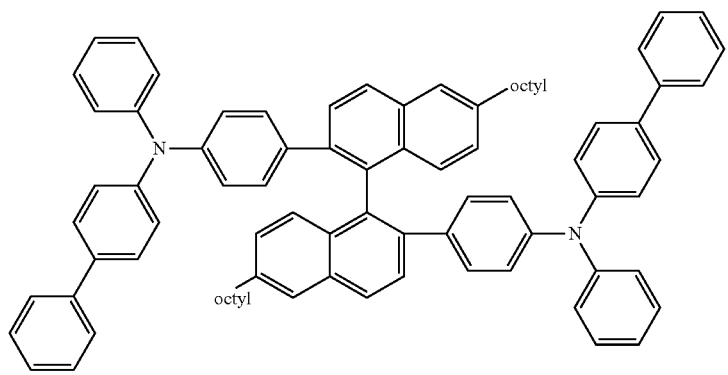
Some non-limiting examples of compounds having Formula II include Compounds C through M and M1 below.
Compound C
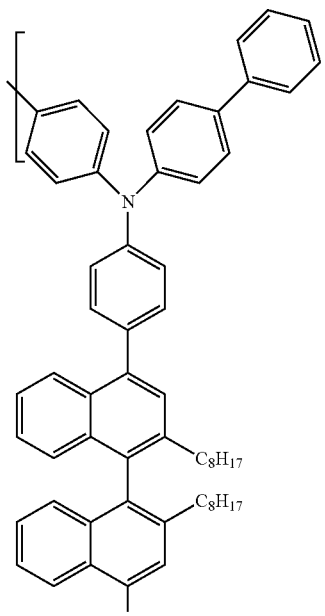
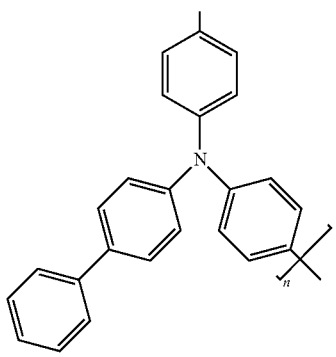

-continued
Compound D:
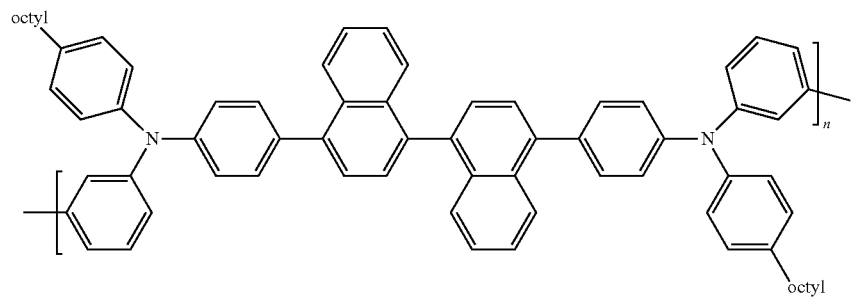
Compound E:
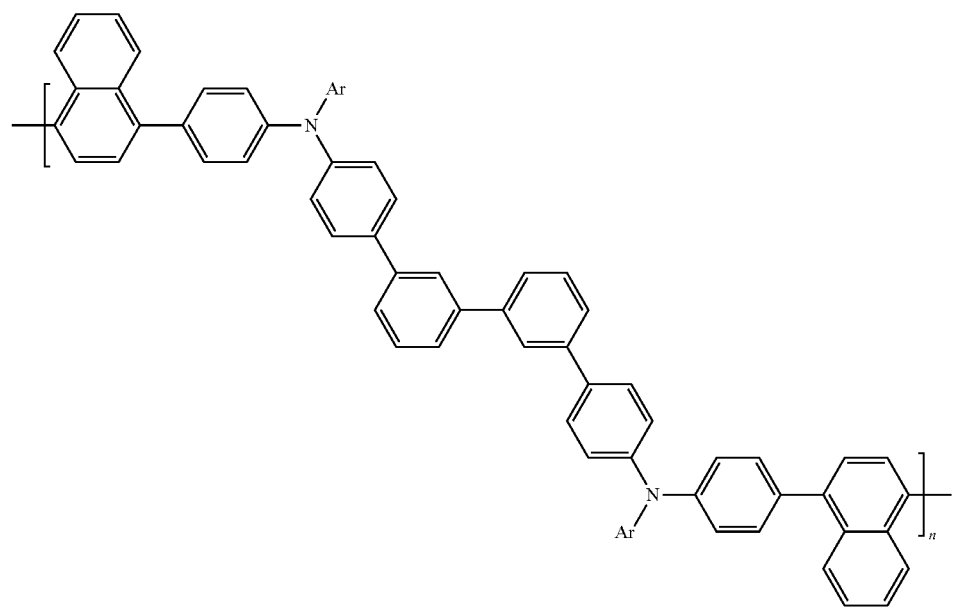
Ar = phenyl, biphenyl
Compound F:
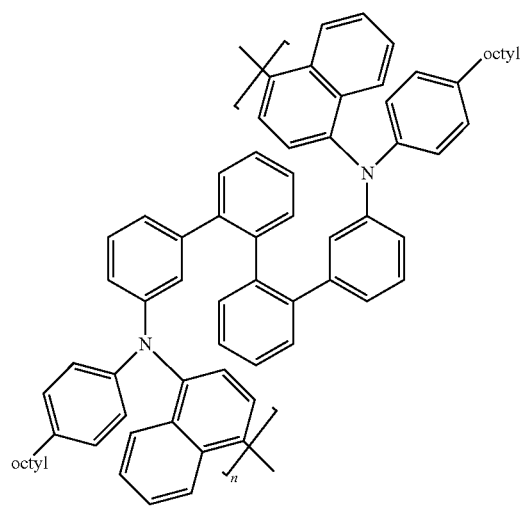

Compound G:
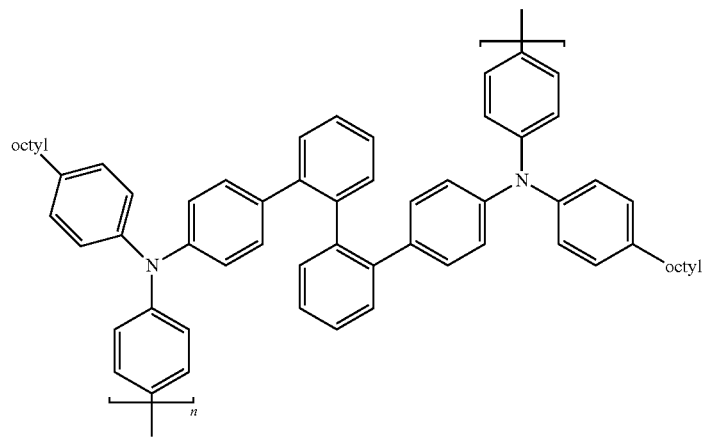
Compound H:
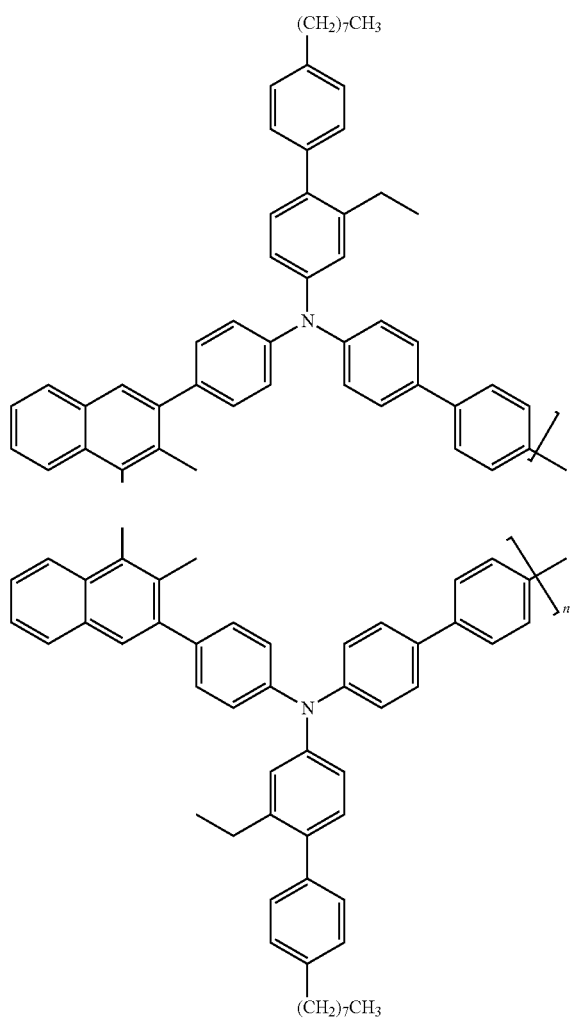

-continued
Compound I:
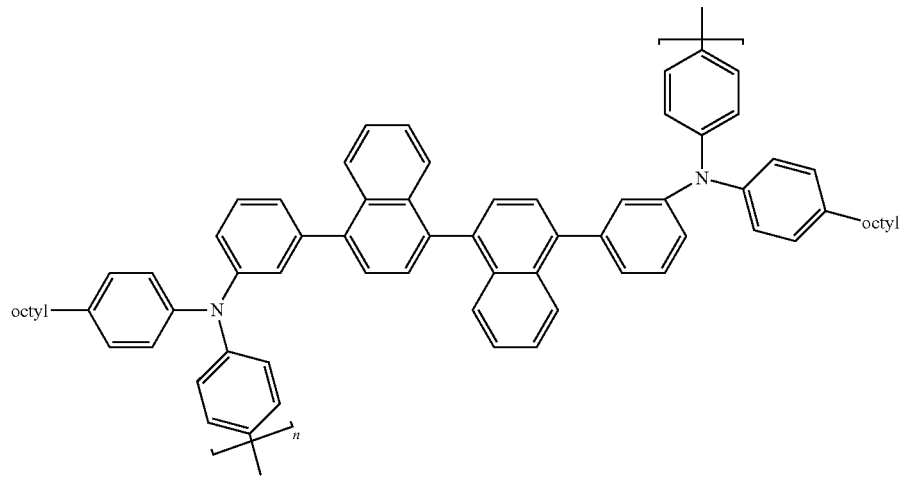
Compound J:
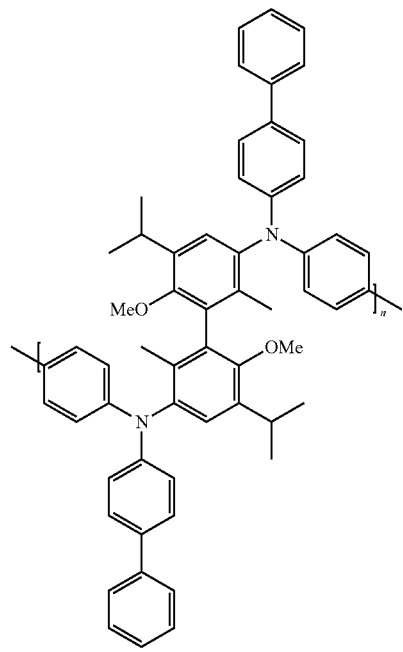
Compound K:
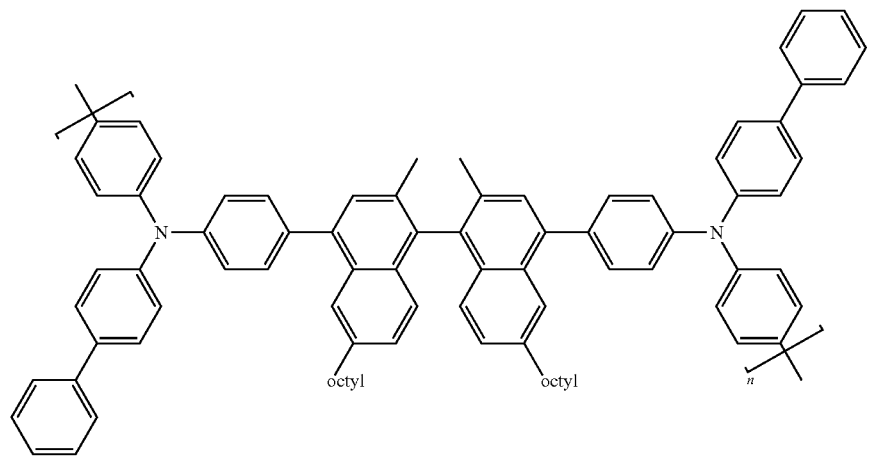

Compound L:
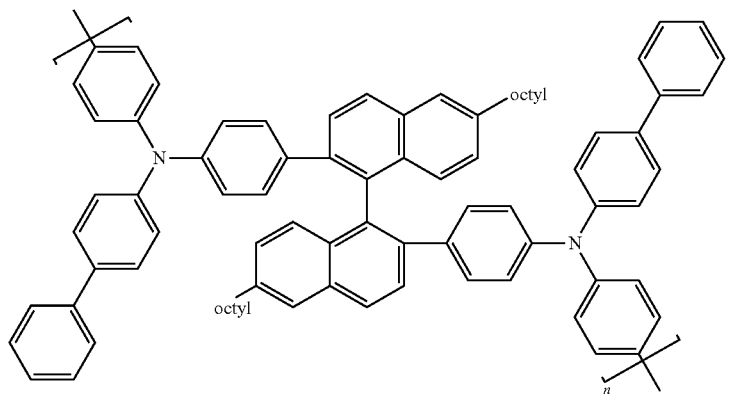
Compound M:
Compound M1:
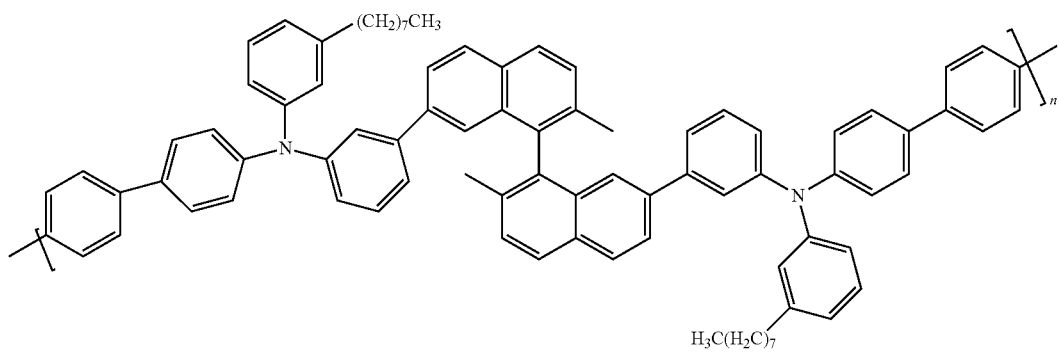
Some non-limiting examples of compounds having Formula III include Compounds N through Y4 below.
Compound N:
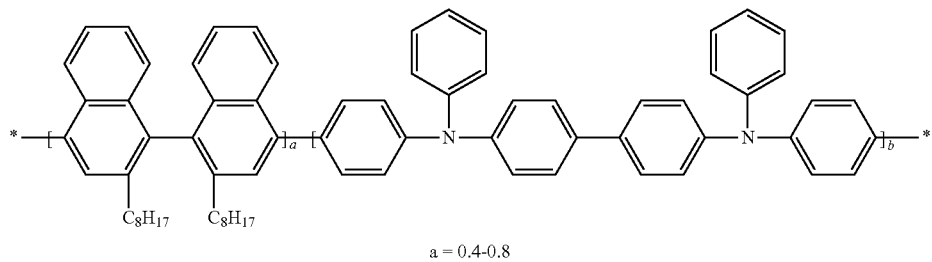
a = 0.4-0.8
b = 0.2-0.6
Compound O:
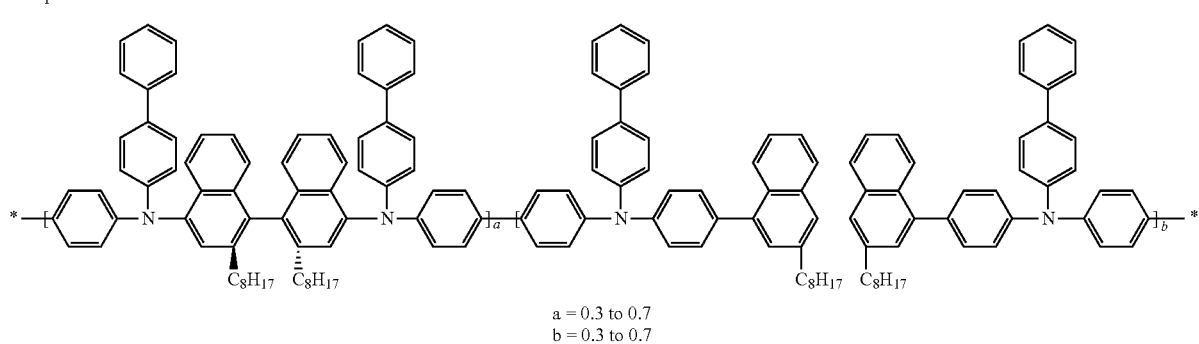
a = 0.3 to 0.7
b = 0.3 to 0.7

-continued
Compound P:
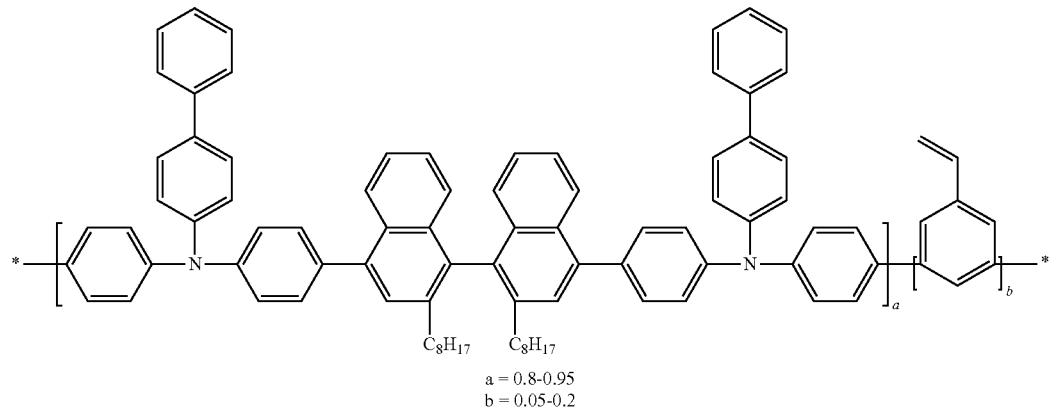
$a = 0.8\text{-}0.95$
$b = 0.05\text{-}0.2$
Compound Q:
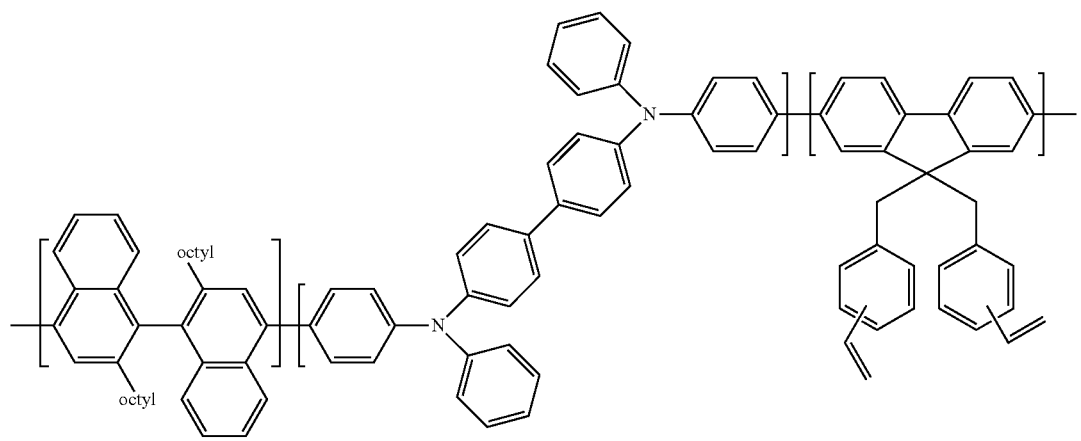
Compound R:
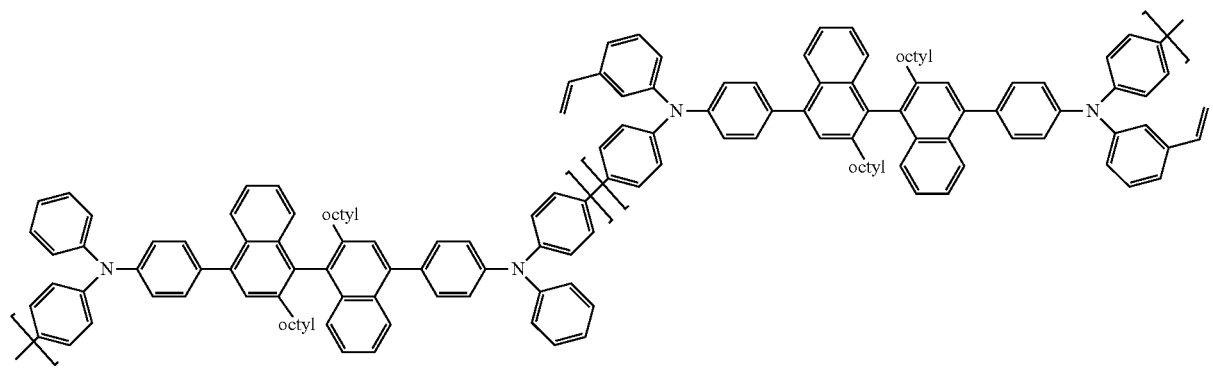

Compound S:
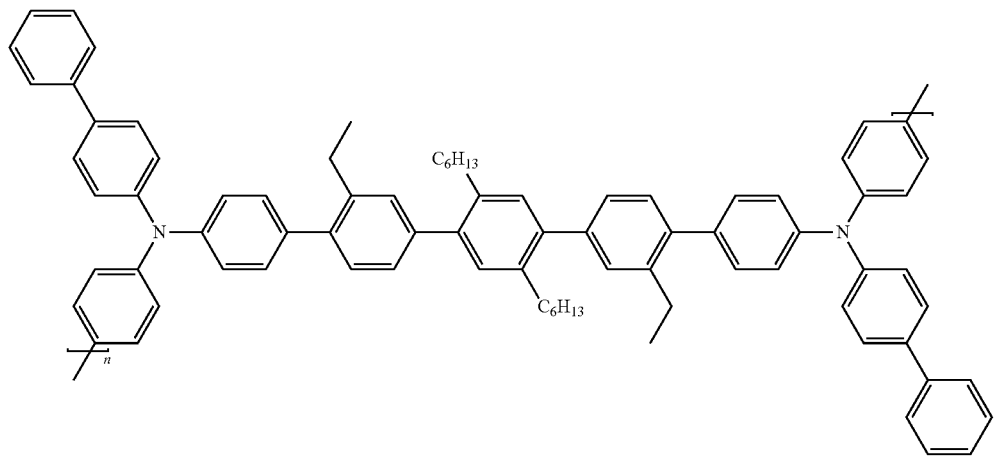
Compound T:
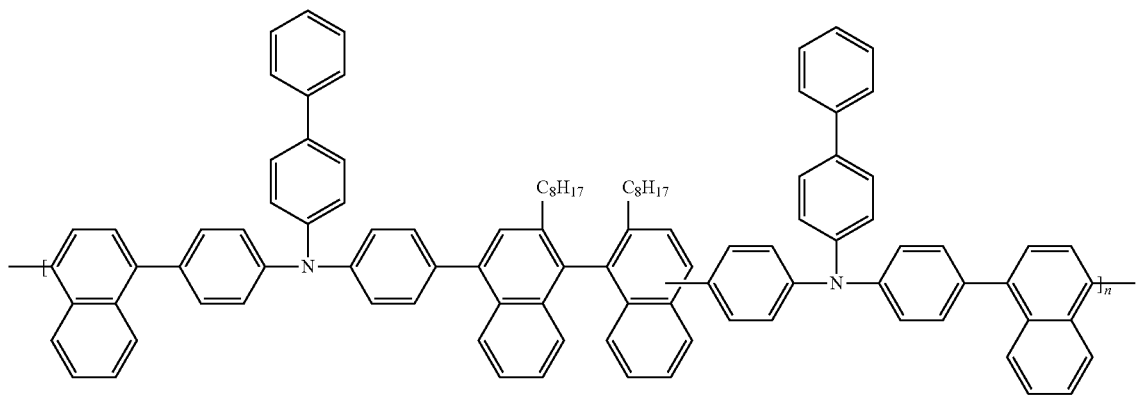
Compound U:
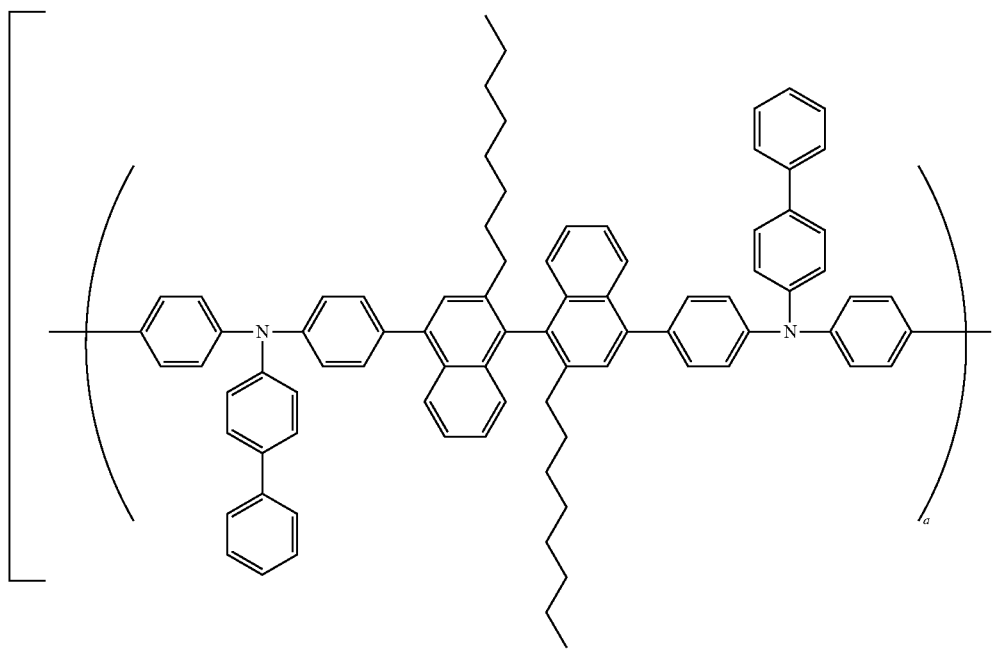

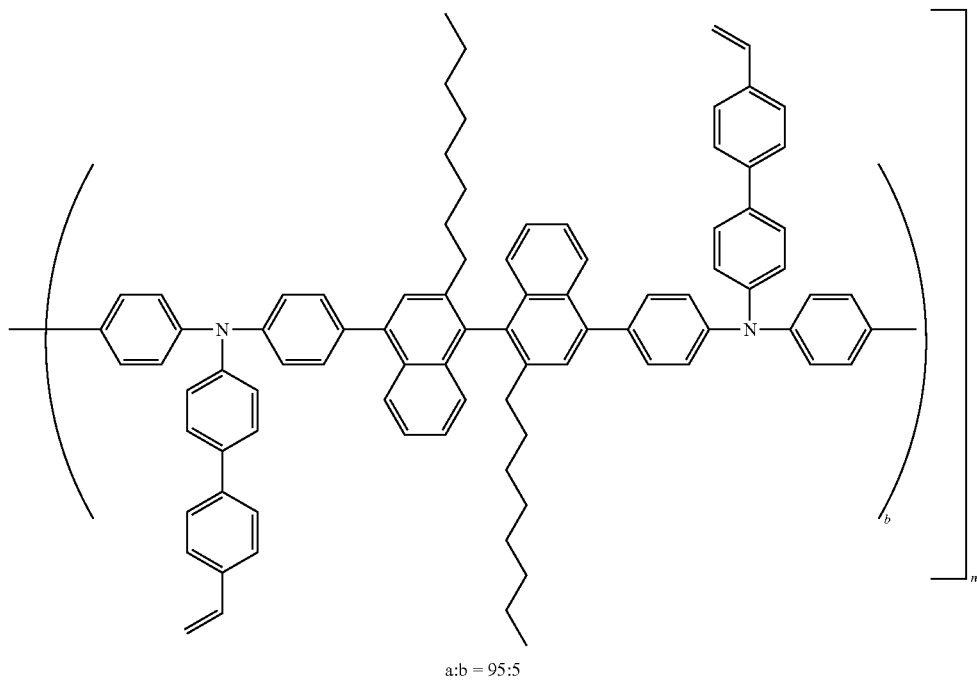
a:b = 95:5
Compound V:
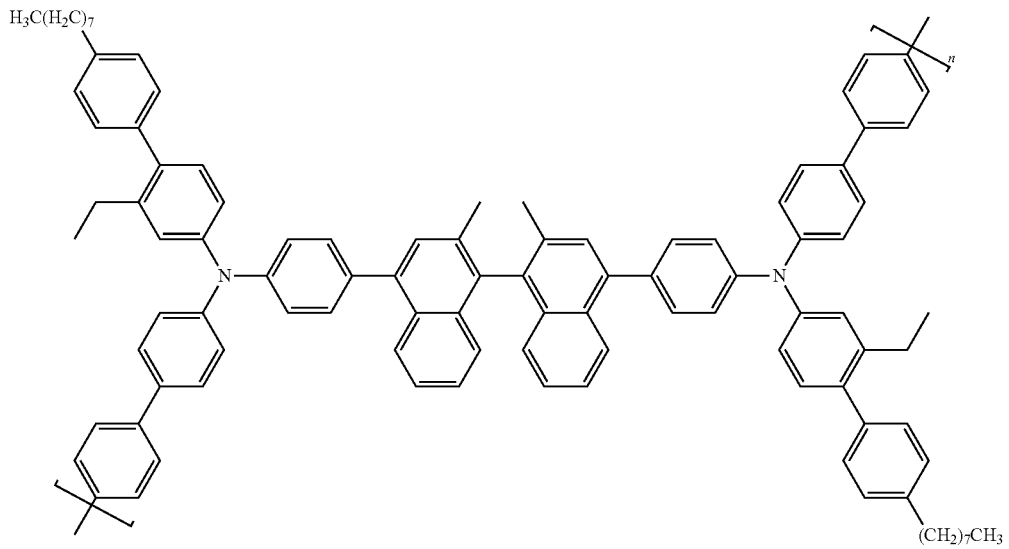
Compound W:
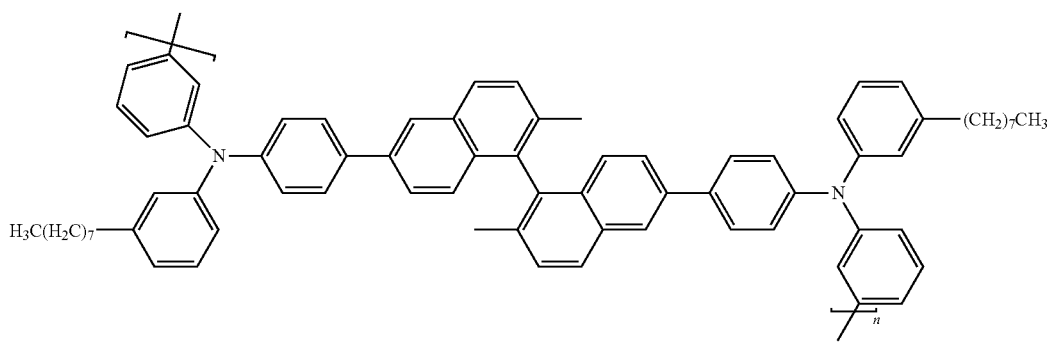

Compound X:

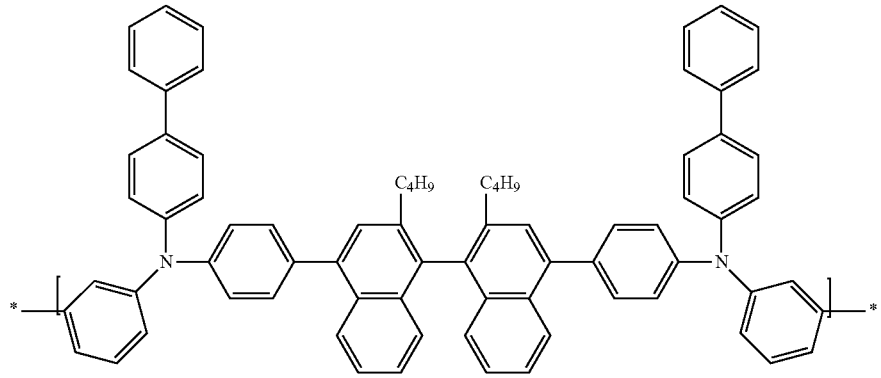

Compounds Y1-Y4

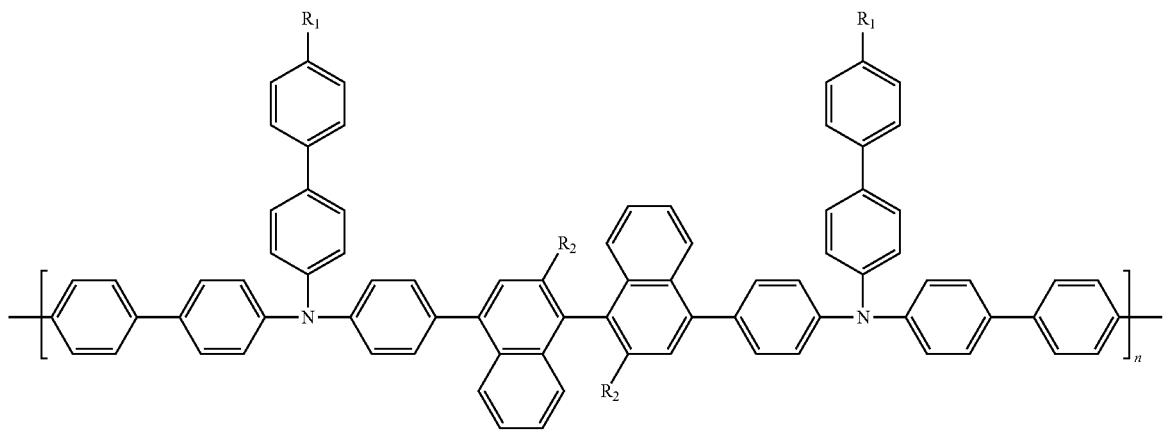

Compound Y
compound Y1: $R_1$ = pentyl; $R_2$ = butyl
compound Y2: $R_1$ = heptyl; $R_2$ = octyl
compound Y3: $R_1$ = propyl; $R_2$ = octyl
compound Y4: $R_1$ = octyl; $R_2$ = methyl The new compounds can be made using any technique that will yield a C—C or C—N bond. A variety of such techniques are known, such as Suzuki, Yamamoto, Stille, and Pd- or Ni-catalyzed C—N couplings. The compounds can be formed into layers using solution processing techniques. The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The new compounds described herein have can be used as hole transport materials, as photoactive materials, and as hosts for photoactive materials. The new compounds have hole mobilities and HOMO/LUMO energies similar to efficient small molecule hole transport compounds such as N,N'-diphenyl-N,N'-bis(3-methylphenyl)-[1,1'-biphenyl]-4,4'-diamine (TPD) and N,N'-bis(naphthalen-1-yl)-N,N'-bis-(phenyl)benzidine (α-NPB). Compounds such as TPD and NPD generally must be applied using a vapor deposition technique.

3. Electronic Devices

Organic electronic devices that may benefit from having one or more layers comprising at least one compound as described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure is shown in FIG. 1. The device 100 has an anode layer 110 and a cathode layer 150, and a photoactive layer 130 between them. Adjacent to the anode is a layer 120 comprising a charge transport material, for example, a hole transport material. Adjacent to the cathode may be a charge transport layer 140 comprising an electron transport material. As an option, devices may use one or more additional hole injection or hole transport layers (not shown) next to the anode 110 and/or one or more additional electron injection or electron transport layers (not shown) next to the cathode 150.

As used herein, the term "photoactive" refers to a material that emits light when activated by an applied voltage (such as in a light-emitting diode or light-emitting electrochemical cell), or responds to radiant energy and generates a signal with or without an applied bias voltage (such as in a photodetector). In one embodiment, a photoactive layer is an emitter layer.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and photovoltaic cells, as these terms are described in Kirk-Othmer Concise Encyclopedia of Chemical Technology, $4^{th}$ edition, p. 1537, (1999).

In some embodiments, the hole transport layer 120 comprises at least one new electroactive compound as described herein.

In some embodiments, the photoactive layer 130 comprises at least one new electroactive compound as described herein, wherein the electroactive compound is photoactive.

In some embodiments, the photoactive layer 130 comprises at least one new electroactive compound as described herein, wherein the electroactive compound serves as a host having a photoactive material dispersed therein.

The other layers in the device can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

In some embodiments, the device further comprises a buffer layer between the anode and the layer comprising the new polymer. The term "buffer layer" is intended to mean a layer comprising electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Buffer materials may be polymers, oligomers, or small molecules, and may be in the form of solutions, dispersions, suspensions, emulsions, colloidal mixtures, or other compositions. The buffer layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The buffer layer can comprise charge transfer compounds, and the like, such as copper phthalocyanine and the tetrathiafulvalene-tetracyanoquinodimethane system (TTF-TCNQ). In one embodiment, the buffer layer is made from a dispersion of a conducting polymer and a colloid-forming polymeric acid. Such materials have been described in, for example, published U.S. patent applications 2004-0102577, 2004-0127637, and 2005/205860.

In some embodiments, hole transport layer 120 comprises the new electroactive compound described herein. In some embodiments, hole transport layer 120 consists essentially of the new electroactive compound described herein. In some embodiments, layer 120 comprises other hole transport materials. Examples of other hole transport materials for layer 120 have been summarized for example, in Kirk Othmer Encyclopedia of Chemical Technology, Fourth Edition, Vol. 18, p. 837 860, 1996, by Y. Wang. Both hole transporting molecules and polymers can be used. Commonly used hole transporting molecules include, but are not limited to: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis (3-methylphenyl)-N,N,N',N'-2,5-phenylenediamine (PDA), a-phenyl 4-N,N-diphenylaminostyrene (TPS), p-(diethylamino) benzaldehyde diphenylhydrazone (DEH), triphenylamine (TPA), bis[4 (N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N' tetrakis(4-methylphenyl)-(1,1'-biphenyl)-4,4'-diamine (TTB), N,N'-Bis(naphthalen-1-yl)-N,N'-bis-(phenyl)benzidine (α-NPB), and porphyrinic compounds, such as copper phthalocyanine. Commonly used hole transporting polymers include, but are not limited to, polyvinylcarbazole, (phenylmethyl)polysilane, and polyaniline. It is also possible to obtain hole transporting polymers by doping hole transporting molecules such as those mentioned above into polymers such as polystyrene and polycarbonate. Buffer layers and/or hole transport layer can also comprise polymers of thiophene, aniline, or pyrrole with polymeric fluorinated sulfonic acids, as described in published US applications 2004/102577, 2004/127637, and 2005/205860.

Any organic electroluminescent ("EL") material can be used as the photoactive material in layer 130. Such materials include, but are not limited to, one of more compounds of the instant invention, small organic fluorescent compounds, fluorescent and phosphorescent metal complexes, conjugated polymers, and mixtures thereof. Examples of fluorescent compounds include, but are not limited to, pyrene, perylene, rubrene, coumarin, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, and mixtures thereof. Examples of conjugated polymers include, but are not limited to poly(phenylenevinylenes), polyfluorenes, poly (spirobifluorenes), polythiophenes, poly(p-phenylenes), copolymers thereof, and mixtures thereof. The materials may also be present in admixture with a host material. In some embodiments, the host material is a hole transport material or an electron transport material. In some embodiments, the host is the new electroactive compound described herein. In some embodiments, the ratio of host material to photoactive material is in the range of 5:1 to 20:1; in some embodiments, 10:1 to 15:1. In some embodiments, the photoactive layer consists essentially of a photoactive material and the new electroactive compound described herein.

Examples of electron transport materials which can be used in the electron transport layer 140 and/or the optional layer between layer 140 and the cathode include metal chelated oxinoid compounds, such as tris(8-hydroxyquinolato) aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1, 2,4-triazole (TAZ), and 1,3,5-tri(phenyl-2-benzimidazole) benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

The choice of materials for each of the component layers is preferably determined by balancing the goals of providing a device with high device efficiency with device operational lifetime. Other layers may also be present in the device. There may be one or more hole injection and/or hole transport layers between the buffer layer and the organic active layer. There may be one or more electron transport layers and/or electron injection layers between the organic active layer and the cathode.

The device can be prepared by a variety of techniques, including sequentially depositing the individual layers on a suitable substrate. Substrates such as glass and polymeric films can be used. Conventional vapor deposition techniques can be used, such as thermal evaporation, chemical vapor deposition, and the like. Alternatively, the organic layers can be applied by liquid deposition using suitable solvents. The liquid can be in the form of solutions, dispersions, or emulsions. Typical liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing. any conventional coating or printing technique, including but not limited to spin-coating, dip-coating, roll-to-roll techniques, ink jet printing, screen-printing, gravure printing and the like.

The new electroactive compounds described herein can be applied by liquid deposition from a liquid composition. The term "liquid composition" is intended to mean a liquid medium in which a material is dissolved to form a solution, a liquid medium in which a material is dispersed to form a dispersion, or a liquid medium in which a material is suspended to form a suspension or an emulsion.

In one embodiment, the different layers have the following range of thicknesses: anode 110, 500-5000 Å, in one embodiment 1000-2000 Å; hole transport layer 120, 50-2000 Å, in one embodiment 200-1000 Å; photoactive layer 130, 10-2000 Å, in one embodiment 100-1000 Å; layer 140, 50-2000 Å, in one embodiment 100-1000 Å; cathode 150, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In one embodiment, the device has the following structure, in order: anode, buffer layer, hole transport layer, photoactive layer, electron transport layer, electron injection layer, cathode. In one embodiment, the anode is made of indium tin oxide or indium zinc oxide. In one embodiment, the buffer layer comprises a conducting polymer selected from the group consisting of polythiophenes, polyanilines, polypyrroles, copolymers thereof, and mixtures thereof. In one embodiment, the buffer layer comprises a complex of a conducting polymer and a colloid-forming polymeric acid.

In one embodiment, the hole transport layer comprises the new compound described herein. In one embodiment, the hole transport layer comprises a compound having triarylamine or triarylmethane groups. In one embodiment, the hole transport layer comprises a material selected from the group consisting of TPD, MPMP, NPB, CBP, and mixtures thereof, as defined above.

In one embodiment, the photoactive layer comprises an electroluminescent metal complex and a host material. The host can be a charge transport material. In one embodiment, the host is the new electroactive compound described herein. In one embodiment, the electroluminescent complex is present in an amount of at least 1% by weight. In one embodiment, the electroluminescent complex is 2-20% by weight. In one embodiment, the electroluminescent complex is 20-50% by weight. In one embodiment, the electroluminescent complex is 50-80% by weight. In one embodiment, the electroluminescent complex is 80-99% by weight. In one embodiment, the metal complex is a cyclometalated complex of iridium, platinum, rhenium, or osmium. In one embodiment, the photoactive layer further comprises a second host material.

In one embodiment, the electron transport layer comprises a metal complex of a hydroxyaryl-N-heterocycle. In one embodiment, the hydroxyaryl-N-heterocycle is unsubstituted or substituted 8-hydroxyquinoline. In one embodiment, the metal is aluminum. In one embodiment, the electron transport layer comprises a material selected from the group consisting of tris(8-hydroxyquinolinato)aluminum, bis(8-hydroxyquinolinato)(4-phenylphenolato)aluminum, tetrakis(8-hydroxyquinolinato)zirconium, tetrakis(8-hydroxyquinolinato) hafnium, and mixtures thereof. In one embodiment, the electron injection layer is LiF or $Li_2O$. In one embodiment, the cathode is Al or Ba/Al. In one embodiment, there is an electron transport layer comprising a material selected from the group consisting of tris(8-hydroxyquinolinato)aluminum, bis(8-hydroxyquinolinato)(4-phenylphenolato)aluminum, tetrakis(8-hydroxyquinolinato)zirconium, tetrakis(8-hydroxyquinolinato)hafnium, and mixtures thereof, and an electron injection layer comprising LiF or $Li_2O$.

In one embodiment, the device is fabricated by liquid deposition of the buffer layer, the hole transport layer, and the photoactive layer, and by vapor deposition of the electron transport layer, the electron injection layer, and the cathode.

The buffer layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is selected from the group consisting of alcohols, ketones, cyclic ethers, and polyols. In one embodiment, the organic liquid is selected from dimethylacetamide ("DMAc"), N-methylpyrrolidone ("NMP"), dimethylformamide ("DMF"), ethylene glycol ("EG"), aliphatic alcohols, and mixtures thereof. The buffer material can be present in the liquid medium in an amount from 0.5 to 10 percent by weight. Other weight percentages of buffer material may be used depending upon the liquid medium. The buffer layer can be applied by any continuous or discontinuous liquid deposition technique. In one embodiment, the buffer layer is applied by spin coating. In one embodiment, the buffer layer is applied by ink jet printing. After liquid deposition, the liquid medium can be removed in air, in an inert atmosphere, or by vacuum, at room temperature or with heating. In one embodiment, the layer is heated to a temperature less than 275° C. In one embodiment, the heating temperature is between 100° C. and 275° C. In one embodiment, the heating temperature is between 100° C. and 120° C. In one embodiment, the heating temperature is between 120° C. and 140° C. In one embodiment, the heating temperature is between 140° C. and 160° C. In one embodiment, the heating temperature is between 160° C. and 180° C. In one embodiment, the heating temperature is between 180° C. and 200° C. In one embodiment, the heating temperature is between 200° C. and 220° C. In one embodiment, the heating temperature is between 190° C. and 220° C. In one embodiment, the heating temperature is between 220° C. and 240° C. In one embodiment, the heating temperature is between 240° C. and 260° C. In one embodiment, the heating temperature is between 260° C. and 275° C. The heating time is dependent upon the temperature, and is generally between 5 and 60 minutes. In one embodiment, the final layer thickness is between 5 and 200 nm. In one embodiment, the final layer thickness is between 5 and 40 nm. In one embodiment, the final layer thickness is between 40 and 80 nm. In one embodiment, the final layer thickness is between 80 and 120 nm. In one embodiment, the final layer thickness is between 120 and 160 nm. In one embodiment, the final layer thickness is between 160 and 200 nm.

The hole transport layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic liquid is selected from chloroform, dichloromethane, toluene, anisole, and mixtures thereof. The hole transport material can be present in the liquid medium in a concentration of 0.2 to 2 percent by weight. Other weight percentages of hole transport material may be used depending upon the liquid medium. The hole transport layer can be applied by any continuous or discontinuous liquid deposition technique. In one embodiment, the hole transport layer is applied by spin coating. In one embodiment, the hole transport layer is applied by ink jet printing. After liquid deposition, the liquid medium can be removed in air, in an inert atmosphere, or by vacuum, at room temperature or with heating. In one embodiment, the layer is heated to a temperature of 300° C. or less. In one embodiment, the heating temperature is between 170° C. and 275° C. In one embodiment, the heating temperature is between 170° C. and 200° C. In one embodiment, the heating temperature is between 190° C. and 220° C. In one embodiment, the heating temperature is between 210° C. and 240° C. In one embodiment, the heating temperature is between 230° C. and 270° C. The heating time is dependent upon the temperature, and is generally between 5 and 60 minutes. In one embodiment, the final layer thickness is between 5 and 50 nm. In one embodiment, the final layer thickness is between 5 and 15 nm. In one embodiment, the final layer thickness is between 15 and 25 nm. In one embodiment, the final layer thickness is between 25 and 35 nm. In one embodiment, the final layer thickness is between 35 and 50 nm.

The photoactive layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic liquid is selected from chloroform, dichloromethane, toluene, anisole, and mixtures thereof. The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In one embodiment, the photoactive layer is applied by spin coating. In one embodiment, the photoactive layer is applied by ink jet printing. After liquid deposition, the liquid medium can be removed in air, in an inert atmosphere, or by vacuum, at room temperature or with heating. In one embodiment, the deposited layer is heated to a temperature that is less than the Tg of the material having the lowest Tg. In one embodiment, the heating temperature is at least 10° C. less than the lowest Tg. In one embodiment, the heating temperature is at least 20° C. less than the lowest Tg. In one embodiment, the heating temperature is at least 30° C. less than the lowest Tg. In one embodiment, the heating temperature is between 50° C. and 150° C. In one embodiment, the heating temperature is between 50° C. and 75° C. In one embodiment, the heating temperature is between 75° C. and 100° C. In one embodiment, the heating temperature is between 100° C. and 125° C. In one embodiment, the heating temperature is between 125° C. and 150° C. The heating time is dependent upon the temperature, and is generally between 5 and 60 minutes. In one embodiment, the final layer thickness is between 25 and 100 nm. In one embodiment, the final layer thickness is between 25 and 40 nm. In one embodiment, the final layer thickness is between 40 and 65 nm. In one embodiment, the final layer thickness is between 65 and 80 nm. In one embodiment, the final layer thickness is between 80 and 100 nm.

The electron transport layer can be deposited by any vapor deposition method. In one embodiment, it is deposited by thermal evaporation under vacuum. In one embodiment, the final layer thickness is between 1 and 100 nm. In one embodiment, the final layer thickness is between 1 and 15 nm. In one embodiment, the final layer thickness is between 15 and 30 nm. In one embodiment, the final layer thickness is between 30 and 45 nm. In one embodiment, the final layer thickness is between 45 and 60 nm. In one embodiment, the final layer thickness is between 60 and 75 nm. In one embodiment, the final layer thickness is between 75 and 90 nm. In one embodiment, the final layer thickness is between 90 and 100 nm.

The electron injection layer can be deposited by any vapor deposition method. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. All vapor deposition rates given herein are in units of Angstroms per second. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 0.1 and 3 nm. In one embodiment, the final layer thickness is between 0.1 and 1 nm. In one embodiment, the final layer thickness is between 1 and 2 nm. In one embodiment, the final layer thickness is between 2 and 3 nm.

The cathode can be deposited by any vapor deposition method. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 10 and 10000 nm. In one embodiment, the final layer thickness is between 10 and 1000 nm. In one embodiment, the final layer thickness is between 10 and 50 nm. In one embodiment, the final layer thickness is between 50 and 100 nm. In one embodiment, the final layer thickness is between 100 and 200 nm. In one embodiment, the final layer thickness is between 200 and 300 nm. In one embodiment, the final layer thickness is between 300 and 400 nm. In one embodiment, the final layer thickness is between 400 and 500 nm. In one embodiment, the final layer thickness is between 500 and 600 nm. In one embodiment, the final layer thickness is between 600 and 700 nm. In one embodiment, the final layer thickness is between 700 and 800 nm. In one embodiment, the final layer thickness is between 800 and 900 nm. In one embodiment, the final layer thickness is between 900 and 1000 nm. In one embodiment, the final layer thickness is between 1000 and 2000 nm. In one embodiment, the final layer thickness is between 2000 and 3000 nm. In one embodiment, the final layer thickness is between 3000 and 4000 nm. In one embodiment, the final layer thickness is between 4000 and 5000 nm. In one embodiment, the final layer thickness is between 5000 and 6000 nm. In one embodiment, the final layer thickness is between 6000 and 7000 nm. In one embodiment, the final layer thickness is between 7000 and 8000 nm. In one embodiment, the final layer thickness is between 8000 and 9000 nm. In one embodiment, the final layer thickness is between 9000 and 10000 nm.

In one embodiment, the device is fabricated by vapor deposition of the buffer layer, the hole transport layer, and the photoactive layer, the electron transport layer, the electron injection layer, and the cathode.

In one embodiment, the buffer layer is applied by vapor deposition. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 5 and 200 nm. In one embodiment, the final layer thickness is between 5 and 30 nm. In one embodiment, the final layer thickness is between 30 and 60 nm. In one embodiment, the final layer thickness is between 60 and 90 nm. In one embodiment, the final layer thickness is between 90 and 120 nm. In one embodiment, the final layer thickness is between 120 and 150 nm. In one embodiment, the final layer thickness is between 150 and 280 nm. In one embodiment, the final layer thickness is between 180 and 200 nm.

In one embodiment, the hole transport layer is applied by vapor deposition. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 5 and 200 nm. In one embodiment, the final layer thickness is between 5 and 30 nm. In one embodiment, the final layer thickness is between 30 and 60 nm. In one embodiment, the final layer thickness is between 60 and 90 nm. In one embodiment, the final layer thickness is between 90 and 120 nm. In one embodiment, the final layer thickness is between 120 and 150 nm. In one embodiment, the final layer thickness is between 150 and 280 nm. In one embodiment, the final layer thickness is between 180 and 200 nm.

In one embodiment, the photoactive layer is applied by vapor deposition. In one embodiment, it is deposited by thermal evaporation under vacuum. In one embodiment, the photoactive layer consists essentially of a single electroluminescent compound, which is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 5 and 200 nm. In one embodiment, the final layer thickness is between 5 and 30 nm. In one embodiment, the final layer thickness is between 30 and 60 nm. In one embodiment, the final layer thickness is between 60 and 90 nm. In one embodiment, the final layer thickness is between 90 and 120 nm. In one embodiment, the final layer thickness is between 120 and 150 nm. In one embodiment, the final layer thickness is between 150 and 280 nm. In one embodiment, the final layer thickness is between 180 and 200 nm.

In one embodiment, the photoactive layer comprises two electroluminescent materials, each of which is applied by thermal evaporation under vacuum. Any of the above listed vacuum conditions and temperatures can be used. Any of the above listed deposition rates can be used. The relative deposition rates can be from 50:1 to 1:50. In one embodiment, the relative deposition rates are from 1:1 to 1:3. In one embodiment, the relative deposition rates are from 1:3 to 1:5. In one embodiment, the relative deposition rates are from 1:5 to 1:8. In one embodiment, the relative deposition rates are from 1:8 to 1:10. In one embodiment, the relative deposition rates are from 1:10 to 1:20. In one embodiment, the relative deposition rates are from 1:20 to 1:30. In one embodiment, the relative deposition rates are from 1:30 to 1:50. The total thickness of the layer can be the same as that described above for a single-component photoactive layer.

In one embodiment, the photoactive layer comprises one electroluminescent material and at least one host material, each of which is applied by thermal evaporation under vacuum. Any of the above listed vacuum conditions and temperatures can be used. Any of the above listed deposition rates can be used. The relative deposition rate of electroluminescent material to host can be from 1:1 to 1:99. In one embodiment, the relative deposition rates are from 1:1 to 1:3. In one embodiment, the relative deposition rates are from 1:3 to 1:5. In one embodiment, the relative deposition rates are from 1:5 to 1:8. In one embodiment, the relative deposition rates are from 1:8 to 1:10. In one embodiment, the relative deposition rates are from 1:10 to 1:20. In one embodiment, the relative deposition rates are from 1:20 to 1:30. In one embodiment, the relative deposition rates are from 1:30 to 1:40. In one embodiment, the relative deposition rates are from 1:40 to 1:50. In one embodiment, the relative deposition rates are from 1:50 to 1:60. In one embodiment, the relative deposition rates are from 1:60 to 1:70. In one embodiment, the relative deposition rates are from 1:70 to 1:80. In one embodiment, the relative deposition rates are from 1:80 to 1:90. In one embodiment, the relative deposition rates are from 1:90 to 1:99. The total thickness of the layer can be the same as that described above for a single-component photoactive layer.

In one embodiment, the electron transport layer is applied by vapor deposition. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C.; 150° C. to 350° C. preferably. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 5 and 200 nm. In one embodiment, the final layer thickness is between 5 and 30 nm. In one embodiment, the final layer thickness is between 30 and 60 nm. In one embodiment, the final layer thickness is between 60 and 90 nm. In one embodiment, the final layer thickness is between 90 and 120 nm. In one embodiment, the final layer thickness is between 120 and 150 nm. In one embodiment, the final layer thickness is between 150 and 280 nm. In one embodiment, the final layer thickness is between 180 and 200 nm.

In one embodiment, the electron injection layer is applied by vapor deposition, as described above.

In one embodiment, the cathode is applied by vapor deposition, as describe above.

In one embodiment, the device is fabricated by vapor deposition of some of the organic layers, and liquid deposition of some of the organic layers. In one embodiment, the device is fabricated by liquid deposition of the buffer layer, and vapor deposition of all of the other layers Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further described in the following examples, which do not limit the scope of the invention described in the claims.

Example 1

This example illustrates the preparation of an electroactive compound, Compound C.

Part 1—Intermediate Compound 2:

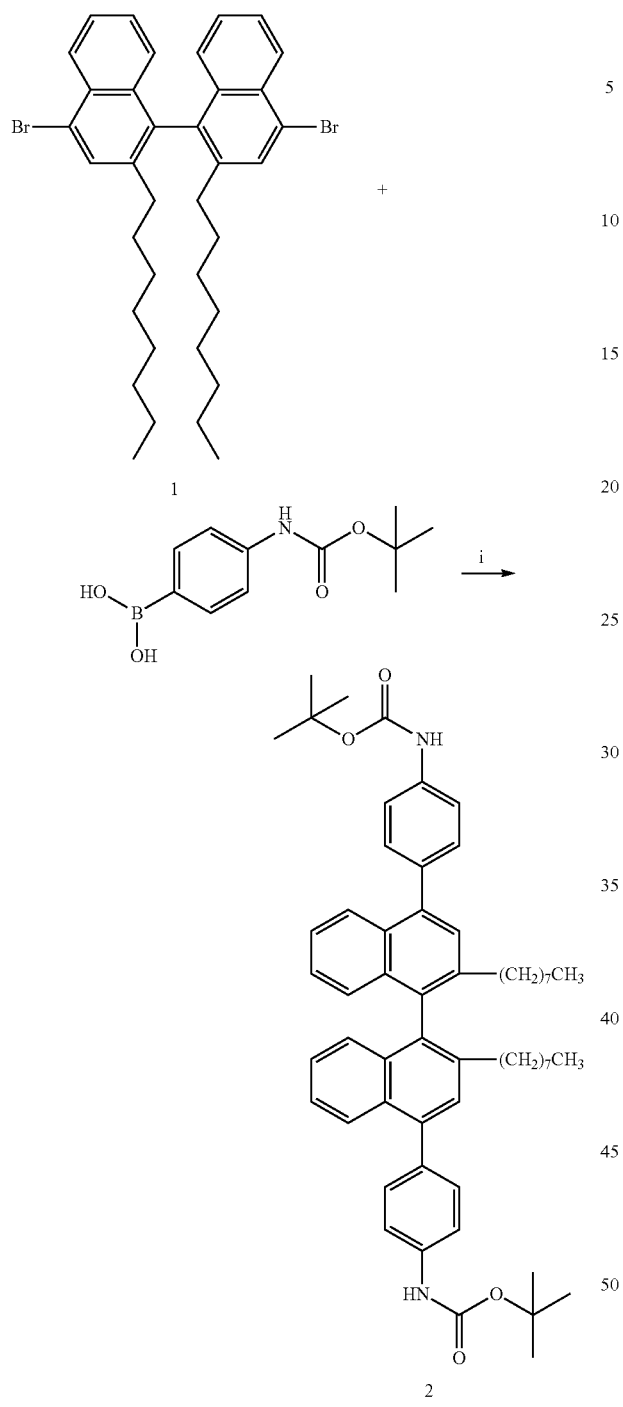

i- 5 mol % (Ph$_3$P)$_4$Pd(0)], Aliquat (R) 336, 1M Na$_2$CO$_3$, toluene, 90° C.

Compound 1 (4.0 g, 6.3 mmol) was dissolved in 60 mL toluene in a 2 neck 200 mL septum-sealed round bottom. 4-[(tert-Butoxycarbonyl)amino]benzeneboronic acid (3.72 g, 15.7 mmol), Aliquat® 336 (0.5 g) and sodium carbonate (3.33 g, 31.4 mmol) were added. The mixture was sparged with nitrogen and the reaction flask was fitted with a reflux condenser and nitrogen inlet-outlet. In a nitrogen purged glovebox, tetrakistriphenylphosphine (363 mg, 5.00 mol %) and anhydrous toluene (10 mL) were combined in a round bottom flask. The flask was sealed with a septum and removed from the glovebox. The catalyst suspension was added to the reaction mixture via a cannula. Water (30 mL) was added to the reaction vessel via syringe. The nitrogen sparge was removed and replaced with a nitrogen blanket. The reaction mixture was heated at 90° C. for 3 h. The reaction was allowed to cool to room temperature, transferred to a separatory funnel and diluted with ethyl acetate. The aqueous layer was removed and the organic layer was washed with water, then with brine and dried over MgSO$_4$. The crude product was filtered through a pad of silica gel, rinsing with ethyl acetate. The solvent was removed and the product was dried under high vacuum. After purification by flash column chromatography (3:2 hexanes:methylene chloride), 2.2 g of a light orange foamy solid was obtained. Purity (HPLC): 98.5%, pure 4,4' isomer. NMR analysis confirmed the structure of Intermediate Compound 2.

Part 2—Intermediate Compound 3:

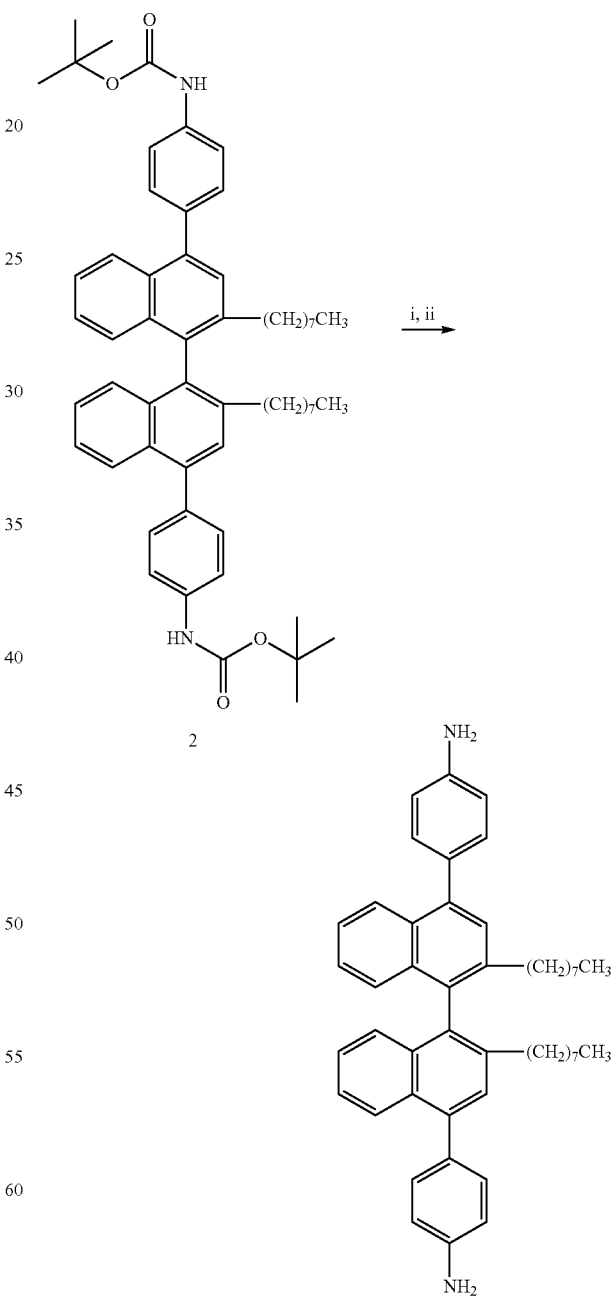

Conditions: i- TFA, CH$_2$Cl$_2$; ii- 10% NaHCO$_3$

Intermediate Compound 2 (2.2 g, 2.5 mmol) was dissolved in 40 mL methylene chloride in a 250 mL round bottom flask equipped with a magnetic stirrer and a nitrogen inlet-outlet. Trifluoroacetic acid (2.9 g, 25 mmol) was added and the reaction was allowed to stir for 16 h. The solvent and trifluoroacetic acid were removed by rotary evaporation and the product was taken up in diethyl ether. The diethyl ether solution was washed with saturated sodium bicarbonate (2×), water and brine. The ether layer was dried over MgSO4, filtered and concentrated on a rotary evaporator. The product was dried under high vacuum to yield 1.7 g (100%) of a light orange foamy solid. Purity (HPLC): 94.7%. NMR analysis confirmed the structure of Intermediate Compound 3.

Part 3—Intermediate Compound 4:

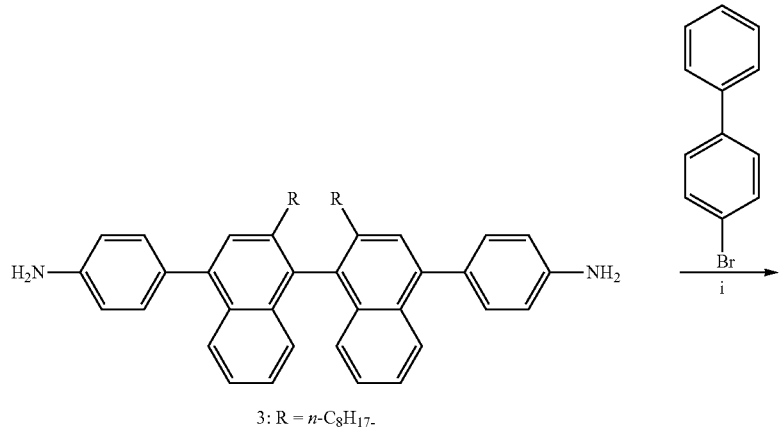

3: R = n-C$_8$H$_{17}$-

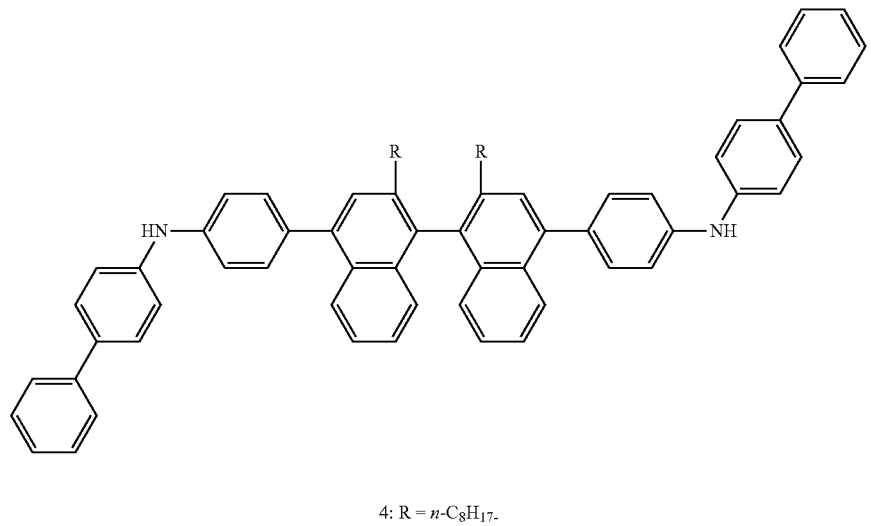

4: R = n-C$_8$H$_{17}$-

Conditions: i- Pd$_2$dba$_3$, t-Bu$_3$P, NaOBu$^t$, toluene, rt

In a nitrogen purged glovebox, combined 3 (1.60 g, 2.42 mmol), 4-bromobiphenyl (1.13 g, 4.84 mmol), tris(dibenzylideneacetone)dipalladium(0) (55 mg, 2.5 mol %), tri-t-butylphosphine (25 mg, 5 mol %) and toluene (30 mL) in a 500 mL round bottom flask equipped with a magnetic stirrer. Sodium t-butoxide (0.58 g, 6.05 mmol) was added and the reaction flask was capped. After 72 h, the reaction mixture was removed from the glovebox and filtered through a pad of solica gel, rinsing with toluene. The solution was concentrated on a rotary evaporator and dried under high vacuum. The product was purified by flash chromatography on silica gel (7:3 to 3:2 hexanes:methylene chloride gradient) to give 1.56 g of a white solid. NMR analysis confirmed the structure of Intermediate Compound 4.

Part 5—Intermediate Compound 5.

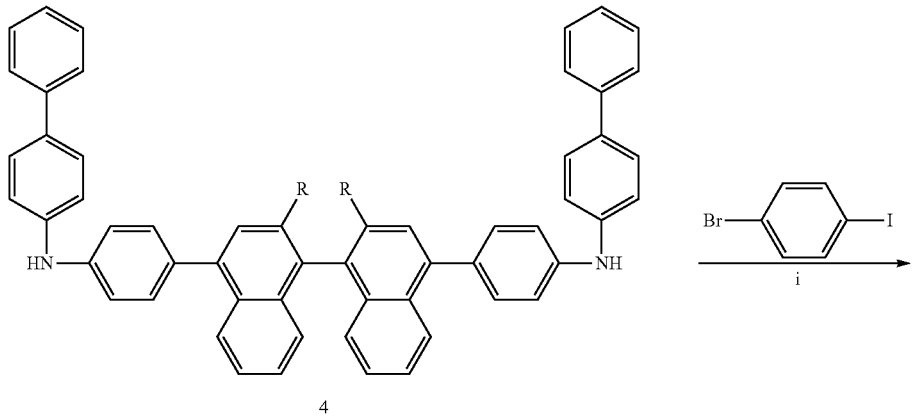

R = n-C$_8$H$_{17}$-

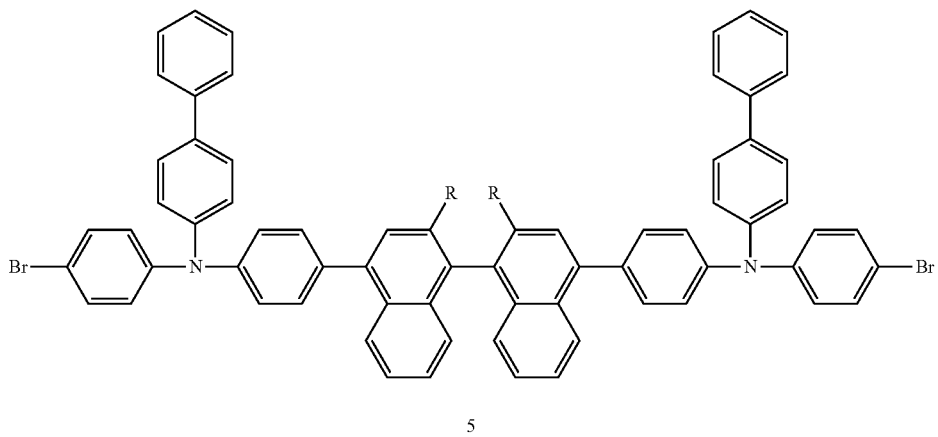

Conditions: i- Pd$_2$dba$_3$, (dppf)$_2$, NaOBu$^t$, toluene, 80° C.

In a nitrogen purged glovebox, combined 4 (1.50 g, 1.55 mmol), p-bromoiodobenzene (1.32 g, 4.66 mmol), tris(dibenzylideneacetone)dipalladium(0) (36 mg, 2.5 mol %), bis(diphenylphosphinoferrocene) (43 mg, 5 mol %) and toluene (60 mL) in a 300 mL round bottom flask equipped with a magnetic stirrer. Sodium t-butoxide (0.373 g, 3.88 mmol) was added and the reaction vessel was capped and removed from the glovebox. A condenser and nitrogen inlet-outlet was fitted to the round bottom flask and the reaction was heated to 85° C. with an oil bath. After 20 h, a suspension of p-bromoiodobenzene (0.66 g, 2.3 mmol), tris(dibenzylideneacetone)dipalladium(0) (18 mg, 1.25 mol %), bis(diphenylphosphino)ferrocene (21 mg, 2.5 mol %) and sodium t-butoxide (186 mg, 1.25 mol %) in toluene (10 mL) was prepared in the glovebox and transferred to the reaction mixture via cannula. After additional 20 h at 90° C., the reaction mixture was cooled to room temperature. The reaction mixture was filtered through a pad of silica gel rinsing with toluene and then concentrated on a rotary evaporator. The crude product was dried under high vacuum. The product was purified by flash chromatography on silica gel (6:1-5:1 hexanes:methylene chloride gradient) to give 1.4 g of a white solid. Purity (UPLC): >99.9%. NMR analysis confirmed the structure of Intermediate Compound 5.

Part 6—Compound C:

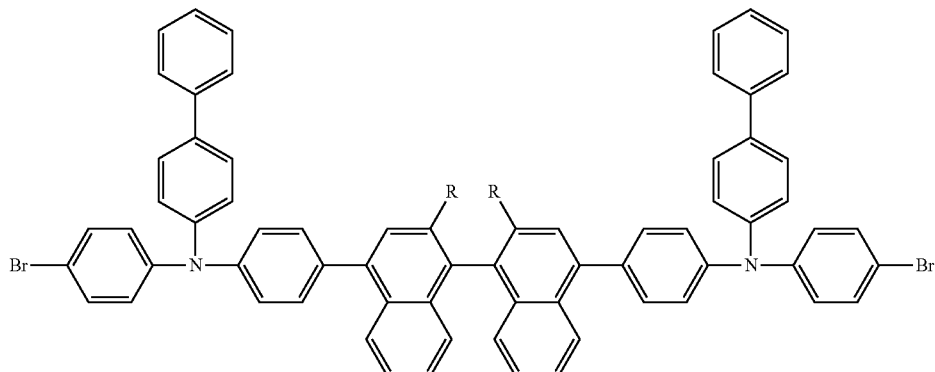

5

↓i

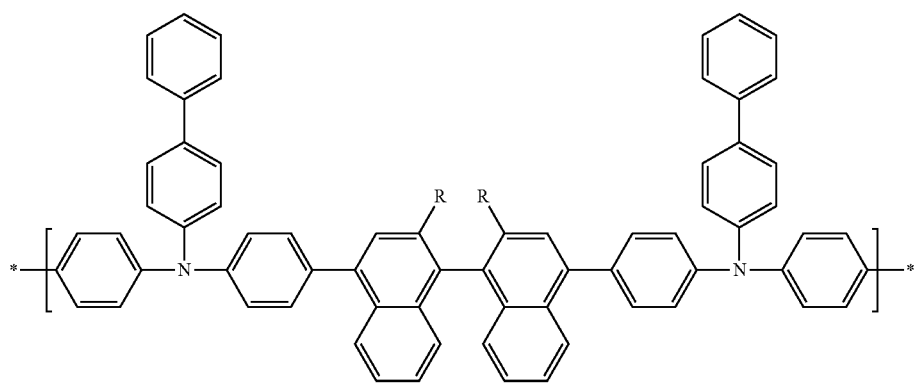

6

R = CH₃(CH₂)₇-

Conditions: i- Ni(COD)₂, COD, dipyridyl, 13:2 toluene:DMF, 70° C.

All operations were carried out in a nitrogen purged glovebox unless otherwise noted. Monomer 5 (1.35 g, 1.06 mmol) was added to a scintillation vial and dissolved in 13 mL toluene. A clean, dry 50 mL Schlenk tube was charged with bis(1,5-cyclooctadiene)nickel(0) (0.597 g, 2.17 mmol). 2,2'-Dipyridyl (0.339 g, 2.17 mmol) and 1,5-cyclooctadiene (0.235 g, 2.02 mmol) were weighed into a scintillation vial and dissolved in 2 mL N,N'-dimethylformamide. The solution was added to the Schlenk tube. The Schlenk tube was inserted into an aluminum block and the block was heated and stirred on a hotplate/stirrer at a setpoint that resulted in an internal temperature of 60° C. The catalyst system was held at 60° C. for 30 minutes and then raised to 70° C. The monomer solution in toluene was added to the Schlenk tube and the tube was sealed. The polymerization mixture was stirred at 70° C. for 18 h. After 18 h, the Schlenk tube was removed from the block and allowed to cool to room temperature. The tube was removed from the glovebox and the contents were poured into a solution of conc. HCl/MeOH (1.5% v/v conc. HCl). After stirring for 2 h, the polymer was collected by vacuum filtration and dried under high vacuum. The polymer was purified by successive precipitations from toluene into HCl/MeOH (1% v/v conc. HCl), MeOH, toluene (CMOS grade), and 3-pentanone. A white, fibrous polymer (1.1 g) was obtained. The molecular weight of the polymer was determined by GPC (THF mobile phase, polystyrene standards): $M_w$=427,866; $M_n$=103,577; $M_w/M_n$=4.13. NMR analysis confirmed the structure of Compound C.

Example 2
Synthesis of Compound S
Part 1—Synthesis of Intermediate Compound 7:
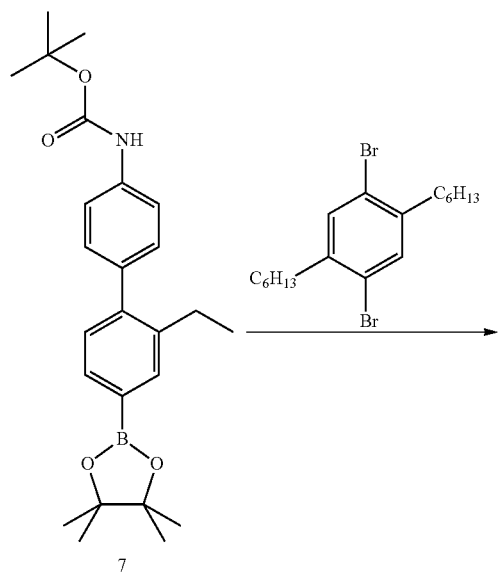
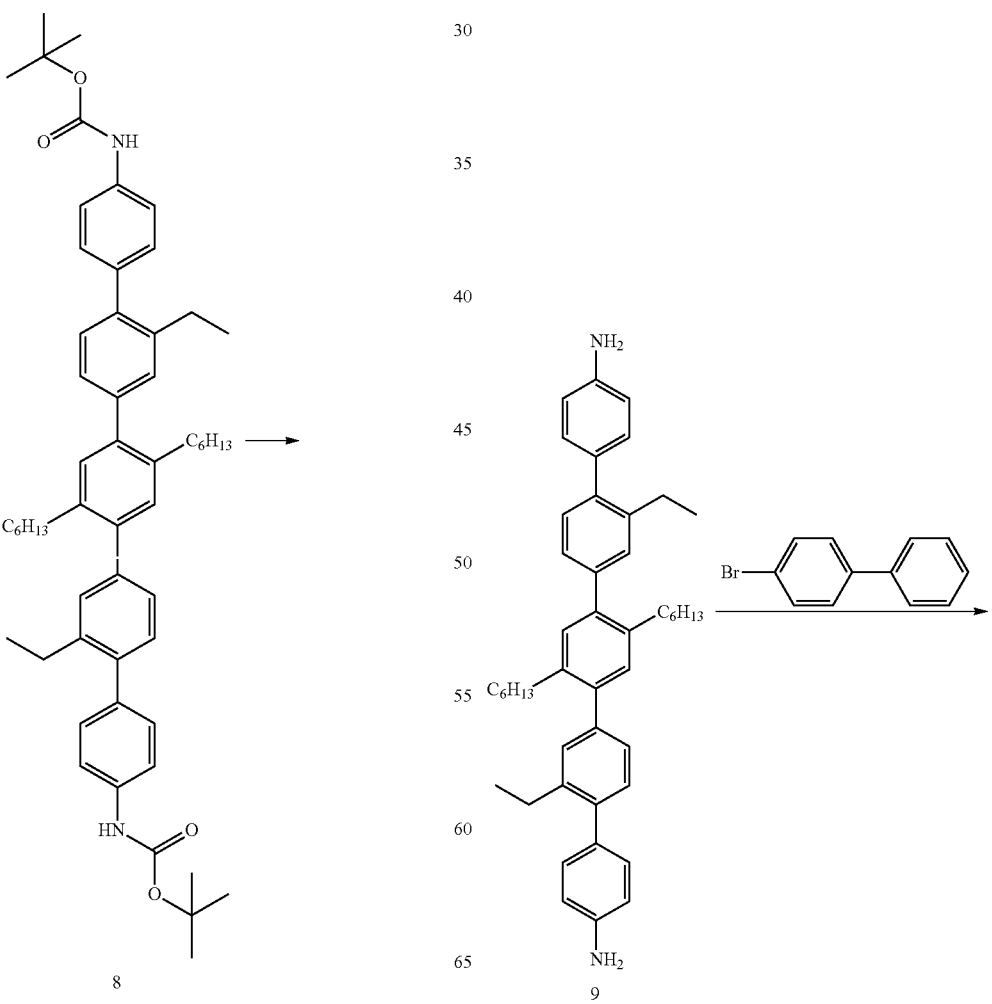
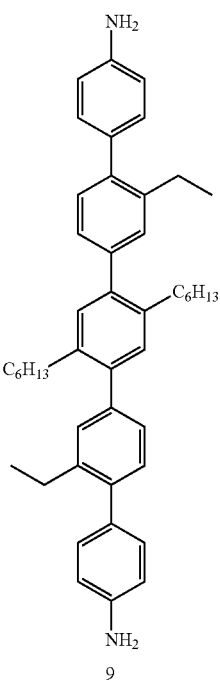

51
-continued
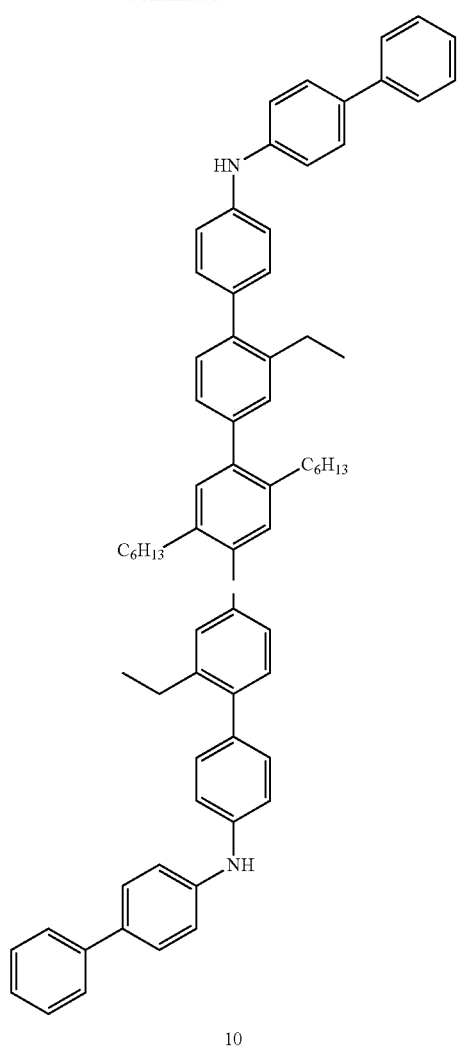
10
52
-continued
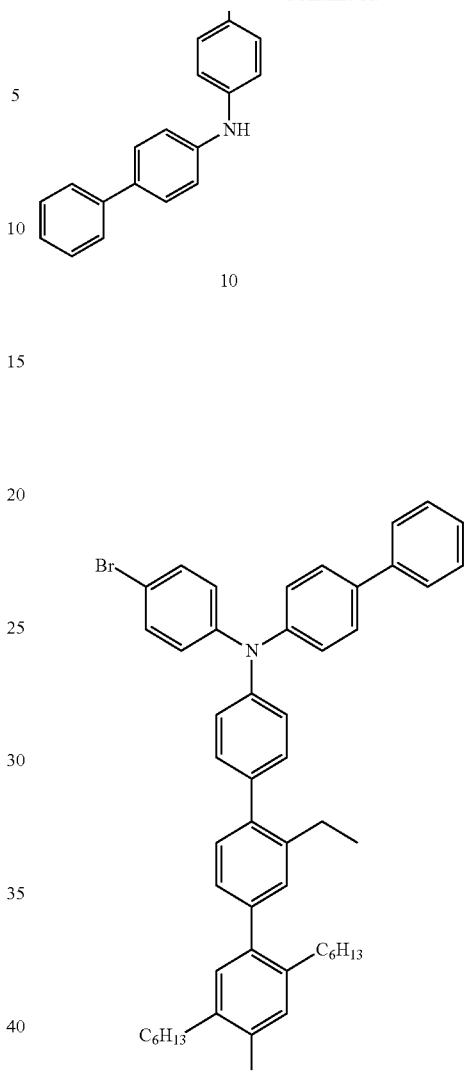
10
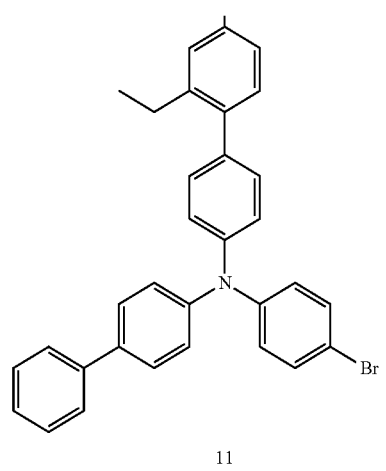
11

-continued

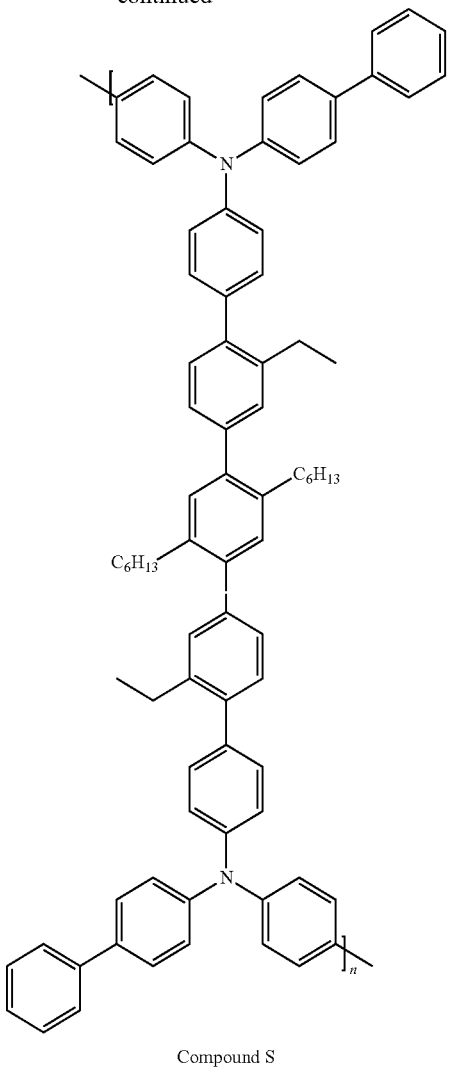

Compound S

Part 2: Synthesis of Intermediate Compound 8

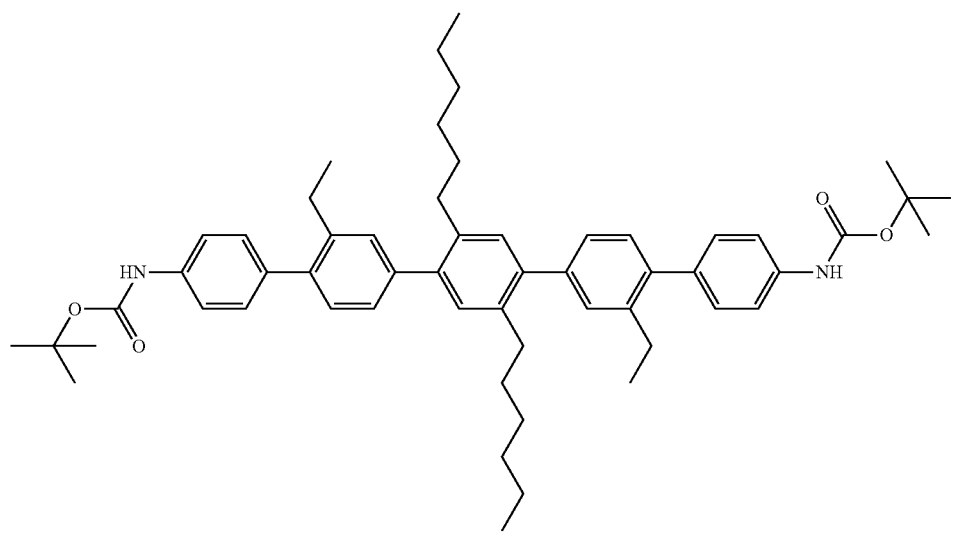

1,4-dibromo-2,5-dihexyl benzene (8.05 mmoles, 3.255 g), boronic ester 7 (17.7 mmoles, 7.545 g), Na$_2$CO$_3$ (40.3 mmoles, 4.268 g) and Aliquat 336 (0.500 g) were suspended in toluene (100 mL) in a 250 mL two-necked-round-bottom-flask with stir bar and condenser. Reaction mixture degassed for 30 minutes. Pd(PPh$_3$)$_4$ (0.403 mmoles, 0.465 g) added as a powder to reaction mixture. Reaction mixture degassed for a further 15 minutes, whilst simultaneously degassing water (50 mL). Water added via syringe to reaction vessel. Reaction heated to 90° C. for two days. Resulting reaction mixture diluted with ethyl acetate (150 mL), washed with ethyl acetate (3×100 mL). Organic layer washed with brine (2×100 mL), dried over magnesium sulfate, filtered and concentrated. Purification by column chromatography on silica gel using 1:3 dichloromethane: Hexanes to yield white powder (56%, 3.8 g). $^1$H NMR (500 MHz, CD$_2$Cl$_2$) δ=7.45 (d, J=8.5 Hz, 4H), 7.33-7.31 (m, 5H), 7.26-7.19 (m, 5H), 6.65 (s, 2H), 2.71-2.63 (m, 9H), 1.54 (s, 18H), 1.31-1.20 (m, 14H), 1.15 (t, J=7.49, 7H), 0.83 (t, J=6.85 Hz, 6H).

Part 3: Synthesis of Intermediate Compound 9

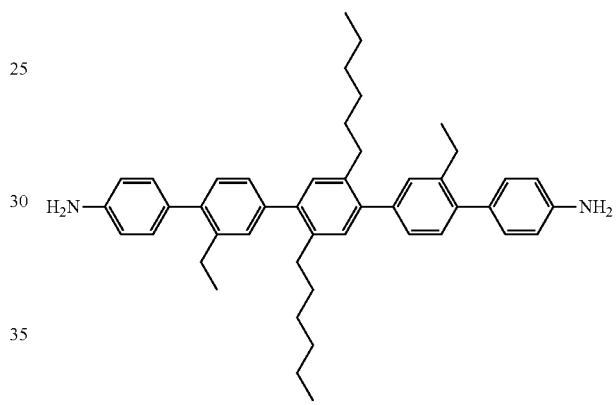

Compound 8 (4.54 mmoles, 3.800 g) was added to 200 mL round bottom flask and dissolved in dichloromethane (90 mL). Trifluoroacetic acid (45.4 mmoles, 5.175 g) added dropwise to the solution. After one day dichloromethane removed by rotary evaporation and the resulting grey powder dissolved in ethyl ether (100 mL) to which sodium bicarbonate was added (100 mL). The organic layer was washed with water (2×100 mL), followed by brine (2×100 mL). After it was dried over magnesium sulfate and concentrated to yield an off white powder (100%, 2.891 g). $^1$H NMR (500 MHz, CD$_2$Cl$_2$) δ=7.28 (m, 2H), 7.23-7.18 (m, 6H), 7.16 (d, J=8.47 Hz, 4H), 6.76 (d, J=8.37 Hz, 4H), 3.77 (s, 4H), 2.71-2.63 (m, 6H), 1.3-1.19 (m, 16H), 1.15 (t, J=7.5 Hz, 8H), 0.83 (t, J=6.86 Hz, 6H).

Part 4: Synthesis of Intermediate Compound 10

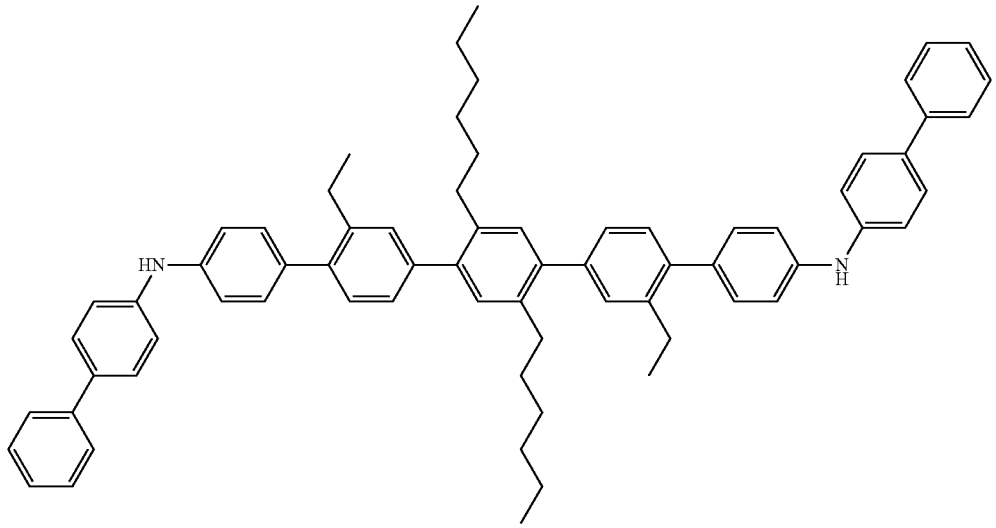

In a 250 mL flask equipped with stirrer bar compound 9 (4.539 mmoles, 2.891 g), bromobiphenyl (9.123 mmoles, 2.127 g) and toluene (65 mL) were added, followed by Pd$_2$(dba)$_3$ (0.227 mmole, 0.208 g), P$^t$Bu3 (0.454 mmole, 0.092 g) and NaO$^t$Bu (9.078 mmoles, 0.845 g). Three days later the resulting reaction mixture was diluted with toluene (100 mL), filtered through a pad of silica and celite washed with toluene (3×100 mL), followed by ethyl acetate (2×100 mL) and concentrated to a brown solid. Purification was performed by column chromatography on silica gel using eluent 1:6 Ethyl acetate:Hexanes, to yield a white powder (55%, 2.367 g). $^1$H NMR (500 MHz, CD$_2$Cl$_2$) δ=7.61 (d, J=7.24 Hz, 4H), 7.57 (d, J=8.51 Hz, 4H), 7.43 (t, J=7.6 Hz, 4H), 7.34-7.28 (m, 12H), 5.99 (s, 2H), 2.73 (q, J=Hz, 4H), 2.66 (t, J=7.7 Hz, 6H), 1.33-1.17 (m, 20H), 0.84 (t, J=7.2 Hz, 6H).

Part 5: Synthesis of Intermediate Compound 11

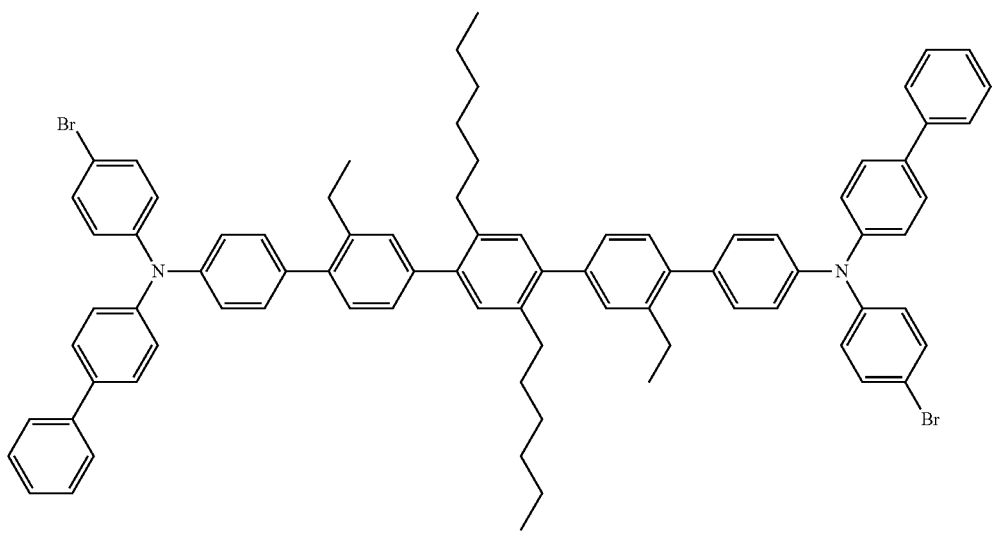

Compound 10 (2.515 mmoles, 2.367 g), 1-bromo-4-iodo benzene (3.772 mmoles, 1.067 g), Pd$_2$(dba)$_3$ (0.126 mmoles, 0.115 g), 1,1-Bis (diphenylphosphino) ferrocene (0.251 mmoles, 0.139 g) and sodium t-butoxide (2.766 mmoles, 0.266 g) were suspended in toluene (100 mL) in a 200 mL two-necked-round-bottom-flask fitted with condenser and stir bar. Reaction mixture heated at 90° C. for two days. The reaction mixture was filtered through a pad of silica and celite, washed with toluene (2×200 mL) and concentrated to form brown solid. Purification by column chromatography on silica gel using 1:2 dichloromethane:hexanes, The product was washed with MeOH to give white powder (23%, 0.715 g). $^1$H NMR (500 MHz, CD$_2$Cl$_2$) δ=7.61 (d, J=6.95 Hz, 4H), 7.56 (d, J=8.73 Hz, 4H), 7.46-7.4 (m, 8H), 7.34-7.29 (m, 10H), 7.24-7.18 (m, 12H), 7.08 (d, J=8.89 Hz, 4H), 2.74 (q, J=7.5 Hz, 4H), 2.65 (t J=8.12 Hz, 6H), 1.32-1.18 (m, 22H), 0.83 (t, J=6.88 Hz, 6H).

Part 6—Polymerization of Compound 11.

The polymerization of compound 11 performed as described for compound C. The polymer was obtained as a white solid. The molecular weight of the polymer was determined by GPC (THF mobile phase, polystyrene standards): $M_w$=140,399; $M_n$=47,692; $M_w/M_n$=2.04. NMR analysis confirmed the structure of Compound S.

Example 3

Synthesis of Compound T

Part 1

Synthesis of intermediate
1-Bromo-4'-(nitrophenyl)naphthalene (12)

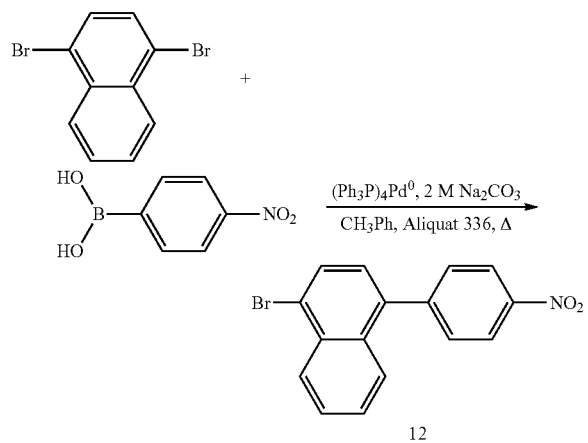

To a 300 ml 2-neck round bottom flask equipped with reflux condenser and nitrogen bubbler were added 1,4-dibromonaphthalene (15.5 g, 54.2 mmol) and 4-nitrophenyl boronic acid (9.05 g, 54.2 mmol). Toluene (175 ml) was added, then 2.0 M aq Na$_2$CO$_3$ (56.9 ml, 113.8 mmol), then Aliquat336® (2.19 g, 5.42 mmol). The mixture was sparged with nitrogen for 1 hour. The reaction was heated under nitrogen for 20 hours and then cooled to room temperature. The mixture was diluted with toluene, washed three times with water and once with brine. The organic layer was dried over MgSO$_4$, filtered, concentrated on a rotary evaporator and dried under high vacuum to give 22 g of brown solid. The crude product was purified by column chromatography (silica gel, 4:1 Hex:CH$_2$Cl$_2$) to isolate 7.9 g white solid. Yield: 40%. $^1$H NMR analysis (500 MHz, CD$_2$Cl$_2$) was consistent with structure 12.

Part 2

Synthesis of intermediate
1-(Aminophenyl)-4'-bromonaphthalene (13)

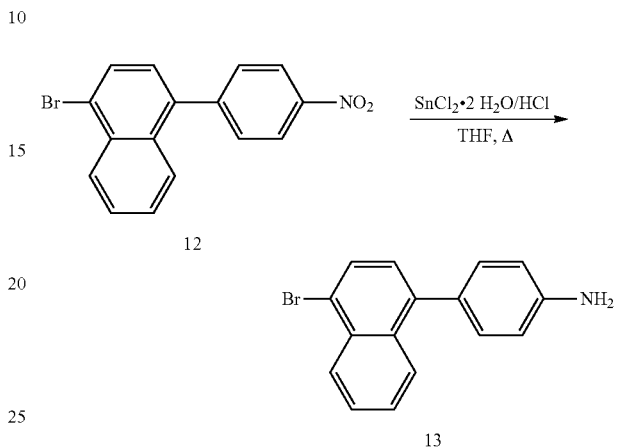

To a 500 ml round-bottom flask equipped with stir bar, reflux condenser, and nitrogen bubbler were added compound 1 (7 g, 20 mmol), THF (170 ml), tin chloride dihydrate (19.25 g, 85.32 mmol), and aqueous 1M HCl (64 ml, 64 mmol). The reaction was heated at reflux under nitrogen for 1 hour, then cooled to room temperature. The mixture was concentrated on a rotary evaporator to remove THF and neutralized with a saturated solution of aq. NaHCO$_3$. The aqueous layer was extracted with diethyl ether (3×). The organic layer was washed with brine, dried over MgSO$_4$, filtered, concentrated on a rotary evaporator and dried under high vacuum to give 4.5 g crude product. The crude product was purified by column chromatography (silica gel, CH$_2$Cl$_2$) to give 4.36 g light-orange solid. Yield: 69%. Purity (GC-MS): 99+%. $^1$H NMR (500 MHz, CD$_2$Cl$_2$) is consistent with product structure.

Part 3

Synthesis of intermediate
1-Bromo-4'-(iodophenyl)naphthalene (14)

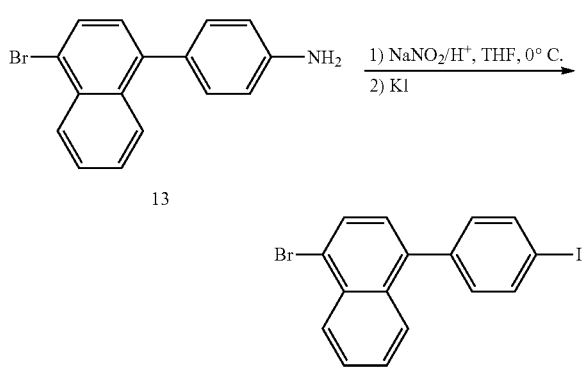

To a 200 ml round-bottom flask equipped with a stir bar and nitrogen bubbler were added compound 2 (3.85 g, 12.9 mmol), THF (65 ml), and aqueous conc. HCl (13 ml). The reaction mixture was cooled in an ice/water bath to 0° C. NaNO$_2$ (1.07 g, 15.5 mmol) in 13 ml H$_2$O was added dropwise and the mixture was stirred with cooling for 25 minutes. KI (4.29 g, 25.8 mmol) in 13 ml H$_2$O was added dropwise. The reaction mixture was warmed slowly to room temperature and stirred for 16 hours. The reaction was diluted with water and extracted with diethyl ether. The organic layer was washed with water, saturated aq. NaHCO$_3$, saturated aq. NaHSO$_3$ and brine. The organic layer was dried over MgSO$_4$, filtered, concentrated on a rotary evaporator and dried under high vacuum to give 4.68 g crude product. The crude product was recrystallized from 1:1 MeOH:ethyl acetate to give 2.53 g light orange solid. Yield: 48%. Purity (GC-MS): 99+%. $^1$H NMR (500 MHz, CD$_2$Cl$_2$) is consistent with product structure.

Part 4

Synthesis of Intermediate Compound 15

Diamine 4 (mixture of 4,4'- and 4,5'-isomers) (1.75 g, 1.81 mmol), 14 (1.85 g, 4.52 mmol), bis(diphenylphosphinoferrocene) (50 mg, 0.91 mmol), tris(dibenzylideneacetone)dipalladium(0) (40 mg, 0.05 mmol), toluene (50 ml) and then sodium t-butoxide (0.44 g, 4.5 mmol) were weighed into a 250 mL round bottom flask in a nitrogen purged glovebox. The reaction vessel was capped, removed from the gloved box and equipped with a reflux condenser and nitrogen bubbler. The reaction was heated at 90° C. for 18 hours. The reaction mixture was filtered through a plug of silica gel, rinsing with dichloromethane. The filtrate was concentrated on a rotary evaporator and dried under high vacuum to give 3.5 g brownish-orange oil. The crude product was purified by column chromatography (3:1 hexanes:CH$_2$Cl$_2$ gradient to 3:2 hexanes:CH$_2$Cl$_2$) to isolate 2.15 g product which was a mixture of 4,4'- and 4,5'-isomers. Yield: 78.2%. $^1$H NMR (500 MHz, CD$_2$Cl$_2$) is consistent with structure of 15.

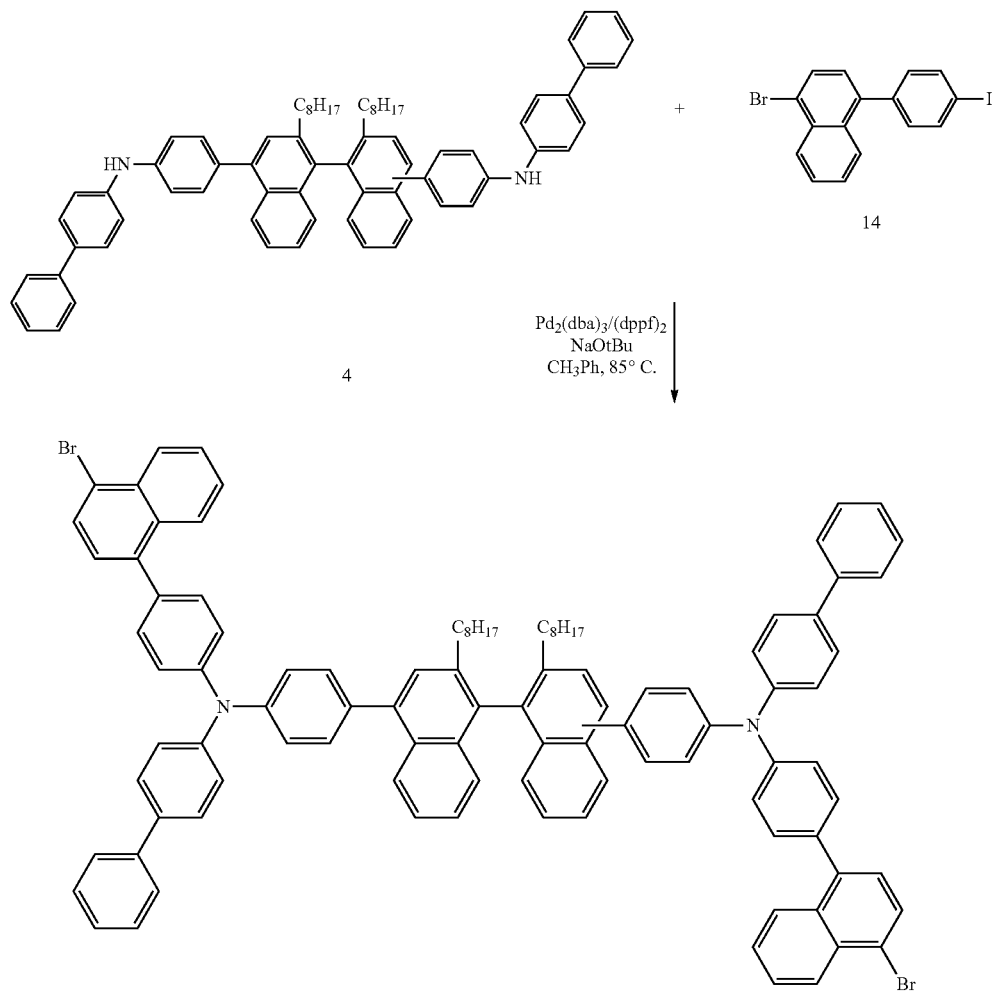

Part 5

Synthesis of Compound T

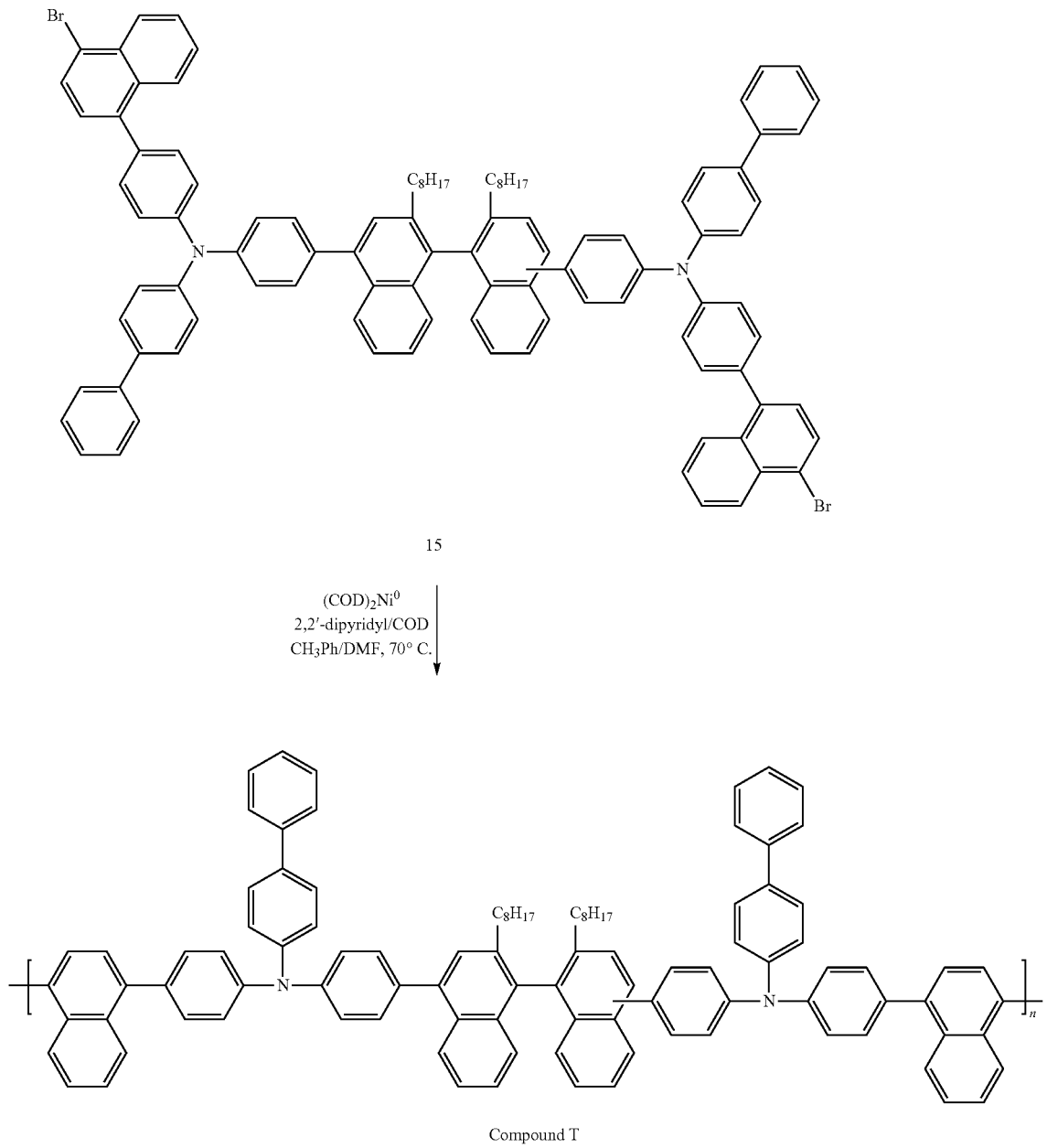

Compound T

The polymerization of 5 was carried out in a nitrogen purged glovebox. Bis(1,5-cyclooctadiene)nickel(0) (0.277 g, 1.01 mmol) was added to a 25 ml Schlenk tube. 2,2′-Dipyridyl (0.157 g, 1.01 mmol) and 1,5-cyclooctadiene (0.109 g, 1.01 mmol) were dissolved in 2 mL DMF. This solution was added to the nickel catalyst. The catalyst solution was stirred and heated in an aluminum block at 60° C. for 30 minutes. The temperature of the heating block was raised to 70° C. Compound 15 (0.750 g, 0.491 mmol) dissolved in toluene (13 mL) and then added to the catalyst solution. The Schlenk tube was sealed and heated for 22 hours and then cooled to room temperature. The reaction tube was removed from the dry box and the contents were poured into 1.5 v/v % HCl/MeOH. The polymer was purified by two precipitations into 1.5 v/v % HCl/MeOH and one precipitation from toluene into MeOH. The polymer was isolated by filtration and then dissolved in toluene. The toluene solution was passed through a plug of silica gel. The filtrate was concentrated and poured into 3-pentanone. The polymer was collected by vacuum filtration, re-dissolved in toluene and passed through a plug of Florisil®. The filtrate was concentrated and precipitated from 3-pentanone. The polymer was isolated by filtration and dried under high vacuum to give 0.52 g white, fibrous polymer. Yield: 77%. Molecular weight determination (GPC, THF, polystyrene standards): $M_w$=296,000; $M_n$=103,000; PDI=2.88.

Example 4
Synthesis of Compound U
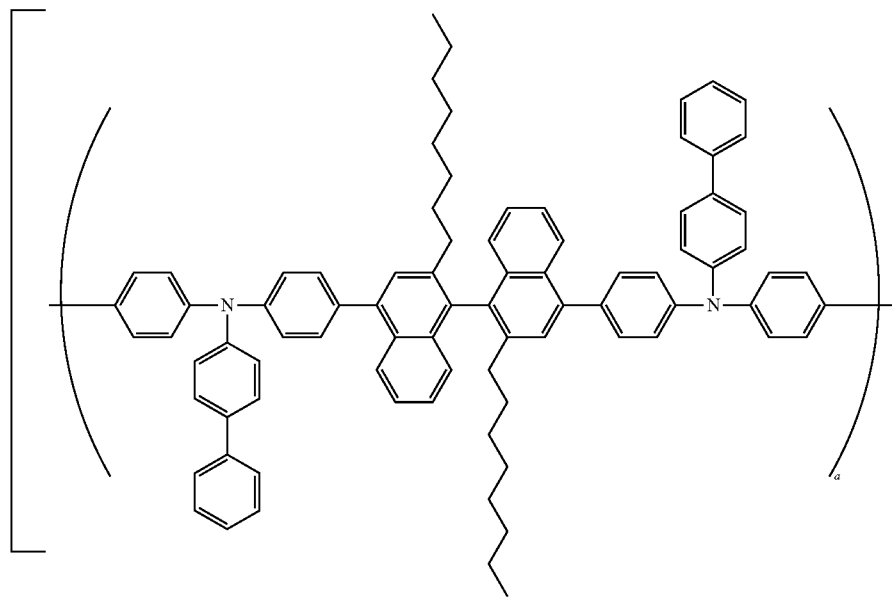
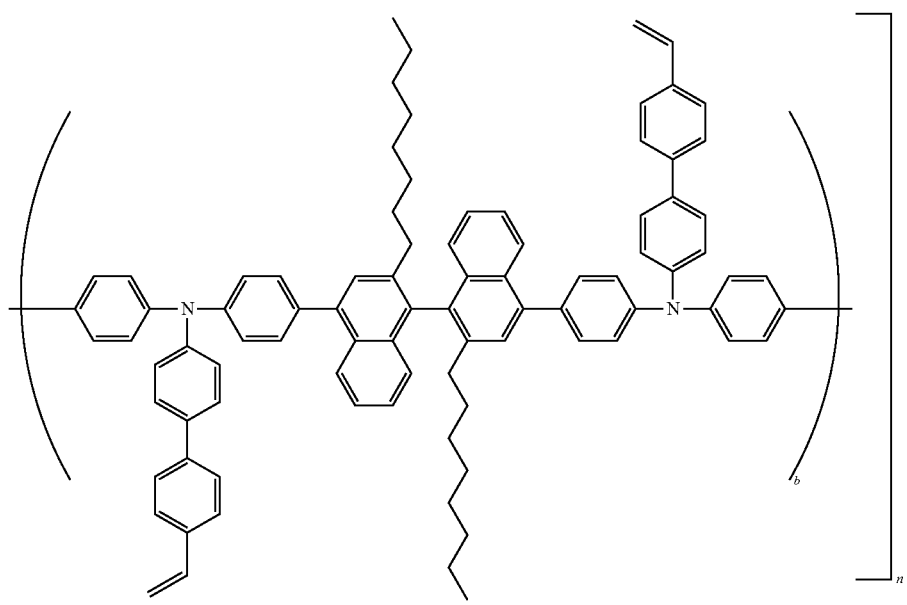
a:b = 95:5

The monomer 16 was synthesized following the procedure outlined for compound 5 except that 4-vinyl-4'-bromobiphenyl was used instead of bromobiphenyl.

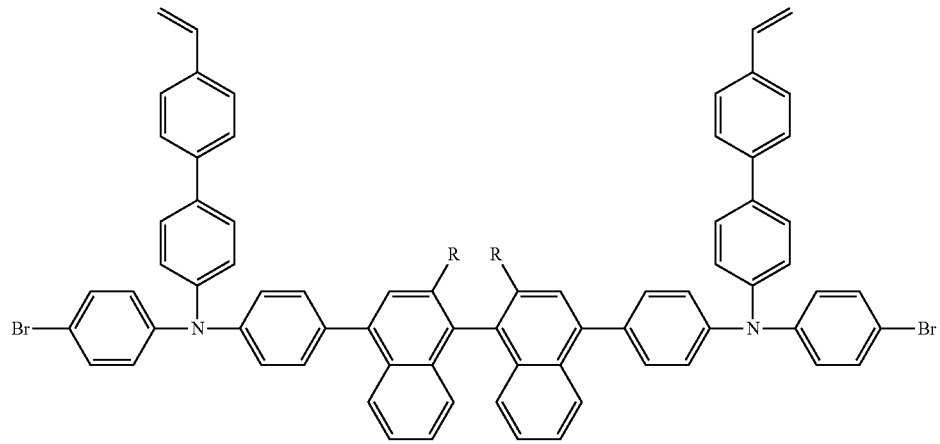

Compounds 5 (0.95 mmol) and 16 (0.05 mmol) were copolymerized following the procedure for the synthesis of compound C to obtain a white fibrous polymer in 86% yield (0.96 g). Molecular weight determination (GPC, THF, polystyrene standards): $M_w$=658,109; $M_n$=105,822; PDI=6.22.

Example 5

Synthesis of Compound V

Compound V was synthesized using the route shown below:

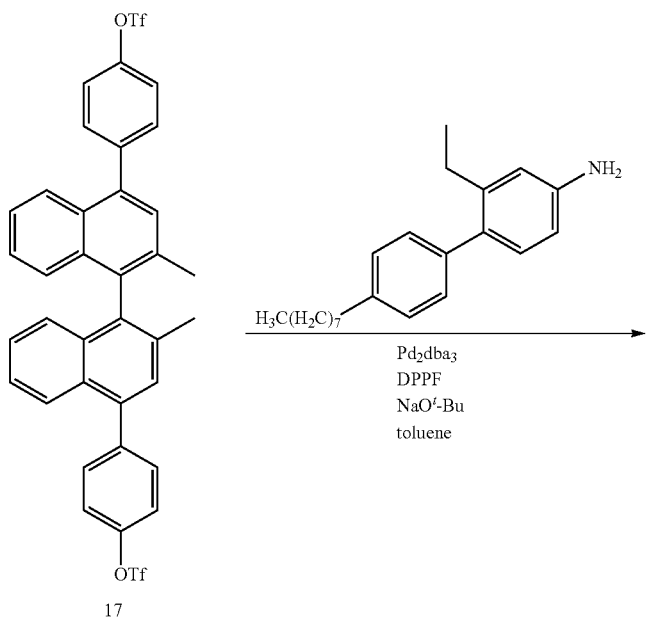

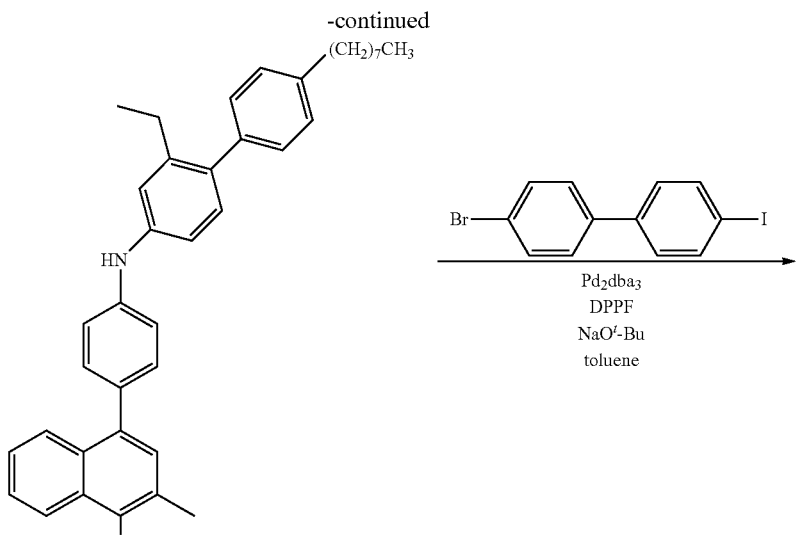
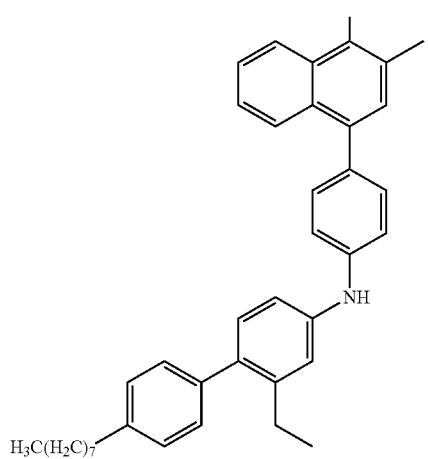
18
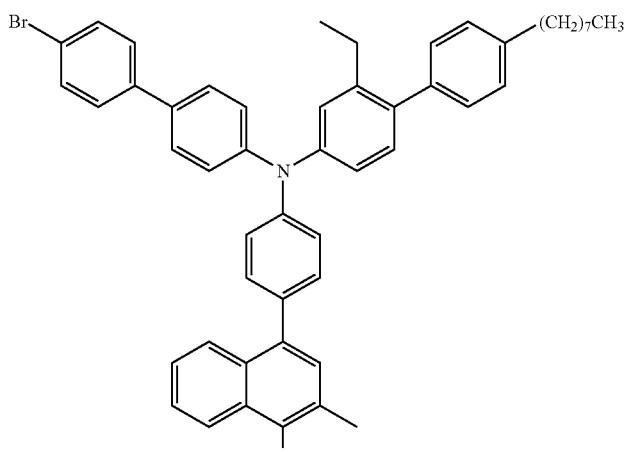

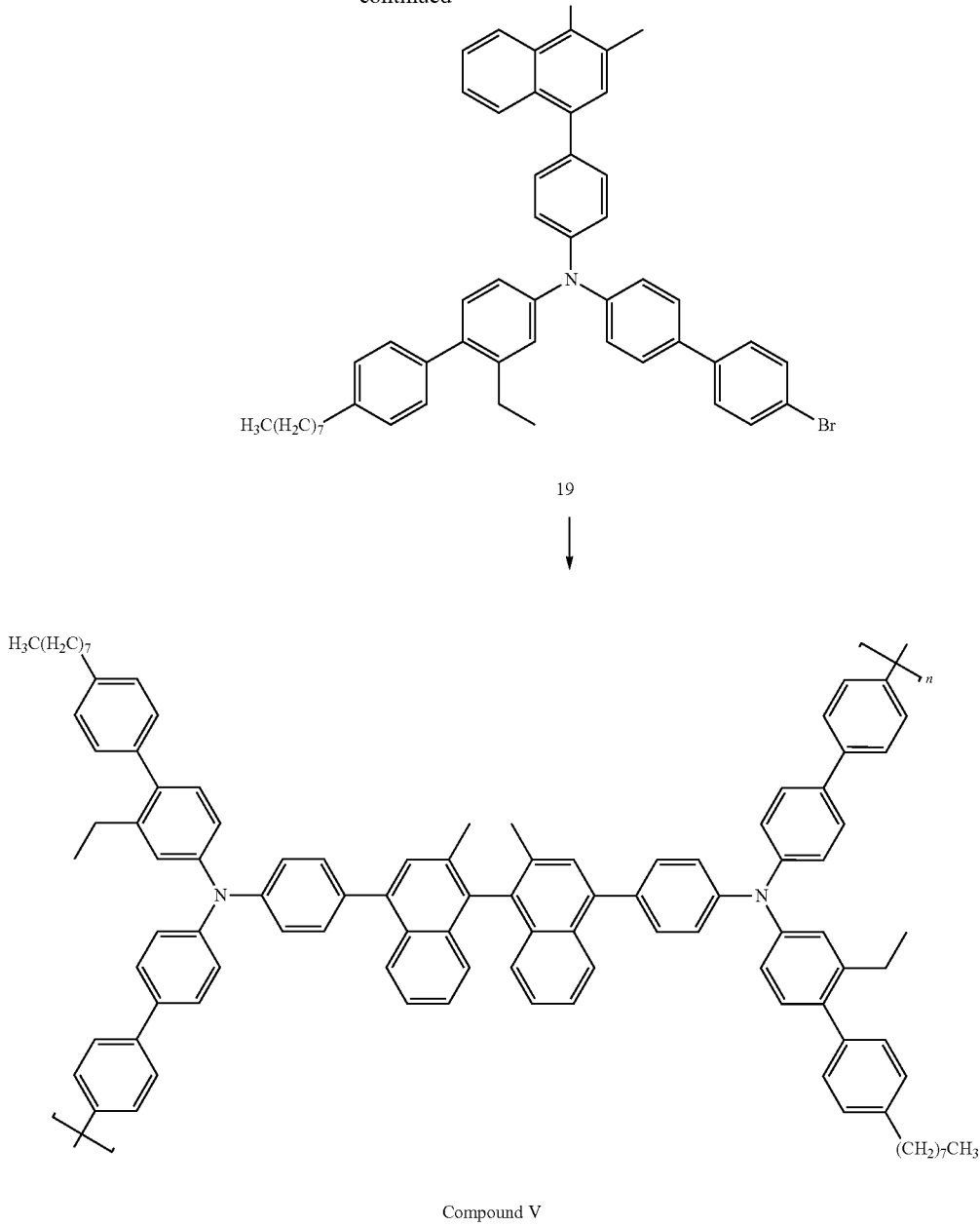

Compound V

Part 1. Synthesis of Intermediate 18:

In a nitrogen purged glove box, ditriflate 17 (3.2 g, 4.38 mmol) and 2-ethyl-4'-octyl-biphen-4-yl-amine (2.84 g, 9.19 mmol) were dissolved in toluene (60 mL) in a 200 mL of round bottom flask, followed by the addition of the toluene (10 mL) solution of tris(dibenzylideneacetone)dipalladium (0) (108 mg, 0.027 eq.) and 1,1'-bis(diphenylphosphino)ferrocene (128 mg, 0.053 eq) to the mixture. After stirring the mixture for 5 min, sodium t-butoxide (1.05 g, 10.94 mmol, 2.5 eq) was added to the resultant solution. The reaction mixture was stirred for 22 h at 85° C. under nitrogen outside glove box. The mixture was passed through a pad of silica gel, which was rinsed with toluene. The combined solution was concentrated on a rotary evaporator, followed by flash column chromatography (5% to 10% ethylacetate in hexane, gradient) to afford 2.8 g of a white solid. NMR analysis confirmed the structure of intermediate compound 18.

Part 2. Synthesis of Intermediate 19

In a nitrogen purged glove box, diamine 18 (1 g, 0.935 mmol) and 4-bromo-4'-iodobiphenyl (1.026 g, 2.86 mmol) were dissolved in toluene (30 mL) in a 100 mL of round bottom flask, followed by the addition of the toluene (7 mL) solution of tris(dibenzylideneacetone)dipalladium(0) (24 mg, 0.027 eq.) and 1,1'-bis(diphenylphosphino)ferrocene (28 mg, 0.053 eq) to the mixture. After stirring the mixture for 5 min, sodium t-butoxide (229 mg, 2.38 mmol, 2.5 eq) was added to the resultant solution. The reaction mixture was stirred for 22 h at 95° C. under nitrogen outside glove box. The mixture was passed through a pad of silica gel, which was rinsed with toluene. The combined solution was concentrated on a rotary evaporator, followed by flash column chromatography (5% to 20% ethylacetate in hexane, gradiently) to afford 1.3 g of a white solid. NMR analysis confirmed the structure of compound 19.

Part 3. Synthesis of Compound V
The polymerization of compound 19 was performed as outline in example 1 for the synthesis of compound C to yield a white polymer. Molecular weight determination (GPC, THF, polystyrene standards): $M_w$=212,506; $M_n$=73,056; PDI=2.91.
Example 6
Synthesis of Compound W
Compound W was synthesized using the route shown below:
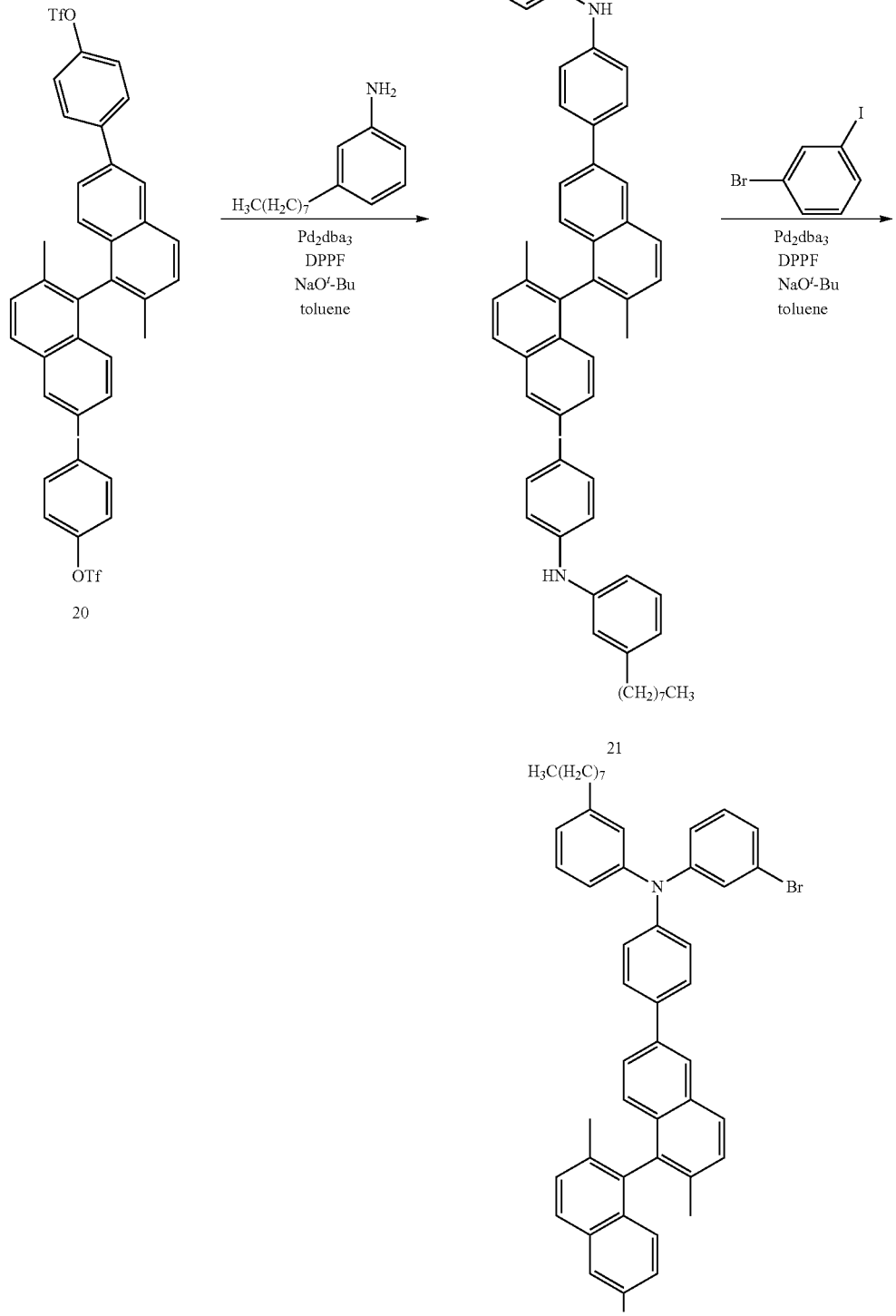

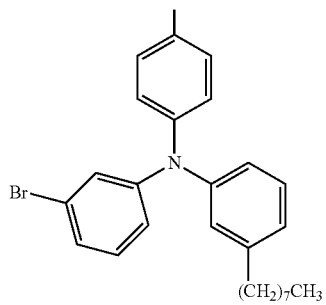

↓

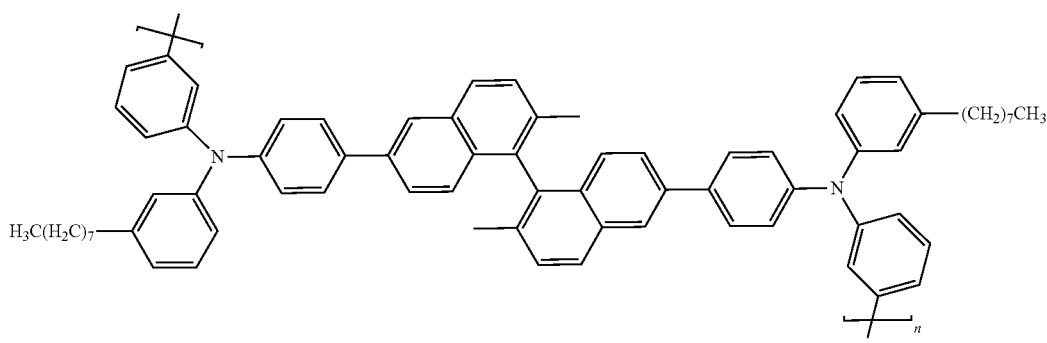

Compound X

Part 1: Synthesis of Intermediate 21:

In a nitrogen purged glove box, ditriflate 20 (1.7 g, 2.33 mmol) and 3-octylaniline (1 g, 4.89 mmol) were dissolved in toluene (20 mL) in a 100 mL of round bottom flask, followed by the addition of the toluene (10 mL) solution of tris(dibenzylideneacetone)dipalladium(0) (58 mg, 0.027 eq.) and 1,1'-bis(diphenylphosphino)ferrocene (68 mg, 0.053 eq) to the mixture. After stirring the mixture for 5 min, sodium t-butoxide (0.56 g, 5.82 mmol, 2.5 eq) was added to the resultant solution. The reaction mixture was stirred for 16 h at 85° C. under nitrogen outside glove box. The mixture was passed through a pad of silica gel, which was rinsed with toluene. The combined solution was concentrated on a rotary evaporator, followed by flash column chromatography (10% to 40% methylene chloride in hexane, gradiently) to afford 1.6 g of product. NMR analysis confirmed the structure of intermediate compound 21.

Part 2: Synthesis of Intermediate 22: In a nitrogen purged glove box, diamine 21 (1.5 g, 1.78 mmol) and 4-bromo-3-iodobenzene (1.51 g, 5.35 mmol) were dissolved in toluene (40 mL) in a 100 mL of round bottom flask, followed by the addition of the toluene (7 mL) solution of tris(dibenzylideneacetone)dipalladium(0) (47 mg, 0.027 eq.) and 1,1'-bis(diphenylphosphino)ferrocene (53 mg, 0.053 eq) to the mixture. After stirring the mixture for 5 min, sodium t-butoxide (0.428 g, 4.45 mmol, 2.5 eq) was added to the resultant solution. The reaction mixture was stirred for 4 days at 90° C. under nitrogen outside glove box. The mixture was passed through a pad of silica gel, which was rinsed with toluene. The combined solution was concentrated on a rotary evaporator, followed by flash column chromatography (5% toluene in hexane) to afford 1.6 g of a white solid. NMR analysis confirmed the structure of compound 22.

Part 3. Synthesis of Compound W

The polymerization of compound 22 was performed as outline in example 1 for the synthesis of compound C to yield a white polymer in 33% yield. Molecular weight determination (GPC, THF, polystyrene standards): $M_w$=210,638; $M_n$=33,194; PDI=6.34.

Example 7

Synthesis of Compound M

Compound M was synthesized using the route shown below:

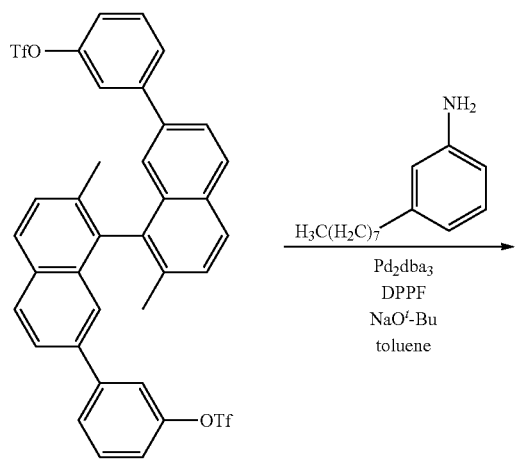
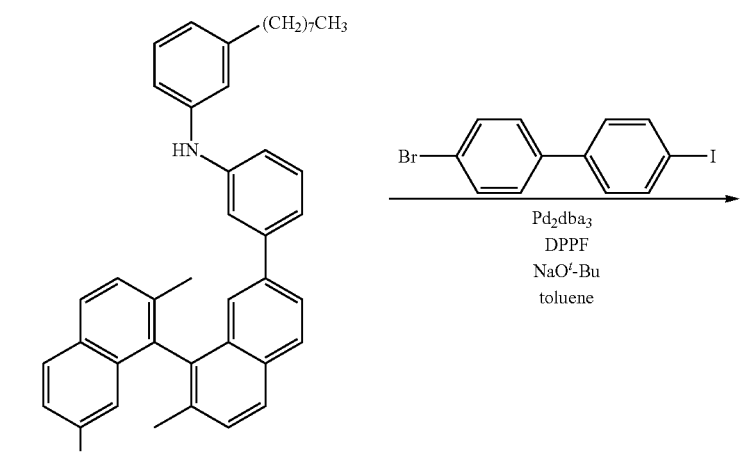
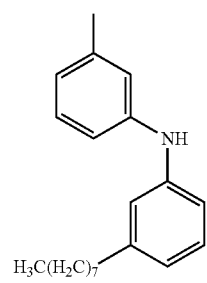

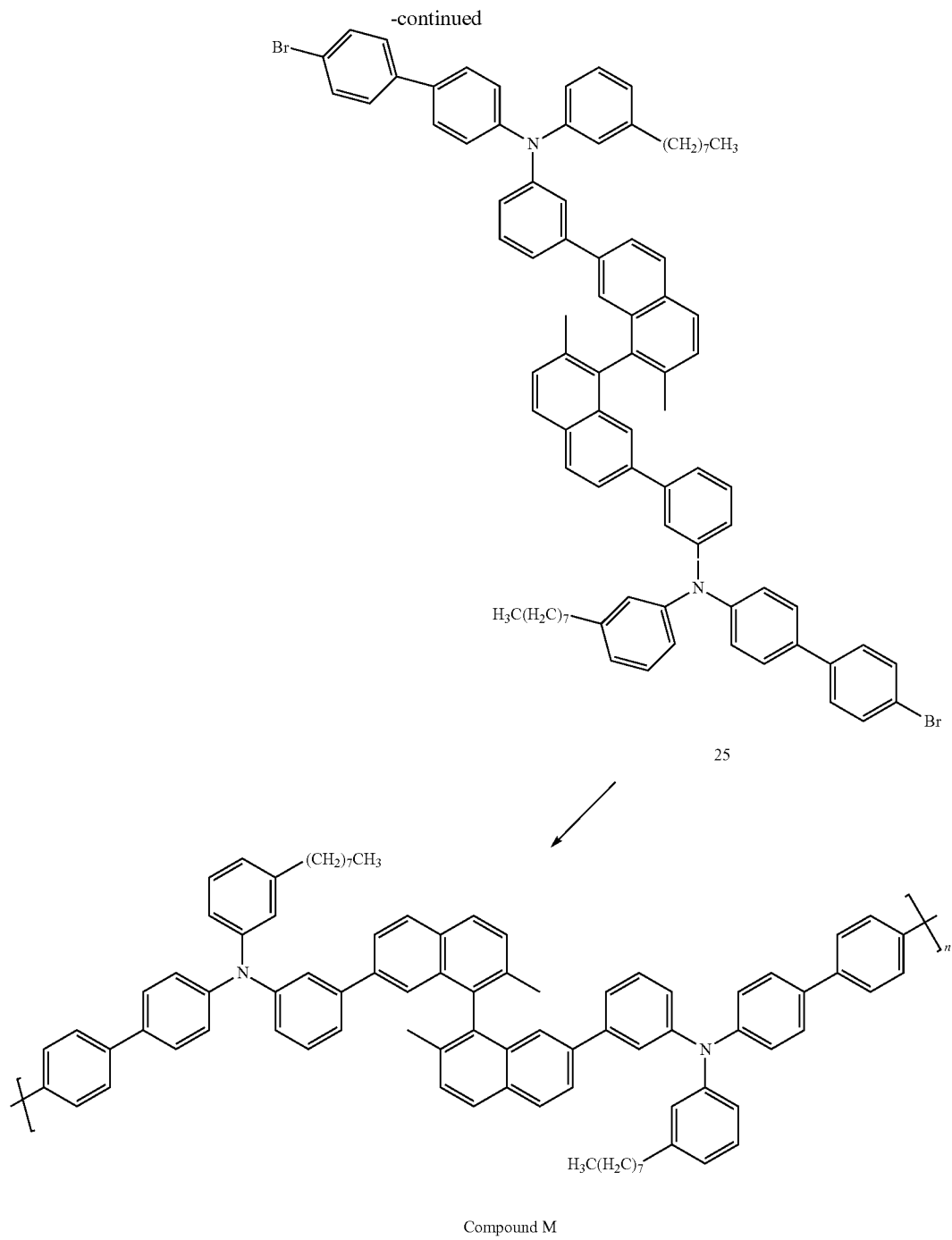

Compound M

Part 1: Synthesis of Intermediate 24:

In a nitrogen purged glove box, ditriflate 23 (3 g, 4.11 mmol) and 3-octylaniline (1.77 g, 8.62 mmol) were dissolved in toluene (40 mL) in a 100 mL of round bottom flask, followed by the addition of the toluene (10 mL) solution of tris(dibenzylideneacetone)dipalladium(0) (102 mg, 0.027 eq.) and 1,1'-bis(diphenylphosphino)ferrocene (121 mg, 0.053 eq) to the mixture. After stirring the mixture for 5 min, sodium t-butoxide (0.986 g, 10.26 mmol, 2.5 eq) was added to the resultant solution. The reaction mixture was stirred for 3 days at 85° C. under nitrogen outside glove box. The mixture was passed through a pad of silica gel, which was rinsed with toluene. The combined solution was concentrated on a rotary evaporator, followed by flash column chromatography (5% to 10% ethylacetate in hexane, gradiently) to afford 3 g of a white solid as a product. NMR analysis confirmed the structure of intermediate compound 24.

Part 2: Synthesis of Intermediate 25:

In a nitrogen purged glove box, diamine 24 (1.2 g, 1.42 mmol) and 4-bromo-4'-iodobiphenyl (2.3 g, 6.42 mmol) were dissolved in toluene (30 mL) in a 100 mL of round bottom flask, followed by the addition of the toluene (8 mL) solution of tris(dibenzylideneacetone)dipalladium(0) (35 mg, 0.027 eq.) and 1,1'-bis(diphenylphosphino)ferrocene (42 mg, 0.053 eq) to the mixture. After stirring the mixture for 5 min, sodium t-butoxide (341 mg, 3.55 mmol, 2.5 eq) was added to the resultant solution. The reaction mixture was stirred for 20 h at 95° C. under nitrogen outside glove box. The mixture was passed through a pad of silica gel, which was rinsed with toluene. The combined solution was concentrated on a rotary evaporator, followed by flash column chromatography (7% toluene in hexane) to afford 1.2 g of a white solid. NMR analysis confirmed the structure of compound 25.

Part 3. Synthesis of Compound M

The polymerization of compound 25 was performed as outline in example 1 for the synthesis of compound C to yield temperature of the heating block was raised to 60° C. Compound 5 (1.08 g, 0.85 mmol) and 3,5-dibromostyrene (0.0395 g, 0.15 mmol) were dissolved in toluene (13 mL) and then added to the catalyst solution. The solution was for six hours and then cooled to room temperature. The polymer was isolated as previously described for compounds C and T to give compound P as a white polymer in 85% yield (0.825 g). Molecular weight determination (GPC, THF, polystyrene standards): $M_w$=913,631; $M_n$=50,871; PDI=17.96.

Example 9

Synthesis of Compound N

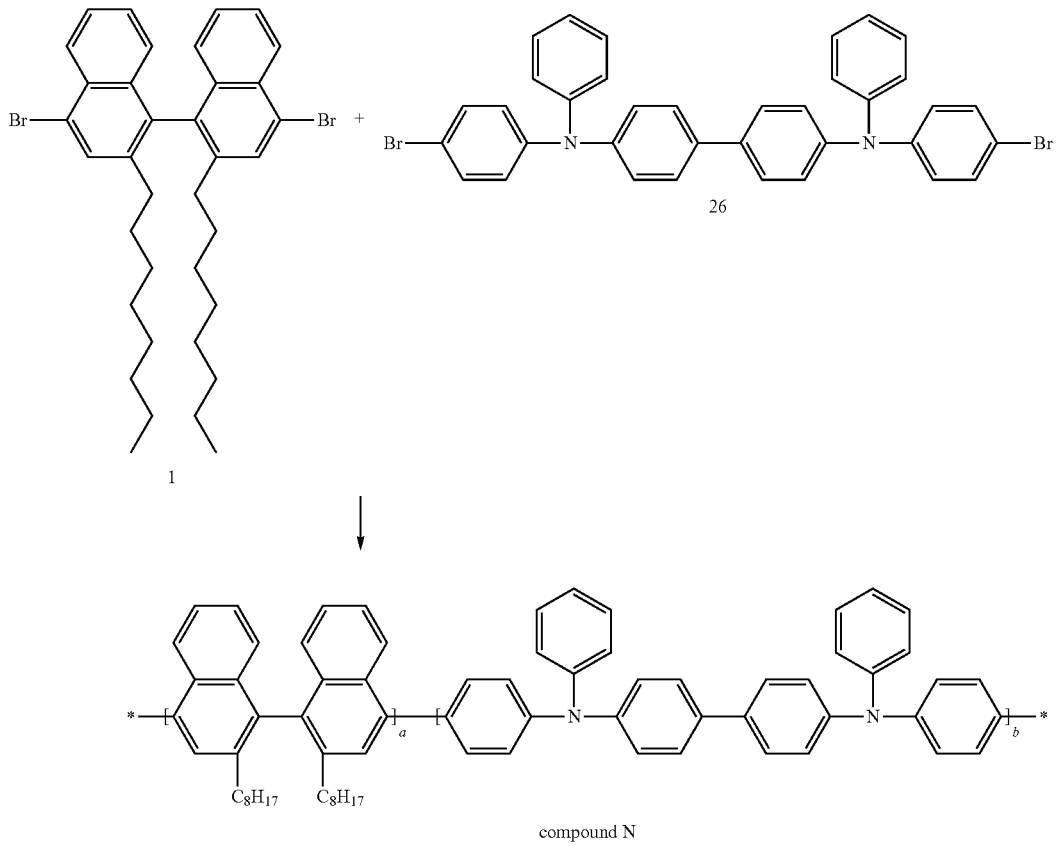

compound N a white polymer. Molecular weight determination (GPC, THF, polystyrene standards): $M_w$=82,023; $M_n$=27,177; PDI=3.02.

Example 8

Synthesis of Compound P

Under an atmosphere of nitrogen bis(1,5-cyclooctadiene) nickel(0) (0.564 g, 2.05 mmol), 2,2'-dipyridyl (0.32 g, 2.05 mmol) and 1,5-cyclooctadiene (0.222 g, 2.05 mmol) were dissolved in 2 mL DMF. The catalyst solution was stirred and heated in an aluminum block at 60° C. for 30 minutes. The Under an atmosphere of nitrogen bis(1,5-cyclooctadiene) nickel(0) (1.13 g, 4.1 mmol), 2,2'-dipyridyl (0.64 g, 4.1 mmol) and 1,5-cyclooctadiene (0.444 g, 4.1 mmol) were dissolved in 3 mL DMF. The catalyst solution was stirred and heated in an aluminum block at 60° C. for 30 minutes. The temperature of the heating block was raised to 70° C. Compound 1 (0.637 g, 1 mmol) and diamine 26 (0.646 g, 1 mmol) were dissolved in toluene (17 mL) and then added to the catalyst solution. The solution was for six hours and then cooled to room temperature. The polymer was isolated as previously described for compounds C and T to give compound N as a white polymer in 79% yield (0.760 g). Molecular weight determination (GPC, THF, polystyrene standards): $M_w$=284,019; $M_n$=45,611; PDI=6.23.

Example 10
Synthesis of Compound X
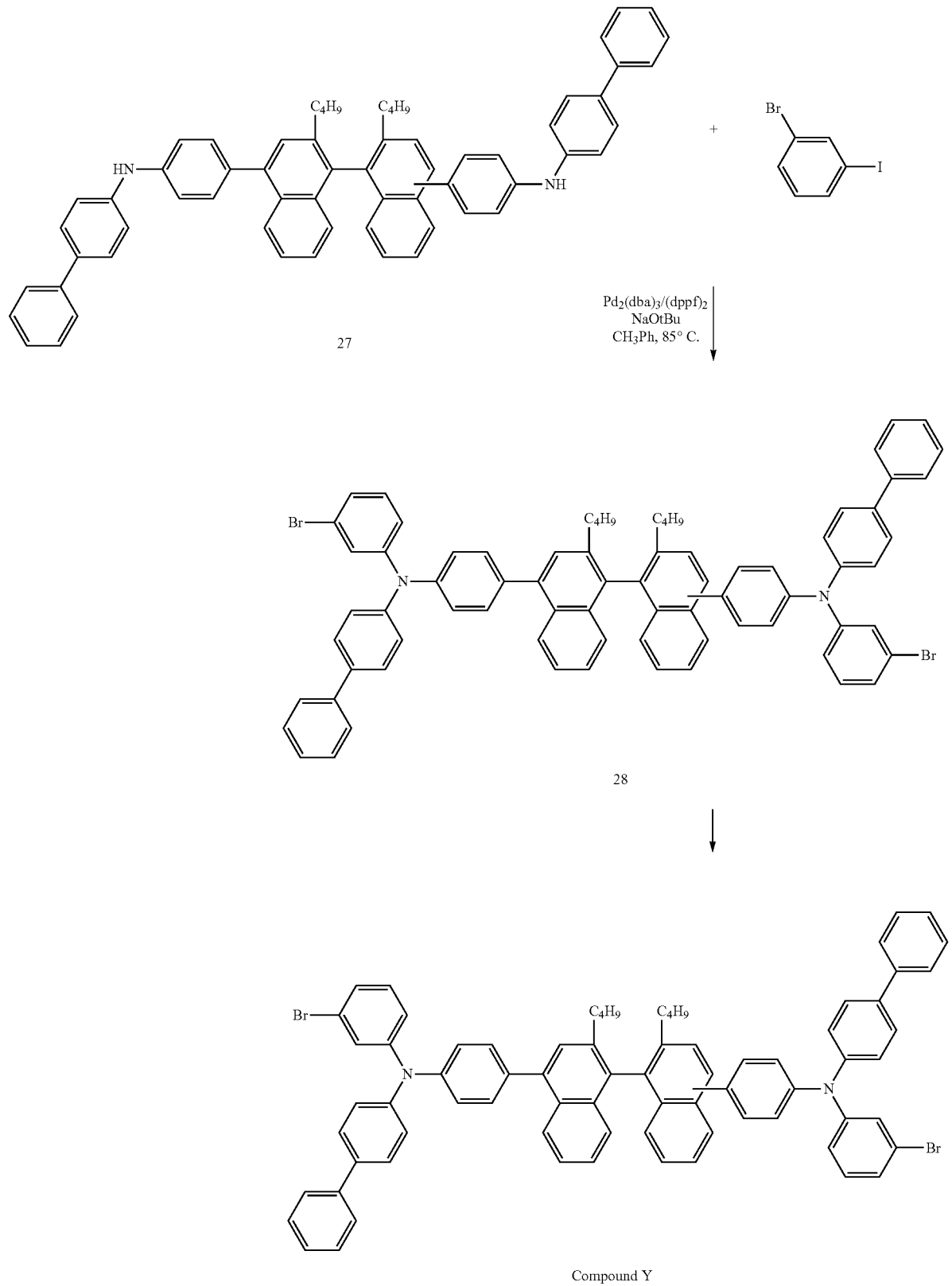

Part 1. Synthesis of Compound 28.

In a nitrogen purged glove box, to a 300 ml round bottom flask equipped with a stir bar was added compound 27 (1.61 g, 1.89 mmol), 1-bromo-3-iodobenzene (1.6 g, 5.66 mmol), tris(dibenzylideneacetone)dipalladium(0) (43 mg, 47 μmol), 1,1"-bis(diphenyl-phosphino)ferrocene (52 mg, 94 μmol), toluene (50 ml), and sodium-tert-butoxide (0.45 g, 4.7 mmol). The reaction vessel was capped, removed from glove box, equipped with a reflux condenser and $N_2$ bubbler, and heated at 85° C. for 3 days. The reaction mixture was allowed to cool to room temperature, diluted with dichloromethane, and filtered through a plug of silica gel and diatomaceous earth. The filtrate was concentrated on a rotary evaporator to give crude product. The crude product was purified by column chromatography (silica gel, hexanes:$CH_2Cl_2$ gradient) then washed with boiling MeOH to give compound 28 as white powder (1.42 g, 65%). $^1$H NMR analysis (500 MHz, $CD_2Cl_2$) is consistent with structure 28.

Part 2. Synthesis of Compound X.

Compound X was synthesized as previously described for compound C to obtain it as white beads in 65%. Molecular weight determination (GPC, THF, polystyrene standard): $M_w$=320,000; $M_n$=97,000; PDI=3.29.

Example 11

Synthesis of Compound Y1

Part 1. Synthesis of Intermediate 29:

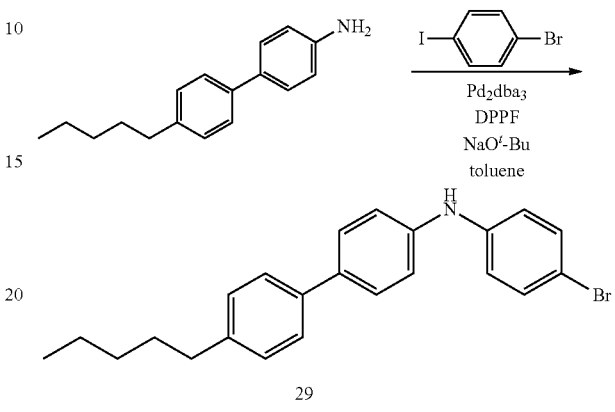

In a nitrogen purged glove box, 4-bromo-1-iodobenzene (3.54 g, 12.53 mmol) and 4-(p-pentylphenyl)-aniline (3 g, 12.53 mmol) were dissolved in toluene (50 mL) in a 100 mL of round bottom flask, followed by the addition of the toluene (10 mL) solution of tris(dibenzylideneacetone)dipalladium (0) (286 mg, 0.025 eq.) and 1,1'-bis(diphenylphosphino)ferrocene (347 mg, 0.05 equiv) to the mixture. After stirring the mixture for 5 min, sodium t-butoxide (1.44 g, 15.03 mmol, 1.2 eq) was added to the resultant solution. The reaction mixture was stirred for 6 h at 80° C. under nitrogen outside glove box. The mixture was passed through a pad of silica gel, which was rinsed with toluene. The combined solution was concentrated on a rotary evaporator, followed by recrystallization (in hexane and ethylacetate solvent) and flash column chromatography (5% ethyl acetate in hexane, gradient) to afford 2.3 g of a white solid. NMR analysis confirmed the structure of intermediate compound 29.

Part 2. Synthesis of Intermediate 31:

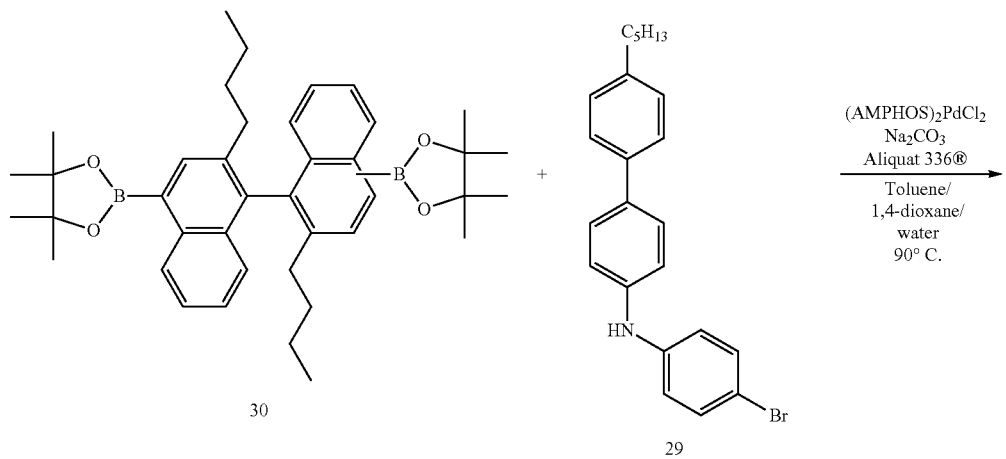

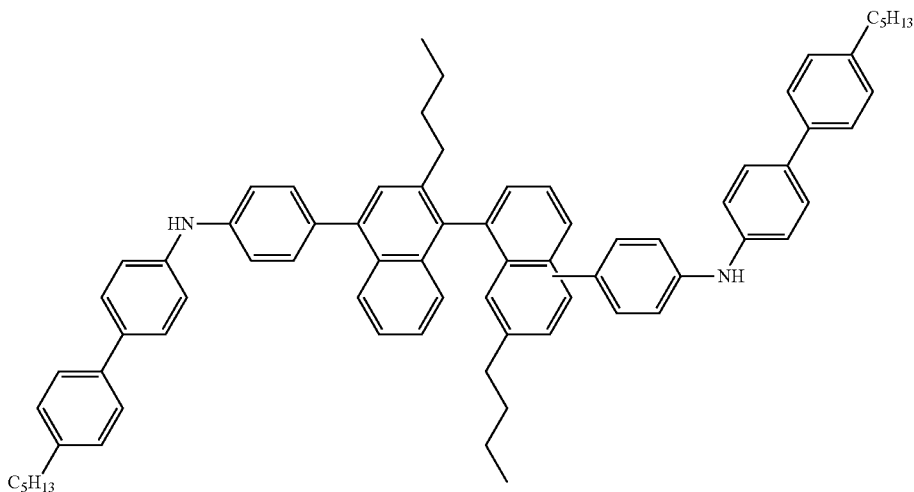

31

To a 100 ml, 2-neck round bottom flask equipped with a stir bar, reflux condenser, and N₂ bubbler, was added Na₂CO₃ (1.4 g, 13.3 mmol) and water (8 mL). To the Na₂CO₃ solution was added compound 30 (1.65 g, 2.66 mmol), compound 29 (2.1 g, 5.3 mmol), Aliquat 336® (0.11 g, 0.27 mmol), toluene (12 ml), and 1,4-dioxane (12 ml). The mixture was sparged with N₂ for 1 h, then bis(di-tert-butyl(4-dimethylaminophenyl)-phosphine dichloropalladium(II) (4.1 mg, 5.3 μmol) was added. The mixture was sparged with N₂ for 10 minutes, then heated at 90° C. for 1.5 h. The reaction mixture was allowed to cool to RT and diluted with toluene. The organic layer was separated, washed with water (3×) and brine, dried over MgSO₄, filtered, concentrated on a rotary evaporator, and dried under high vacuum to isolate a light brown, foamy solid. The crude product was purified by column chromatography (silica gel, 2:1 Hex:CH₂Cl₂) to isolate 2.4 g white, foamy solid in 91%. ¹H NMR (500 MHz, CD₂Cl₂) is consistent with structure 31.

Part 3. Synthesis of Intermediate 32:

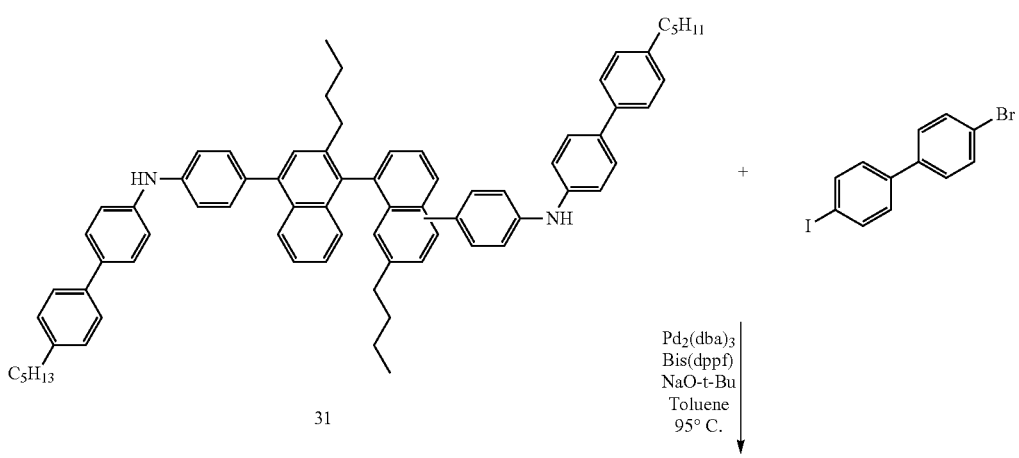

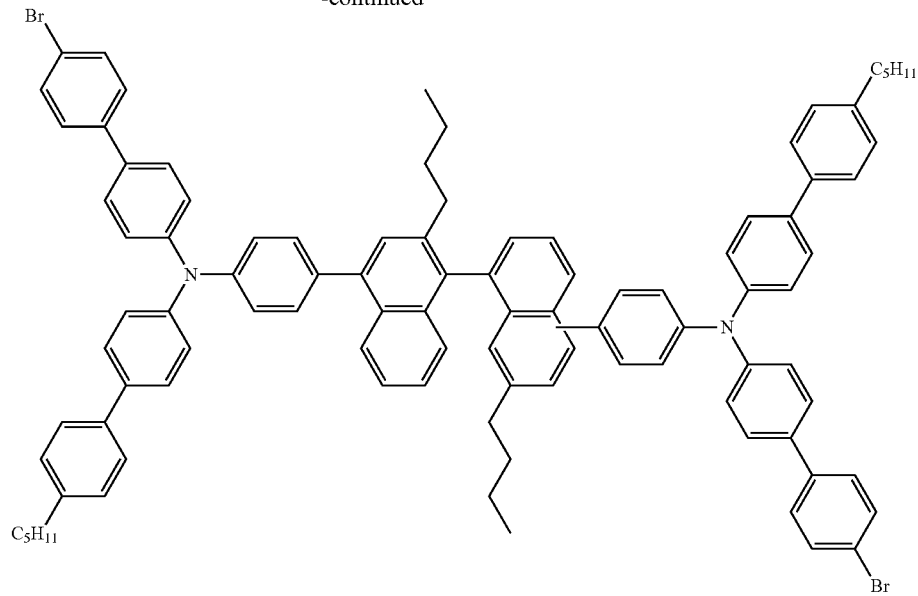

32

In a nitrogen purged glove box, to a 300 mL round bottom flask equipped with a stir bar was added compound 31 (2.3 g, 2.32 mmol), iodo-bromobiphenyl (2.5 g, 6.9 mmol), tris(dibenzylideneacetone)dipalladium(0) (53 mg, 50 μmol), 1,1"-bis(diphenyl-phosphino)ferrocene (64 mg, 120 μmol), toluene (100 ml), and sodium-tert-butoxide (0.56 g, 5.8 mmol). The reaction vessel was capped, removed from glove box, equipped with a reflux condenser and $N_2$ bubbler, and heated at 95° C. for 18 hours. The reaction mixture was allowed to cool to RT, diluted with dichloromethane, and filtered through a plug of silica gel and diatomaceous earth. The filtrate was concentrated on a rotary evaporator to give crude product. The crude product was purified by column chromatography (silica gel, hexanes:$CH_2Cl_2$ gradient) then washed with boiling MeOH to give 2.8 g white powder (83% yield). $^1$H NMR analysis (500 MHz, $CD_2Cl_2$) is consistent with structure 32.

Part 3. Synthesis of Compound Y1:

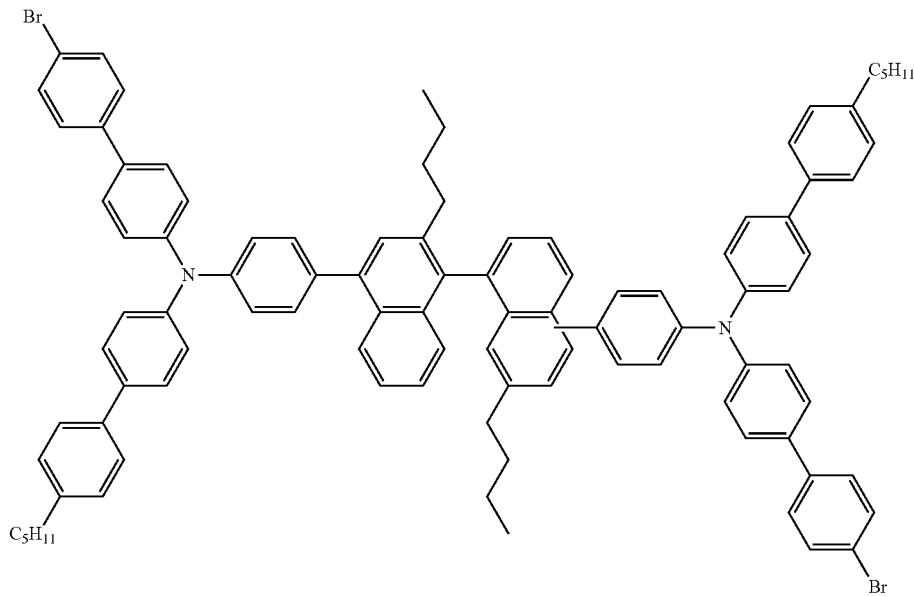

32

$(COD)_2Ni^0$
2,2'-dipyridyl/COD
$CH_3Ph/DMF$ 70° C.

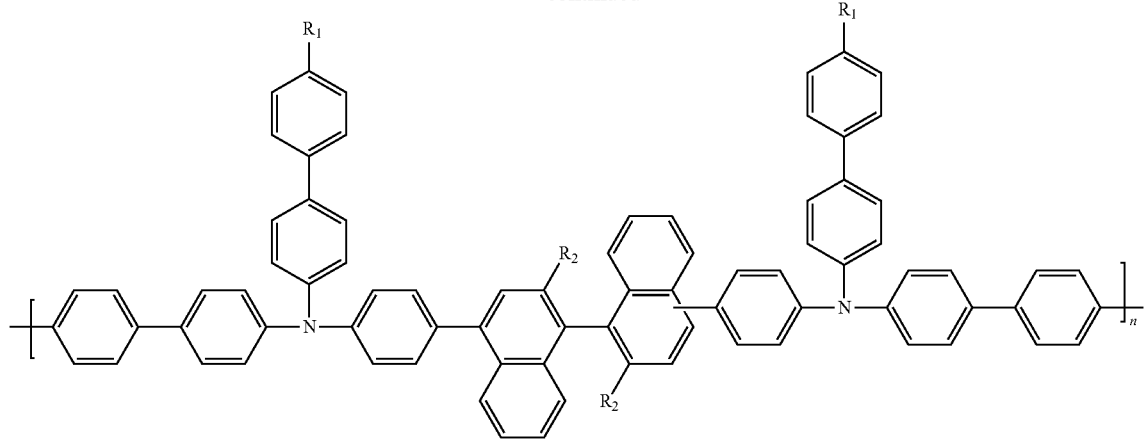

compound Y1: R1 = pentyl; R2 = butyl

The polymerization of compound 32 was performed as outline in example 1 for the synthesis of compound C to yield a white polymer in 95% yield. Molecular weight determination (GPC, THF, polystyrene standards): $M_w$=169,000; $M_n$=91,700; PDI=1.84.

Example 12

Synthesis of Compound Y3

Part 1

Synthesis of Intermediate Compound 33

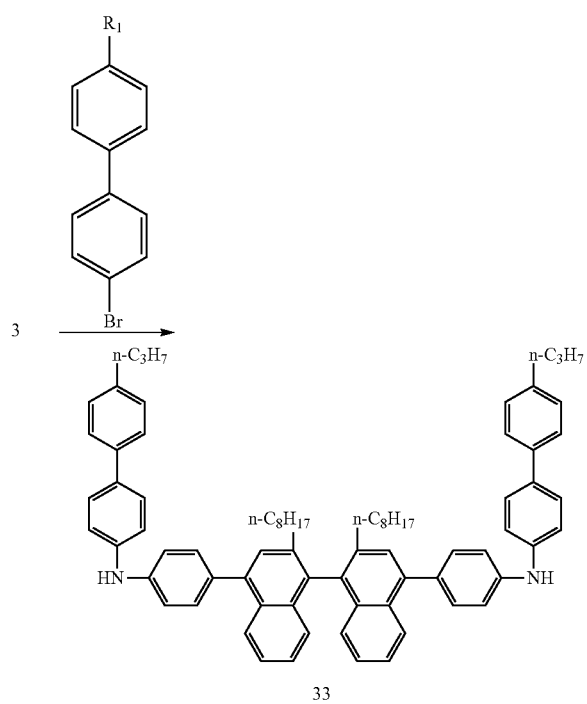

Under an atmosphere of nitrogen, compound 3 (2.0 g, 3.03 mmol), 4-bromo-4'-propylbiphenyl (1.67 g, 6.05 mmol), tris (dibenzylideneacetone)dipalladium(0) (139 mg, 5 mol %), tri-t-butylphosphine (61 mg, 10 mol %) and toluene (27 mL) were combined. Sodium t-butoxide (0.872 g, 9.08 mmol) was added and the reaction was stirred at room temperature for 40 h. 4-bromo-4'-propylbiphenyl (250 mg, 0.091 mmol), tris (dibenzylideneacetone)dipalladium(0) (55 mg, 2 mol %), tri-t-butylphosphine (25 mg, 4 mol %) and sodium t-butoxide (291 mg, 3.03 mmol) were then added. After another 23 h, the reaction mixture was filtered through a pad of Celite, rinsing with toluene. The solution was concentrated on a rotary evaporator and dried under vacuum. The product was purified by medium pressure liquid chromatography on silica gel (0-40% methylene chloride gradient in hexanes) to give 1.70 g (53% yield) of a white solid. NMR analysis confirmed the structure of Intermediate Compound 33 as a mixture of 4,4'- and 4,5'-regioisomers. Purity (UPLC): 97.8%.

Part 2

Synthesis of Intermediate 4-bromo-4'-iodobiphenyl

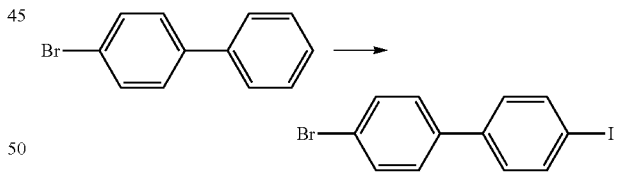

A 4-neck one liter round bottom flask equipped with mechanical stirrer, thermometer and reflux condenser topped with nitrogen bubbler inlet was charged with 4-bromobiphenyl (23.31 g, 100 mmol) in acetic acid (400 mL), sulfuric acid (10 mL) and water (20 mL). To this stirring mixture was added iodic acid (4.84 g, 27.5 mmol) followed immediately by addition of iodine chips (11.17 g, 44.0 mmol). The reaction flask was immersed in a preheated tri(ethylene glycol) heating bath and heated at 65° C. internal temperature. After 30 min the bath temperature was increased such that the internal temperature raised to 85° C. after 20 min. Heating at this temperature was continued for 4.5 hours at which point UPLC analysis showed the reaction to be complete. After stirring overnight at room temperature the reaction mixture was vacuum filtered through a coarse fritted funnel and the solids were rinsed with water. The resulting white solid (32.1 g, 89% yield) had mp 177-179° C. and was used without further purification in the next step. NMR analysis confirmed the structure of Intermediate Compound 3,4-bromo-4'-iodobiphenyl. Purity (UPLC): >99%.

Part 3

Synthesis of Intermediate Compound 34

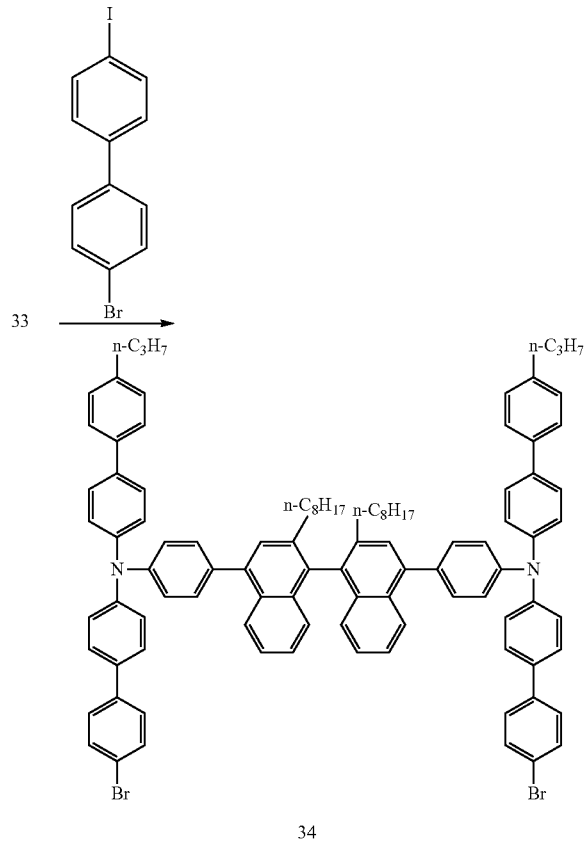

In a nitrogen purged glovebox, a 3-neck round bottom flask equipped with a magnetic stirrer, thermometer and reflux condenser topped with a gas inlet adaptor in the closed position was charged with 33 (1.70 g, 1.62 mmol), 4-bromo-4'-iodobiphenyl (2.62 g, 7.29 mmol), tris(dibenzylideneacetone)dipalladium(0) (178 mg, 12 mol %), bis(diphenylphosphinoferrocene) (215 mg, 24 mol %) and toluene (30 mL) through the open neck. Sodium t-butoxide (0.342 g, 3.56 mmol) was added, the open neck was capped and the reaction vessel was removed from the glovebox. A nitrogen bubbler hose was fitted to the gas inlet adaptor and the stopcock was turned to the open position under a slight positive pressure of nitrogen. The reaction on was heated reflux with a tri(ethylene glycol) bath. After 16 h, the reaction was cooled to room temperature and tris(dibenzylideneacetone)dipalladium(0) (178 mg, 12 mol %), bis(diphenylphosphino)ferrocene (215 mg, 24 mol %) and sodium t-butoxide (342 mg, 3.56 mmol) was added to the reaction mixture. After additional 2 h at reflux, the reaction mixture was cooled to room temperature. After 72 h at room temperature the reaction mixture was filtered through a pad of Celite, rinsing with toluene. The filtrate was concentrated by rotary evaporation. The crude product was dried under high vacuum and purified by medium pressure liquid chromatography on silica gel (0-35% methylene chloride gradient in hexanes) to give 1.42 g (58% yield) of a white solid. NMR analysis confirmed the structure of Intermediate Compound 34 as a mixture of 4,4'- and 4,5'-regioisomers. Purity (UPLC): 98.7%.

Part 4

Synthesis of Compound Y3

The polymerization of compound 34 was performed as outline in example 1 for the synthesis of compound C to yield a white polymer. Molecular weight determination (GPC, THF, polystyrene standards): $M_w$=512,983; $M_n$=136,936; PDI=3.75.

DEVICE EXAMPLES

The following materials were used:
Buffer 1 is an aqueous dispersion of polypyrrole and a polymeric fluorinated sulfonic acid. The material was prepared using a procedure similar to that described in Example 1 of published U.S. Patent application no. 2005/0205860.

H1:

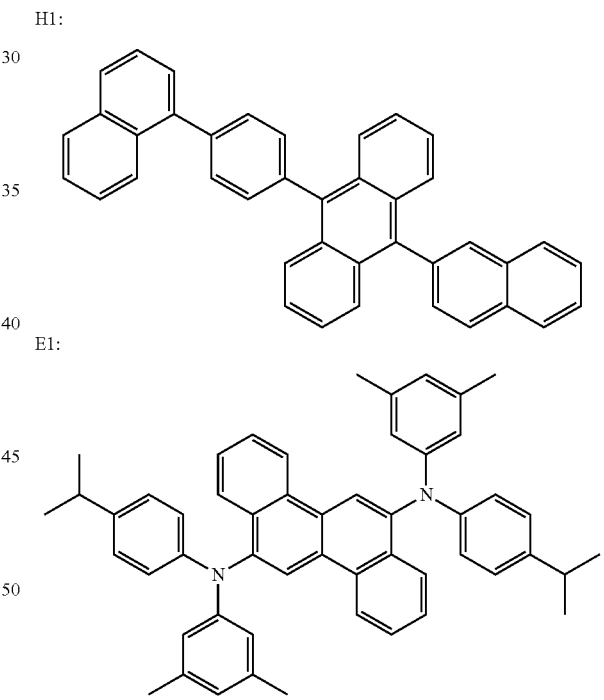

E1:

Alq3=tris(8-hydroxyquinoline)aluminum
ZrQ=tetrakis-(8-hydroxyquinoline) zirconium Device Example 1

This example demonstrates the fabrication and performance of a device having deep blue emission.
The device had the following layers:
anode=Indium Tin Oxide (ITO): 50 nm
buffer layer=Buffer 1 (25 nm)
hole transport layer=Compound C, from Example 1 (20 nm)

photoactive layer=13:1 host H1:dopant E1 (47 nm)
electron transport layer=ZrQ (20 nm)
cathode=CsF/Al (0.7/100 nm)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 50 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of Buffer 1 was spin-coated over the ITO surface and heated to remove solvent. After cooling, the substrates were then spin-coated with a solution of the hole transport material, and then heated to remove solvent. After cooling, the substrates were spin-coated with the emissive layer solution, and heated to remove solvent. The substrates were masked and placed in a vacuum chamber. A ZrQ layer was deposited by thermal evaporation, followed by a layer of CsF. Masks were then changed in vacuo and a layer of Al was deposited by thermal evaporation. The chamber was vented, and the devices were encapsulated using a glass lid, desiccant, and UV curable epoxy.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The results are given in Table 1, below.

Device Example 2

This example demonstrates the fabrication and performance of a device having deep blue emission. The following materials were used:
Indium Tin Oxide (ITO): 50 nm
buffer layer=Buffer 1 (25 nm)
hole transport layer=Compound C (20 nm)
photoactive layer=4:1 host H1:dopant E1 (39 nm)
electron transport layer=ZrQ (20 nm)
cathode=CsF/Al (0.8/100 nm)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 50 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of Buffer 1 was spin-coated over the ITO surface and heated to remove solvent. After cooling, the substrates were then spin-coated with a solution of the hole transport material, and then heated to remove solvent. After cooling, the substrates were masked and loaded into the vacuum chamber. A 4:1 ratio of fluorescent host:dopant was co-evaporated to a thickness of 39 nm. The substrates were masked and placed in a vacuum chamber. A ZrQ layer was deposited by thermal evaporation, followed by a layer of CsF. Masks were then changed in vacuo and a layer of Al was deposited by thermal evaporation. The chamber was vented, and the devices were encapsulated using a glass lid, dessicant, and UV curable epoxy.

The OLED samples were characterized as described above.

The results are given in Table 1 below.

Device Example 3

This example demonstrates the fabrication and performance of a device having deep blue emission. The following materials were used:
Indium Tin Oxide (ITO): 50 nm
buffer layer=Buffer 1 (50 nm)
hole transport layer=Compound T (20 nm)
photoactive layer=6:1 host H1:dopant E1 (32 nm)
electron transport layer=ZrQ (10 nm)
cathode=CsF/Al (0.7/100 nm)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 50 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of Buffer 1 was spin-coated over the ITO surface and heated to remove solvent. After cooling, the substrates were then spin-coated with a solution of the hole transport material, and then heated to remove solvent. After cooling, the substrates were masked and loaded into the vacuum chamber. A 6:1 ratio of fluorescent host:dopant was co-evaporated to a thickness of 32 nm. The substrates were masked and placed in a vacuum chamber. A ZrQ layer was deposited by thermal evaporation, followed by a layer of CsF. Masks were then changed in vacuo and a layer of Al was deposited by thermal evaporation. The chamber was vented, and the devices were encapsulated using a glass lid, dessicant, and UV curable epoxy.

The OLED samples were characterized as described above.

The results are given in Table 1 below.

Device Example 4

This example demonstrates the fabrication and performance of a device having deep blue emission.
The device had the following layers:
anode=Indium Tin Oxide (ITO): 50 nm
buffer layer=Buffer 1 (25 nm)
hole transport layer=Compound V
photoactive layer=13:1 host H1:dopant E1 (47 nm)
electron transport layer=ZrQ (20 nm)
cathode=CsF/Al (0.7/100 nm)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 50 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of Buffer 1 was spin-coated over the ITO surface and heated to remove solvent. After cooling, the substrates were then spin-coated with a solution of the hole transport material, and then heated to remove solvent. After cooling, the substrates were spin-coated with the emissive layer solution, and heated to remove solvent. The substrates were masked and placed in a vacuum chamber. A ZrQ layer was deposited by thermal evaporation, followed by a layer of CsF. Masks were then changed in vacuo and a layer of Al was deposited by thermal evaporation. The chamber was vented, and the devices were encapsulated using a glass lid, desiccant, and UV curable epoxy.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The results are given in Table 1, below.

Device Example 5

This example demonstrates the fabrication and performance of a device having deep blue emission. The following materials were used:
Indium Tin Oxide (ITO): 50 nm
buffer layer=Buffer 1 (25 nm)
hole transport layer=Compound V (20 nm)
photoactive layer=4:1 host H1:dopant E1 (39 nm)
electron transport layer=ZrQ (20 nm)
cathode=CsF/Al (0.8/100 nm)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 50 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of Buffer 1 was spin-coated over the ITO surface and heated to remove solvent. After cooling, the substrates were then spin-coated with a solution of the hole transport material, and then heated to remove solvent. After cooling, the substrates were masked and loaded into the vacuum chamber. A 4:1 ratio of fluorescent host:dopant was co-evaporated to a thickness of 39 nm. The substrates were masked and placed in a vacuum chamber. A ZrQ layer was deposited by thermal evaporation, followed by a layer of CsF. Masks were then changed in vacuo and a layer of Al was deposited by thermal evaporation. The chamber was vented, and the devices were encapsulated using a glass lid, dessicant, and UV curable epoxy.

The OLED samples were characterized as described above. The results are given in Table 1 below.

Device Example 6

This example demonstrates the fabrication and performance of a device having deep blue emission. The following materials were used:
Indium Tin Oxide (ITO): 50 nm
buffer layer=Buffer 1 (25 nm)
hole transport layer=Compound Z2 (20 nm)
photoactive layer=4:1 host H1:dopant E1 (39 nm)
electron transport layer=ZrQ (20 nm)
cathode=CsF/Al (0.8/100 nm)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 50 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of Buffer 1 was spin-coated over the ITO surface and heated to remove solvent. After cooling, the substrates were then spin-coated with a solution of the hole transport material, and then heated to remove solvent. After cooling, the substrates were masked and loaded into the vacuum chamber. A 4:1 ratio of fluorescent host:dopant was co-evaporated to a thickness of 39 nm. The substrates were masked and placed in a vacuum chamber. A ZrQ layer was deposited by thermal evaporation, followed by a layer of CsF. Masks were then changed in vacuo and a layer of Al was deposited by thermal evaporation. The chamber was vented, and the devices were encapsulated using a glass lid, dessicant, and UV curable epoxy.

The OLED samples were characterized as described above. The results are given in Table 1 below.

Device Example 7

This example demonstrates the fabrication and performance of a device having deep blue emission.
The device had the following layers:
anode=Indium Tin Oxide (ITO): 50 nm
buffer layer=Buffer 1 (25 nm)
hole transport layer=Compound Z3
photoactive layer=13:1 host H1:dopant E1 (47 nm)
electron transport layer=ZrQ (20 nm)
cathode=CsF/Al (0.7/100 nm)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 50 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of Buffer 1 was spin-coated over the ITO surface and heated to remove solvent. After cooling, the substrates were then spin-coated with a solution of the hole transport material, and then heated to remove solvent. After cooling, the substrates were spin-coated with the emissive layer solution, and heated to remove solvent. The substrates were masked and placed in a vacuum chamber. A ZrQ layer was deposited by thermal evaporation, followed by a layer of CsF. Masks were then changed in vacuo and a layer of Al was deposited by thermal evaporation. The chamber was vented, and the devices were encapsulated using a glass lid, desiccant, and UV curable epoxy.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The results are given in Table 1, below.

Device Example 8

This example demonstrates the fabrication and performance of a device having deep blue emission. The following materials were used:
  Indium Tin Oxide (ITO): 50 nm
  buffer layer=Buffer 1 (25 nm)
  hole transport layer=Compound Z3 (20 nm)
  photoactive layer=4:1 host H1:dopant E1 (39 nm)
  electron transport layer=ZrQ (20 nm)
  cathode=CsF/Al (0.8/100 nm)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 50 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of Buffer 1 was spin-coated over the ITO surface and heated to remove solvent. After cooling, the substrates were then spin-coated with a solution of the hole transport material, and then heated to remove solvent. After cooling, the substrates were masked and loaded into the vacuum chamber. A 4:1 ratio of fluorescent host:dopant was co-evaporated to a thickness of 39 nm. The substrates were masked and placed in a vacuum chamber. A ZrQ layer was deposited by thermal evaporation, followed by a layer of CsF. Masks were then changed in vacuo and a layer of Al was deposited by thermal evaporation. The chamber was vented, and the devices were encapsulated using a glass lid, dessicant, and UV curable epoxy.

The OLED samples were characterized as described above. The results are given in Table 1 below.

TABLE 1

| Example | CE [cd/A] | Voltage [V] | EL peak [nm] | CIE [x] | CIE [y] |
|---|---|---|---|---|---|
| Device 1 | 6.28 | 5.0 | 462 | 0.138 | 0.135 |
| Device 2 | 8.53 | 4.4 | 462 | 0.136 | 0.136 |
| Device 3 | 8.1 | 4.0 | 458 | 0.138 | 0.107 |
| Device 4 | 6.26 | 5.3 | 458 | 0.140 | 0.121 |
| Device 5 | 8.85 | 4.1 | 462 | 0.137 | 0.126 |
| Device 6 | 7.85 | 4.4 | 462 | 0.137 | 0.129 |
| Device 7 | 6.49 | 5.0 | 460 | 0.138 | 0.127 |
| Device 8 | 7.96 | 4.5 | 462 | 0.137 | 0.131 |

All data @ 1000 nits,
CE = current efficiency,
CIE[x] and CIE[y] refer to the x and y color coordinates according to the C.I.E. chromaticity scale (Commission Internationale de L'Eclairage, 1931).

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A compound having Formula II:

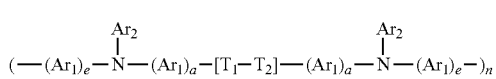

wherein:

Ar$^1$ is the same or different at each occurrence and is selected from the group consisting of phenylene, substituted phenylene, naphthylene, and substituted naphthylene;

Ar$^2$ is the same or different at each occurrence and is an aryl group;

T$^1$ and T$^2$ are independently the same or different at each occurrence and are conjugated moieties which are connected in a non-planar configuration;

a is the same or different at each occurrence and is an integer from 1 to 6;

e is the same or different at each occurrence and is an integer from 1 to 6; and n is an integer greater than 1.

2. The compound of claim 1, wherein the members of [T$^1$-T$^2$] are independently selected from the group consisting of:

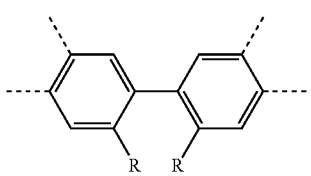

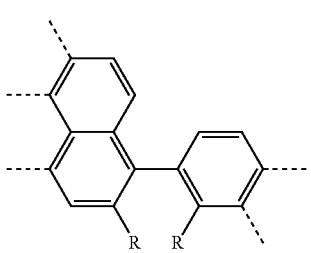

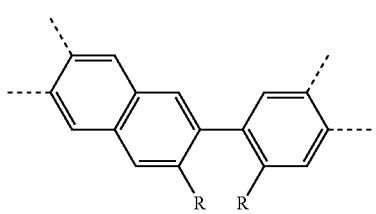

-continued

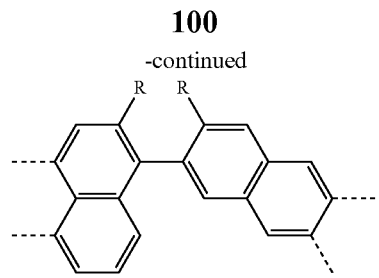

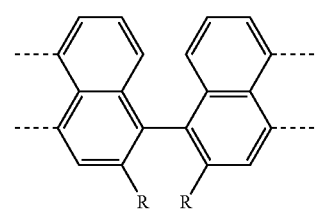

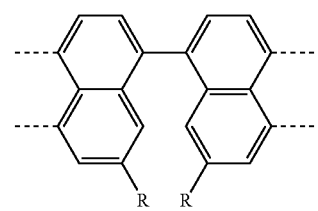

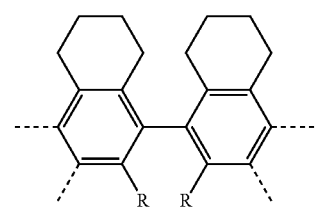

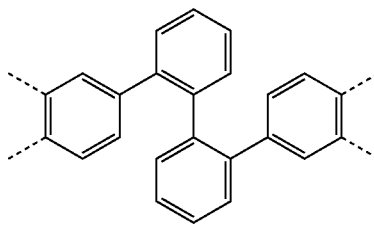

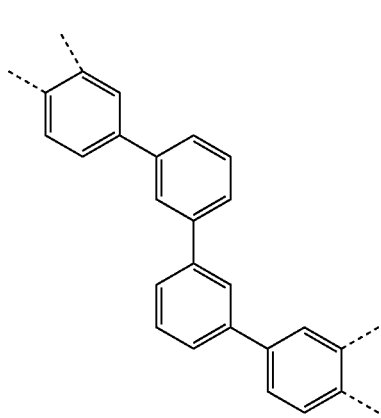

where:
R is the same or different and is selected from the group consisting of alkyl, aryl, alkoxy, aryloxy, fluoroalkyl, fluoroaryl, fluoroaryloxy fluoroalkyloxy, oxyalkyl, and alkenyl groups.

3. The compound of claim 2, wherein R is selected from the group consisting of C1-10 alkyl and C1-10 alkoxy.

4. The compound of claim 2, wherein R is selected from the group consisting of C3-8 branched alkyl and C3-8 branched alkoxy.

5. The compound of claim 2, wherein both R groups are joined together to form a non-aromatic ring.

6. The compound of claim 1, wherein a is 1-3.

7. The compound of claim 1, wherein $Ar^2$ has Formula a

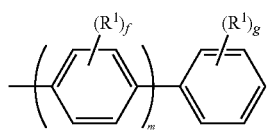

Formula a where:
$R^1$ is the same or different at each occurrence and is selected from the group consisting of alkyl, alkoxy, and silyl;
f is the same or different at each occurrence and is an integer from 0-4;
g is an integer from 0-5; and
m is an integer from 1 to 5.

8. The compound of claim 1, wherein $Ar^2$ is selected from the group consisting phenyl, p-biphenyl, p-terphenyl, naphthyl, phenylnaphthyl, and naphthylphenyl.

9. The compound of claim 1, wherein $Ar^2$ has a substituent comprising a crosslinking group.

10. The compound of claim 1, wherein at least one $Ar^2$ has at least one substituent selected from the group consisting of alkyl, alkoxy and silyl.

11. The compound of claim 1, wherein at least one $Ar^1$ is a substituted phenyl with a substituent selected from the group consisting of alkyl, alkoxy, silyl, and a substitutent with a crosslinking group.

12. A compound selected from the group consisting of Compound C

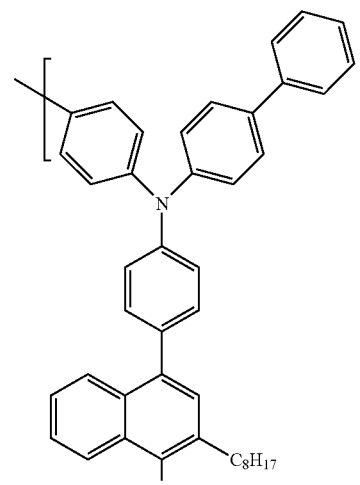

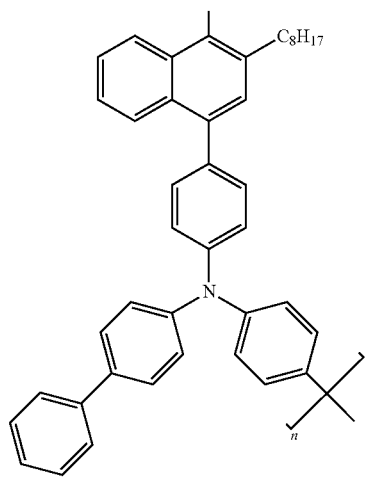

wherein n is an integer greater than 1;

Compound D:

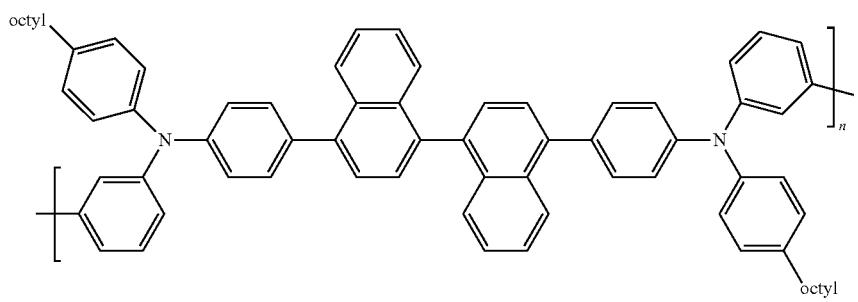

wherein n is an integer greater than 1;

Compound E
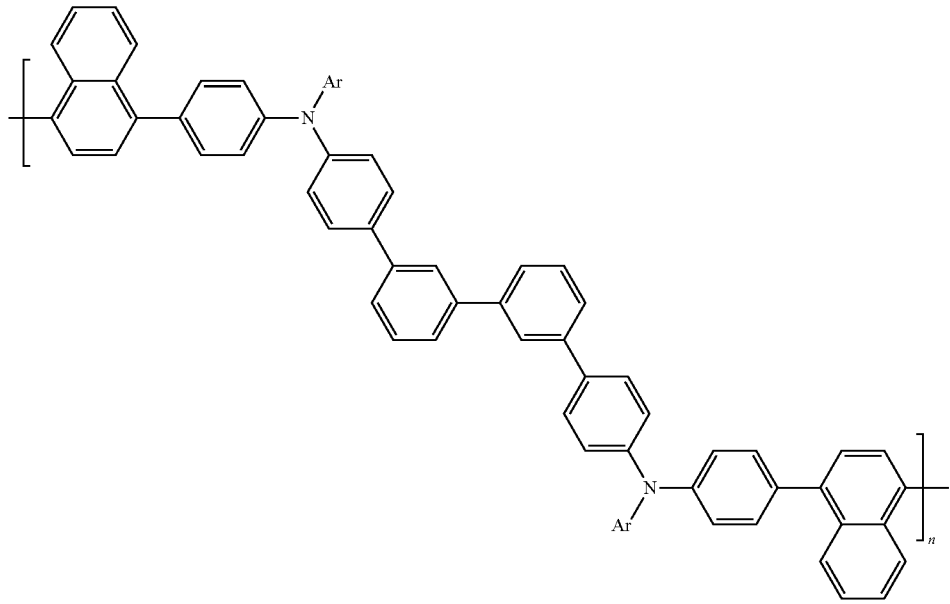
wherein Ar is phenyl or biphenyl and n is an integer greater than 1;
Compound F:
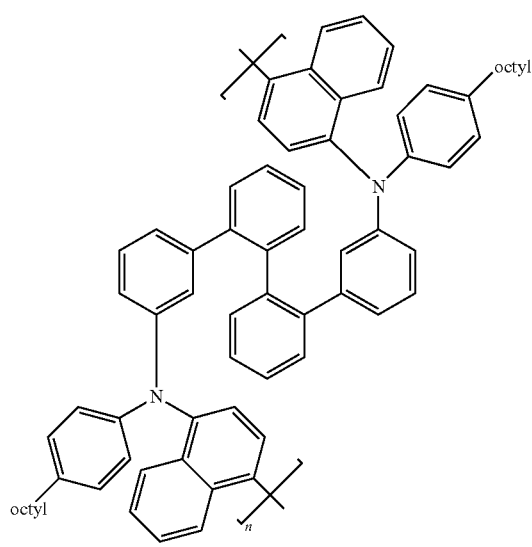
wherein n is an integer greater than 1;
Compound G:
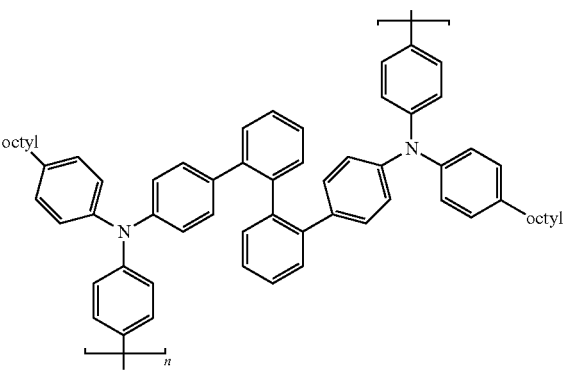
wherein n is an integer greater than 1;

Compound H:
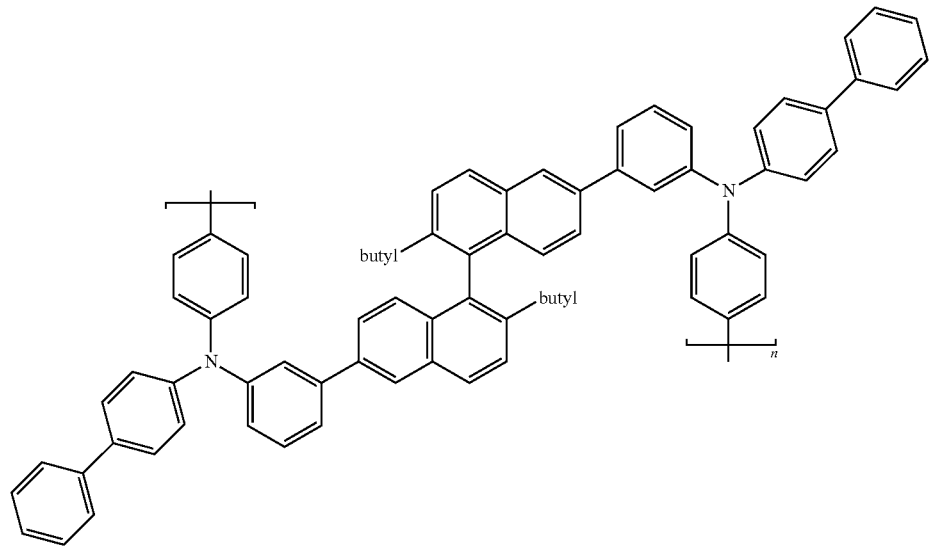
wherein n is an integer greater than 1;
Compound I:
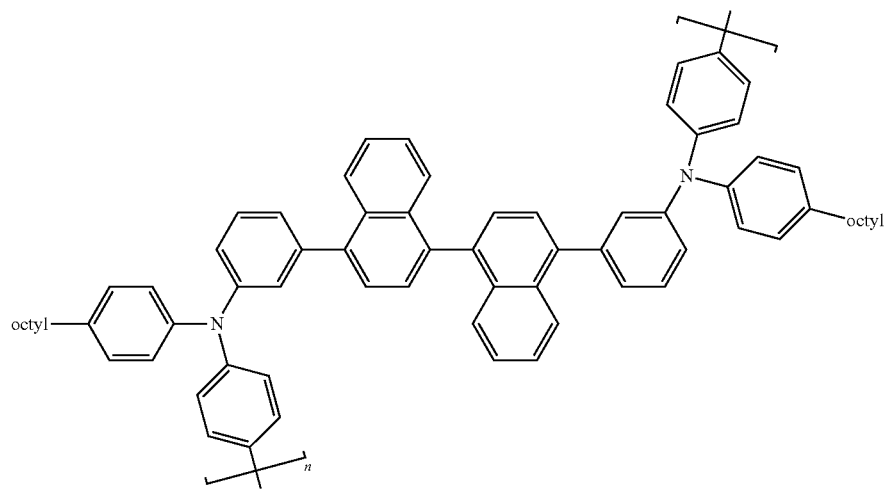
wherein n is an integer greater than 1;
Compound J:
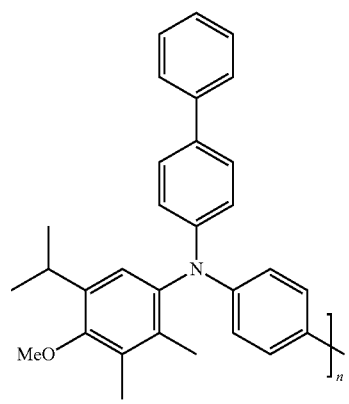
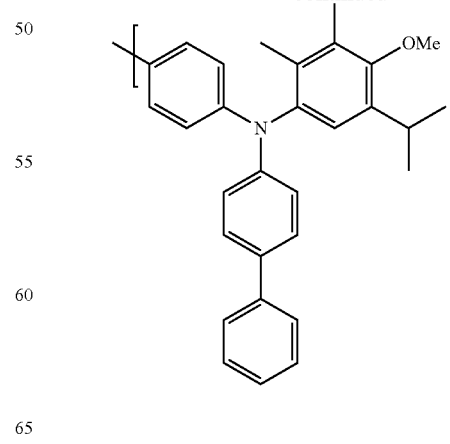
wherein n is an integer great than 1;

Compound K:
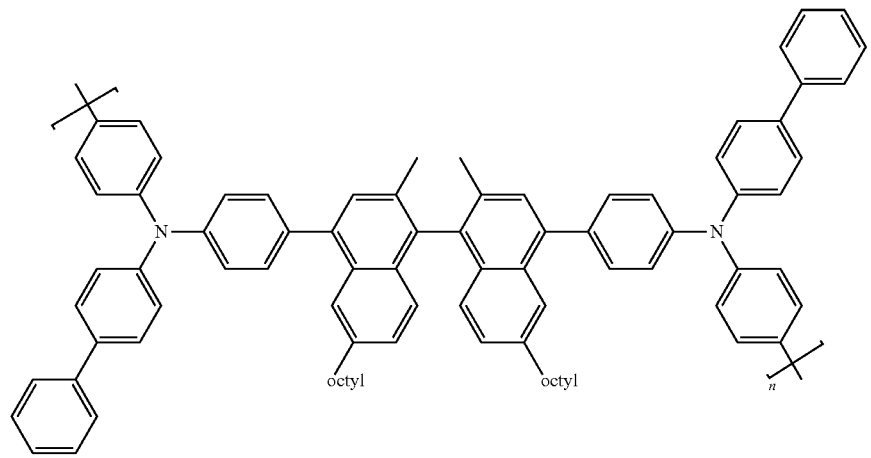
wherein n is an integer greater than 1;
Compound L:
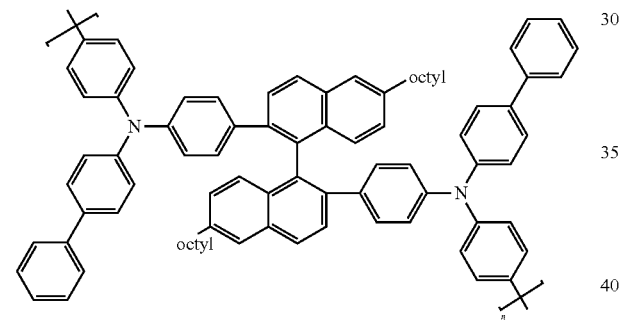
wherein n is an integer greater than 1;
Compound M:
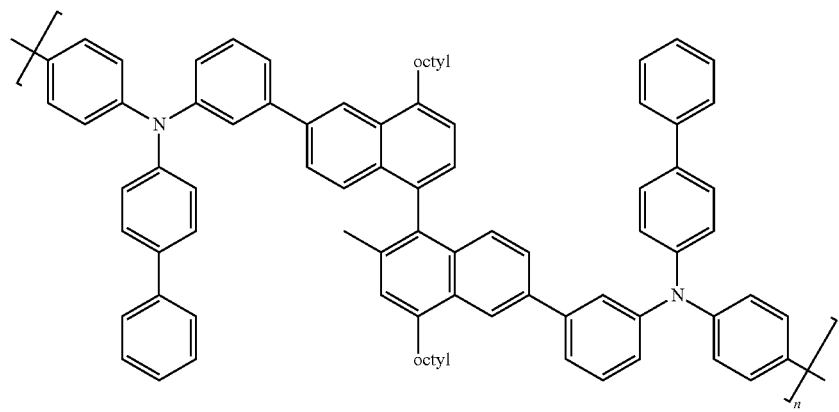
wherein n is an integer greater than 1; and Compound M1:

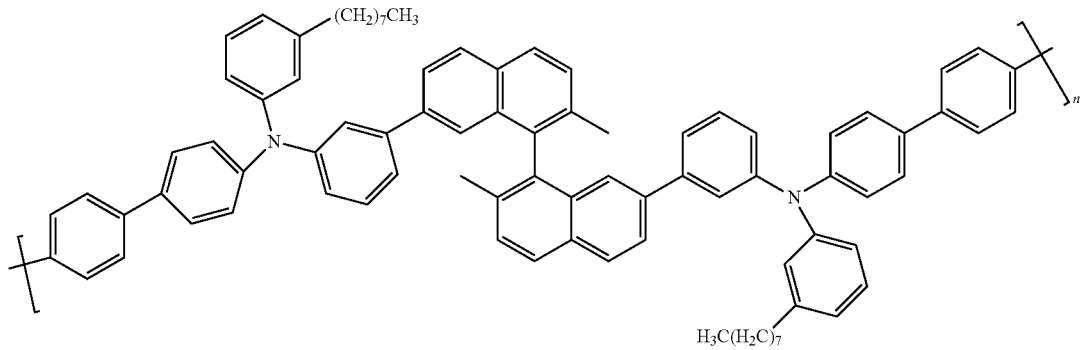

wherein n is an integer greater than 1.

13. An organic electronic device comprising a first electrical contact layer, a second electrical contact layer and an active layer therebetween, wherein the active layer comprises a compound having Formula II:

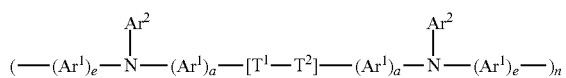

(II)

wherein:

Ar$^1$ is the same or different at each occurrence and is selected from the group consisting of phenylene, substituted phenylene, naphthylene, and substituted naphthylene;

Ar$^2$ is the same or different at each occurrence and is an aryl group;

T$^1$ and T$^2$ are independently the same or different at each occurrence and are conjugated moieties which are connected in a non-planar configuration;

a is the same or different at each occurrence and is an integer from 1 to 6;

e is the same or different at each occurrence and is an integer from 1 to 6; and n is an integer greater than 1.

14. The device of claim 13, wherein the active layer is a hole transport layer.

15. The device of claim 14, wherein the hole transport layer consists essentially of the Compound having Formula II.

16. The device of claim 13, wherein the active layer is a photoactive layer.

17. The device of claim 16, wherein the active layer further comprises a photoactive material.

18. The device of claim 17, wherein the active layer consists essentially of a photoactive material and a compound having Formula II.

* * * * *